United States Patent
Shaw et al.

(10) Patent No.: US 11,174,246 B2
(45) Date of Patent: Nov. 16, 2021

(54) DIRECT AMPK ACTIVATORS

(71) Applicant: Rigel Pharmaceuticals, Inc., South San Francisco, CA (US)

(72) Inventors: Simon Shaw, Oakland, CA (US); Xiang Xu, Foster City, CA (US); Sarkiz Issakani, Redwood City, CA (US); Rajinder Singh, Belmont, CA (US); Yasumichi Hitoshi, Brisbane, CA (US); Matthew Duncton, San Bruno, CA (US); Nan Lin, Foster City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 15/677,809

(22) Filed: Aug. 15, 2017

(65) Prior Publication Data
US 2018/0051006 A1   Feb. 22, 2018

Related U.S. Application Data

(60) Provisional application No. 62/376,950, filed on Aug. 19, 2016.

(51) Int. Cl.
| | | |
|---|---|---|
| *C07D 403/10* | (2006.01) | |
| *A61K 31/4184* | (2006.01) | |
| *C07D 403/04* | (2006.01) | |
| *C07D 235/26* | (2006.01) | |
| *C07D 403/12* | (2006.01) | |
| *C07D 403/14* | (2006.01) | |

(52) U.S. Cl.
CPC .......... *C07D 403/04* (2013.01); *C07D 235/26* (2013.01); *C07D 403/12* (2013.01); *C07D 403/14* (2013.01)

(58) Field of Classification Search
CPC .................... C07D 403/10; A61K 31/4184
See application file for complete search history.

(56) References Cited

U.S. PATENT DOCUMENTS 8,394,969 B2   3/2013   Bookser et al.

FOREIGN PATENT DOCUMENTS

| WO | 2010/036613 | 4/2010 |
|---|---|---|
| WO | 2010/047982 | 4/2010 |
| WO | 2011/106273 | 9/2011 |

OTHER PUBLICATIONS

Ex parte Cao, Decision rendered by Board of Patent Appeals and Interferences in U.S. Appl. No. 10/696,862, filed Sep. 21, 2011 (Year: 2011).*
Rana et al; "Small Molecule Adenosine 5'-Monophosphate Activated Protein Kinase (AMPK) Modulators and Human Diseases," Journal of Medicinal Chemistry, vol. 58, No. 1, Jan. 8, 2015, pp. 2-29.
International Search Report and Written Opinion dated Oct. 2, 2017 for International Application No. PCT/US2017/046959 filed Aug. 15, 2017, 12 pages.

* cited by examiner

*Primary Examiner* — Karen Cheng
(74) *Attorney, Agent, or Firm* — James J. Diehl

(57) ABSTRACT

Disclosed are benzimidazole compounds, as well as pharmaceutical compositions and methods of use thereof. One embodiment is a compound having the structure

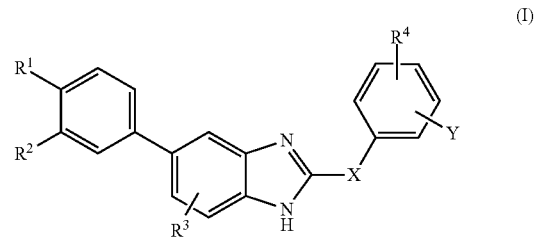

and pharmaceutically acceptable salts, prodrugs and N-oxides thereof (and solvates and hydrates thereof), wherein $R^1$, $R^2$, $R^3$, $R^4$, Y and X are as described herein. In certain embodiments, a compound disclosed herein activates AMPK, and can be used to treat disease by activating the AMPK pathway.

33 Claims, No Drawings

DIRECT AMPK ACTIVATORS

CROSS REFERENCE TO RELATED APPLICATIONS

This application claims the benefit of U.S. 62/376,950, filed Aug. 19, 2016, the entire contents of which are incorporated by reference.

BACKGROUND

Field of Invention

This invention relates to the field of compounds, pharmaceutical compositions, and methods of using the compounds and compositions containing them. This invention relates more particularly to the field of benzimidazole compounds and pharmaceutical compositions thereof, methods of activating AMPK with the compounds, and methods of treating and/or preventing disease with the compounds.

Technical Background

Adiponectin is a protein hormone exclusively expressed in and secreted from adipose tissue and is the most abundant adipose-specific protein. Adiponectin has been implicated in the modulation of glucose and lipid metabolism in insulin-sensitive tissues. Decreased circulating adiponectin levels have been demonstrated in some insulin-resistant states, such as obesity and type 2 diabetes mellitus and also in patients with coronary artery disease, atherosclerosis and hypertension. Adiponectin levels are positively correlated with insulin sensitivity, HDL (high density lipoprotein) levels and insulin stimulated glucose disposal and inversely correlated with adiposity and glucose, insulin and triglyceride levels. Thiazolidinedione drugs, which enhance insulin sensitivity through activation of the peroxisome proliferator-activated receptor-γ, increase endogenous adiponectin production in humans.

Adiponectin binds its receptors in liver and skeletal muscle and thereby activates the 5'-AMP-activated protein kinase (AMPK) pathway. Adiponectin receptors 1 and 2 are membrane-bound proteins found in skeletal muscle and liver tissue. Being a multi-substrate enzyme, AMPK regulates a variety of metabolic processes, such as glucose transport, glycolysis and lipid metabolism. It acts as a sensor of cellular energy homeostasis and is activated in response to certain hormones and muscle contraction as well as to intracellular metabolic stress signals such as exercise, ischemia, hypoxia and nutrient deprivation. Once activated, AMPK switches on catabolic pathways (such as fatty acid oxidation and glycolysis) and switches off ATP-consuming pathways (such as lipogenesis). Adiponectin improves insulin sensitivity by directly stimulating glucose uptake in adipocytes and muscle and by increasing fatty acid oxidation in liver and muscle, resulting in reduced circulating fatty acid levels and reduced intracellular triglyceride contents. Moreover, adiponectin decreases glycogen concentration by reducing the activity of glycogen synthase. Adiponectin also plays a protective role against inflammation and atherosclerosis. It suppresses the expression of adhesion molecules in vascular endothelial cells and cytokine production from macrophages, thus inhibiting the inflammatory processes that occur during the early phases of atherosclerosis.

SUMMARY

In view of the foregoing, we recognized that new therapeutic agents that activate the AMPK pathway may be useful and therefore desirable for treating disease states associated with circulating adiponectin levels, such as type II diabetes, atherosclerosis and cardiovascular disease.

Accordingly, the present invention comprises compounds, pharmaceutical compositions, and methods of using them to treat and/or prevent disease by activating AMPK.

Disclosed herein are compounds having structural formula (I)

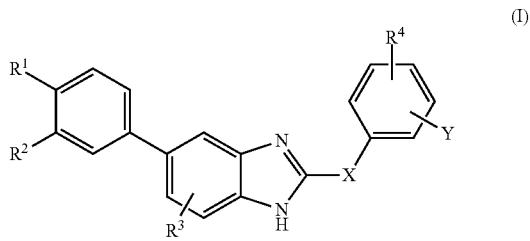

and pharmaceutically acceptable salts, prodrugs, and N-oxides thereof (and solvates and hydrates thereof), wherein $R^1$, $R^2$, $R^3$, $R^4$, Y and X are as described herein.

Also disclosed herein are pharmaceutical compositions. Examples of such compositions include those having at least one pharmaceutically acceptable carrier, diluent, or excipient; and a compound, pharmaceutically acceptable salt, prodrug, or N-oxide (or solvate or hydrate) as described herein.

Another aspect of the invention is a method for activating the AMPK pathway in a cell, the method comprising contacting the cell with an effective amount of a compound, pharmaceutically acceptable salt, prodrug, solvate, hydrate or N-oxide or composition described above. For the purposes of this disclosure, "contacting the cell" with a compound of the disclosure includes causing the cell to be contacted with the compound, e.g., by administering the compound to an individual resulting in the compound and a cell of the individual coming into contact in vivo.

Another aspect of the invention is a method for increasing fatty acid oxidation in a cell, the method comprising contacting the cell with an effective amount of a compound, pharmaceutically acceptable salt, prodrug, solvate, hydrate or N-oxide or composition described above.

Another aspect of the invention is a method for decreasing glycogen concentration in a cell, the method comprising contacting the cell with an effective amount of a compound, pharmaceutically acceptable salt, prodrug, solvate, hydrate or N-oxide or composition described above.

Another aspect of the invention is a method for reducing triglyceride levels in a subject, the method comprising administering to the subject an effective amount of a compound, pharmaceutically acceptable salt, prodrug, solvate, hydrate or N-oxide or composition described above.

Another aspect of the invention is a method for treating type II diabetes in a subject with type II diabetes, the method comprising administering to the subject a therapeutically effective amount of a compound, pharmaceutically acceptable salt, prodrug, solvate, hydrate or N-oxide or composition described above to ameleoriate the type II diabetes or at least one symptom thereof in the subject.

Another aspect of the invention is a method for treating atherosclerosis or cardiovascular disease in a subject with atherosclerosis or cardiovascular disease, the method comprising administering to the subject a therapeutically effective amount of a compound, pharmaceutically acceptable salt, prodrug, solvate, hydrate or N-oxide or composition described above to ameleoriate atherosclerosis, cardiovascular disease, or at least one symptom thereof in the subject.

Another aspect of the invention is a method for preventing atherosclerosis or cardiovascular disease in a subject, the method comprising administering to the subject an effective amount of a compound, pharmaceutically acceptable salt, prodrug, solvate, hydrate or N-oxide or composition described above to prevent atherosclerosis or cardiovascular disease in the subject.

All publications referenced herein are incorporated by reference in their entirety to the extent they are not inconsistent with the teachings presented herein.

DETAILED DESCRIPTION

In one aspect, the invention comprises compounds that activate AMPK.

In embodiment $I_1$ of this first aspect, the compounds have structural formula (I):

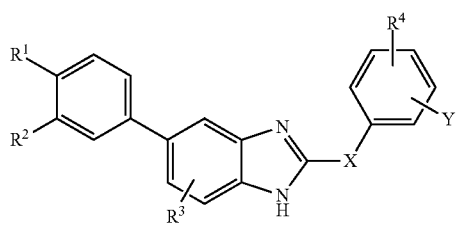

(I)

or a pharmaceutically acceptable salt, prodrug, or N-oxide thereof, or a solvate or hydrate thereof,
wherein
$R^1$ and $R^2$ together with the atoms to which they are attached form ring A, wherein ring A is a 5- or 6-membered Het optionally substituted with one or more $R^4$ groups that are each independently $C_{3-8}$Cak($C_{0-6}$alkyl), Hca($C_{0-6}$alkyl), Ar($C_{0-6}$alkyl), Het($C_{0-6}$alkyl), —O—$C_{0-6}$alkyl-$C_{3-8}$Cak, —O—$C_{0-6}$alkyl-Hca, —O—$C_{0-6}$alkyl-Ar, —O—$C_{0-6}$alkyl-Het, halogen, cyano, $C_{1-6}$alkyl, $C_{1-6}$haloalkyl, —$C_1$-$C_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR) wherein each Ar, Het, Cak, Hca, alkyl, alkoxy and haloalkyl group is optionally substituted by one or two -$R^{Ax}$ groups,
wherein each -$R^{Ax}$ is independently halogen, cyano, $C_{1-6}$alkyl, $C_{1-6}$haloalkyl, —$C_1$-$C_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

or one of $R^1$ and $R^2$ is Ar or Het, wherein Ar and Het are optionally substituted with one or more independently selected $R^4$ groups, and the other is hydrogen, halogen, cyano, $C_{1-6}$alkyl, $C_{1-6}$haloalkyl, —$C_1$-$C_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

$R^3$ and $R^4$ are independently hydrogen, halogen, cyano, $C_{1-6}$alkyl, $C_{1-6}$haloalkyl, —$C_1$-$C_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

X is —O—, —S—, —NR— or —CF$_2$—;
Y is, —NR$_2$, —CN, —C(O)OR$^Y$, —C(O)NHOH,

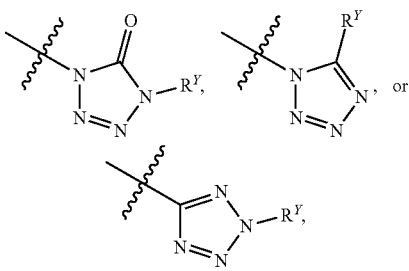

wherein $R^Y$ is hydrogen or $C_{1-6}$alkyl; and
each R is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano.

In embodiment I', the compounds are of embodiment $I_1$, provided that the compounds are not any of the compounds expressly recited in U.S. Pat. No. 8,394,969 or International Publication No. WO 2010/036613 A1.

In embodiment $I_2$, the compounds are of embodiment $I_1$, or a pharmaceutically acceptable salt, prodrug, or N-oxide thereof, or a solvate or hydrate thereof, provided that the compound is not:
5-((6-([1,1'-biphenyl]-4-yl)-1H-benzo[d]imidazol-2-yl) oxy)-2-methylbenzoic acid;
4-((5-([1,1'-biphenyl]-4-yl)-6-chloro-1H-benzo[d]imidazol-2-yl)oxy)benzoic acid;
4-((5-([1,1'-biphenyl]-4-yl)-6-chloro-1H-benzo[d]imidazol-2-yl)oxy)benzamide;
3-((5-([1,1'-biphenyl]-4-yl)-6-chloro-1H-benzo[d]imidazol-2-yl)oxy)benzoic acid;
3-((5-([1,1'-biphenyl]-4-yl)-6-chloro-1H-benzo[d]imidazol-2-yl)oxy)benzoate;
3-((5-([1,1'-biphenyl]-4-yl)-6-chloro-1H-benzo[d]imidazol-2-yl)oxy)-5-methylbenzoic acid;
5-((5-([1,1'-biphenyl]-4-yl)-6-chloro-1H-benzo[d]imidazol-2-yl)oxy)-2-methylbenzoic acid;
5-((5-([1,1'-biphenyl]-4-yl)-6-fluoro-1H-benzo[d]imidazol-2-yl)oxy)-2-methylbenzoic acid;
5-((6-chloro-5-(2'-methyl-[1,1'-biphenyl]-4-yl)-1H-benzo[d]imidazol-2-yl)oxy)-2-methylbenzoic acid;
4-((5-([1,1'-biphenyl]-4-yl)-6-chloro-1H-benzo[d]imidazol-2-yl)oxy)-2-chlorobenzoic acid;
4-((5-([1,1'-biphenyl]-4-yl)-6-chloro-1H-benzo[d]imidazol-2-yl)oxy)-2-hydroxybenzoic acid;
3-((5-([1,1'-biphenyl]-4-yl)-6-chloro-1H-benzo[d]imidazol-2-yl)oxy)-5-hydroxybenzoic acid;
5-((6-chloro-5-(2-methyl-[1,1'-biphenyl]-4-yl)-1H-benzo[d]imidazol-2-yl)oxy)-2-methylbenzoic acid;
3-((6-chloro-5-(2'-hydroxy-[1,1'-biphenyl]-4-yl)-1H-benzo[d]imidazol-2-yl)oxy)-5-methylbenzoic acid;
5-((6-chloro-5-(4'-hydroxy-[1,1'-biphenyl]-4-yl)-1H-benzo[d]imidazol-2-yl)oxy)-2-methylbenzoic acid;
5-((6-chloro-5-(2'-chloro-[1,1'-biphenyl]-4-yl)-1H-benzo[d]imidazol-2-yl)oxy)-2-methylbenzoic acid;

5-((6-chloro-5-(2'-fluoro-[1,1'-biphenyl]-4-yl)-1H-benzo[d] imidazol-2-yl)oxy)-2-methylbenzoic acid;
5-((5-([1,1'-biphenyl]-4-yl)-6-chloro-1H-benzo[d]imidazol-2-yl)oxy)-2-hydroxybenzoic acid;
5-((6-chloro-5-(4'-fluoro-[1,1'-biphenyl]-4-yl)-1H-benzo[d] imidazol-2-yl)oxy)-2-methylbenzoic acid;
2-(3-(2H-tetrazol-5-yl)phenoxy)-5-([1,1'-biphenyl]-4-yl)-6-chloro-1H-benzo[d]imidazole;
5-((6-chloro-5-(4'-cyano-[1,1'-biphenyl]-4-yl)-1H-benzo[d] imidazol-2-yl)oxy)-2-methylbenzoic acid;
5-((6-chloro-5-(4'-methoxy-[1,1'-biphenyl]-4-yl)-1H-benzo[d]imidazol-2-yl)oxy)-2-methylbenzoic acid;
5-((6-chloro-5-(3'-fluoro-[1,1'-biphenyl]-4-yl)-1H-benzo[d] imidazol-2-yl)oxy)-2-methylbenzoic acid;
5-((6-chloro-5-(3'-chloro-[1,1'-biphenyl]-4-yl)-1H-benzo[d] imidazol-2-yl)oxy)-2-methylbenzoic acid;
3-((5-([1,1'-biphenyl]-4-yl)-6-chloro-1H-benzo[d]imidazol-2-yl)oxy)-4-fluorobenzoic acid;
3-((5-([1,1'-biphenyl]-4-yl)-6-chloro-1H-benzo[d]imidazol-2-yl)oxy)-4-chlorobenzoic acid;
5-((5-([1,1'-biphenyl]-4-yl)-6-chloro-1H-benzo[d]imidazol-2-yl)oxy)-2-ethylbenzoic acid;
5-(6-fluoro-5-(2'-hydroxy-[1,1'-biphenyl]-4-yl)-1H-benzo[d]imidazol-2-yl)oxy)-2-methylbenzoic acid;
4'-(2-(3-carboxy-4-methylphenoxy)-6-chloro-1H-benzo[d] imidazol-5-yl)-[1,1'-biphenyl]-4-carboxylic acid;
4'-(2-(3-carboxy-4-methylphenoxy)-6-fluoro-1H-benzo[d] imidazol-5-yl)-[1,1'-biphenyl]-4-carboxylic acid;
4-((5-([1,1'-biphenyl]-4-yl)-6-chloro-1H-benzo[d]imidazol-2-yl)oxy)phthalic acid;
5-((6-chloro-5-(3'-methoxy-[1,1'-biphenyl]-4-yl)-1H-benzo[d]imidazol-2-yl)oxy)-2-methylbenzoic acid;
5-((5-(2'-amino-[1,1'-biphenyl]-4-yl)-6-chloro-1H-benzo[d] imidazol-2-yl)oxy)-2-methylbenzoic acid;
3-((5-([1,1'-biphenyl]-4-yl)-6-chloro-1H-benzo[d]imidazol-2-yl)oxy)-4-methoxybenzoic acid;
methyl 5-((5-([1,1'-biphenyl]-4-yl)-6-chloro-1H-benzo[d] imidazol-2-yl)oxy)-2-methylbenzoate;
methyl 5-((5-([1,1'-biphenyl]-4-yl)-6-fluoro-1H-benzo[d] imidazol-2-yl)oxy)-2-methylbenzoate;
5-((6-chloro-5-(2'-methoxy-[1,1'-biphenyl]-4-yl)-1H-benzo[d]imidazol-2-yl)oxy)-2-methylbenzoic acid;
5-((6-chloro-5-(2'-hydroxy-[1,1'-biphenyl]-4-yl)-1H-benzo[d]imidazol-2-yl)oxy)isophthalic acid;
methyl 5-((6-chloro-5-(2'-methyl-[1,1'-biphenyl]-4-yl)-1H-benzo[d]imidazol-2-yl)oxy)-2-methylbenzoate;
methyl 4-((5-([1,1'-biphenyl]-4-yl)-6-chloro-1H-benzo[d] imidazol-2-yl)oxy)-2-hydroxybenzoate;
methyl 5-((6-chloro-5-(2'-fluoro-[1,1'-biphenyl]-4-yl)-1H-benzo[d]imidazol-2-yl)oxy)-2-methylbenzoate;
methyl 5-((6-chloro-5-(2'-chloro-[1,1'-biphenyl]-4-yl)-1H-benzo[d]imidazol-2-yl)oxy)-2-methylbenzoate;
methyl 5-((5-chloro-6-(3'-fluoro-[1,1'-biphenyl]-4-yl)-1H-benzo[d]imidazol-2-yl)oxy)-2-methylbenzoate;
methyl 5-((6-chloro-5-(2'-methoxy-[1,1'-biphenyl]-4-yl)-1H-benzo[d]imidazol-2-yl)oxy)-2-methylbenzoate;
5-((5-(9H-carbazol-2-yl)-6-chloro-1H-benzo[d]imidazol-2-yl)oxy)-2-methylbenzoic acid;
dimethyl 4-((5-([1,1'-biphenyl]-4-yl)-6-chloro-1H-benzo[d] imidazol-2-yl)oxy)phthalate;
ethyl 4'-(6-fluoro-2-(3-(methoxycarbonyl)-4-methylphenoxy)-1H-benzo[d]imidazol-5-yl)-[1,1'-biphenyl]-4-carboxylate;
or a pharmaceutically acceptable salt thereof.

In embodiment $I_3$, the compounds are of embodiment $I_1$, or a pharmaceutically acceptable salt, prodrug, or N-oxide thereof, or a solvate or hydrate thereof, wherein $R^1$ and $R^2$ together with the atoms to which they are attached form ring A, wherein ring A is 5- or 6-membered Het optionally substituted with one or more $R^A$ groups that are each independently $C_{3-8}Cak(C_{0-6}alkyl)$, $Hca(C_{0-6}alkyl)$, $Ar(C_{0-6}alkyl)$, $Het(C_{0-6}alkyl)$, —O—$C_{0-6}alkyl$-$C_{3-8}Cak$, —O—$C_{0-6}alkyl$-Hca, —O—$C_{0-6}alkyl$-Ar, —O—$C_{0-6}alkyl$-Het, halogen, cyano, $C_{1-6}alkyl$, $C_{1-6}haloalkyl$, —$C_1$-$C_6alkoxy$, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR), wherein each Ar, Het, Cak, Hca, alkyl, alkoxy and haloalkyl group is optionally substituted by one or two -$R^{Ax}$ groups, wherein each -$R^{Ax}$ is independently halogen, cyano, $C_{1-6}alkyl$, $C_{1-6}haloalkyl$, —$C_1$-$C_6alkoxy$, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

or one of $R^1$ and $R^2$ is Ar or Het, wherein Ar and Het are substituted with one or more $R^A$ groups, and the other is hydrogen, halogen, cyano, $C_{1-6}alkyl$, $C_{1-6}haloalkyl$, —$C_1$-$C_6alkoxy$, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).

In embodiment $I_4$, the compounds are of embodiment $I_1$, or a pharmaceutically acceptable salt, prodrug, or N-oxide thereof, or a solvate or hydrate thereof, wherein $R^1$ and $R^2$ together with the atoms to which they are attached form a 5- or 6-membered Het optionally substituted with one or more $R^A$ groups.

In embodiment $I_5$, the compounds are of embodiment $I_1$, or a pharmaceutically acceptable salt, prodrug, or N-oxide thereof, or a solvate or hydrate thereof, wherein $R^1$ is Ar optionally substituted with one or more $R^A$ groups.

In embodiment $I_6$, the compounds are of any of embodiments I', $I_1$-$I_5$, or a pharmaceutically acceptable salt, prodrug, or N-oxide thereof, or a solvate or hydrate thereof, wherein X is —O—.

In embodiment $I_7$, the compounds are of any of embodiments I', $I_1$-$I_6$, or a pharmaceutically acceptable salt, prodrug, or N-oxide thereof, or a solvate or hydrate thereof, wherein each $R^A$ is independently halogen, cyano, $C_{1-6}alkyl$, $C_{1-6}haloalkyl$, —$C_1$-$C_6alkoxy$, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR), wherein each alkyl, alkoxy and haloalkyl group is optionally substituted by one or two -$R^{Ax}$ groups, wherein each -$R^{Ax}$ is independently halogen, cyano, $C_{1-6}alkyl$, $C_{1-6}haloalkyl$, —$C_1$-$C_6alkoxy$, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).

In embodiment I₈, the compounds are of any of embodiments I', I₁-I₇, or a pharmaceutically acceptable salt, prodrug, or N-oxide thereof, or a solvate or hydrate thereof, wherein each R is independently hydrogen, $C_1$-$C_6$alkyl or $C_1$-$C_6$haloalkyl.

The invention further comprises subgenera of formula (I) in which structural formula (I), $R^1$, $R^2$, $R^3$, $R^4$, Y and X are any group or combinations of groups as defined hereinbelow (e.g., wherein the compound is of structural formula (I) as defined in any of the above embodiments and $R^1$ is phenyl optionally substituted with one $R^4$ group, wherein $R^3$ is halogen; or the compound is formula (Ib), $R^1$/$R^2$ is group (1k), $R^3$ is group (2g), $R^4$ is group (3d) and Y is group (4f)):

Structural Formula (I) is One of Formulae (Ia)-(Ik):

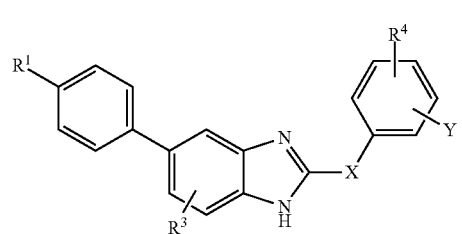
(Ia)

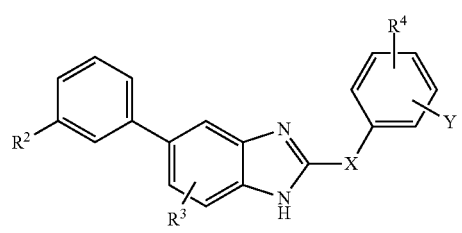
(Ib)

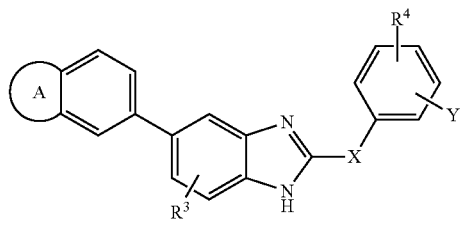
(Ic)

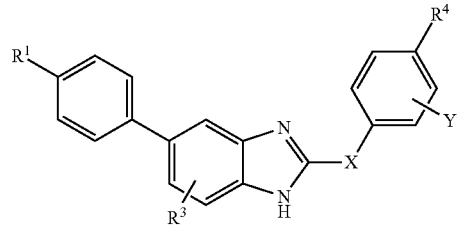
(Id)

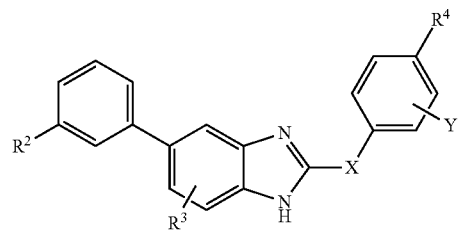
(Ie)

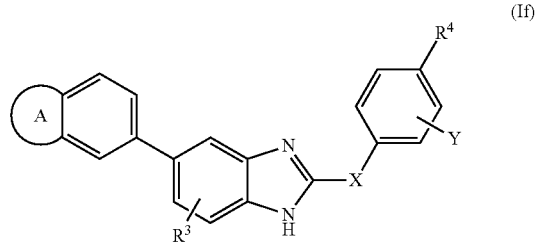
(If)

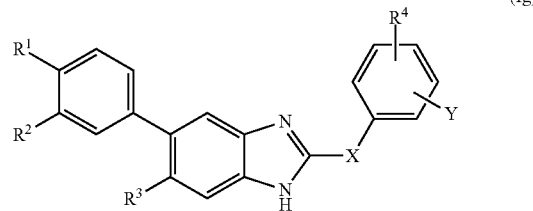
(Ig)

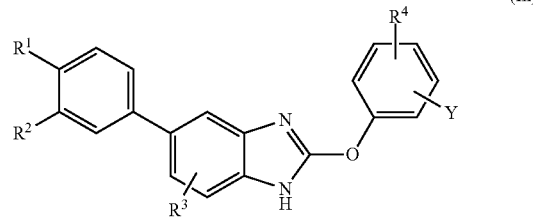
(Ih)

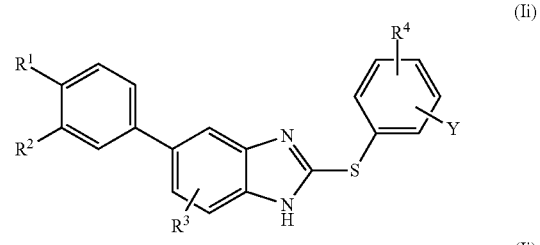
(Ii)

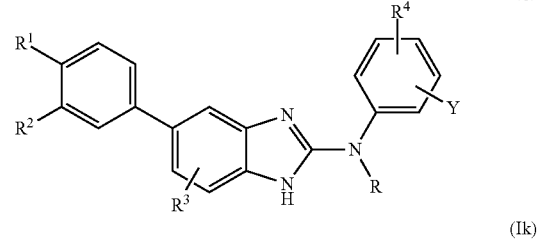
(Ij)

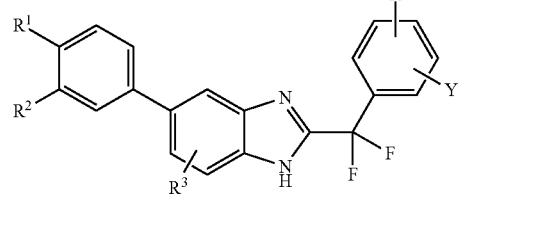
(Ik)

$R^1$ and $R^2$ are Selected from One of the Following Groups (1a)-(1uuu):

(1a) $R^1$ and $R^2$ together with the atoms to which they are attached form ring A, wherein ring A is a 5- or 6-membered Het optionally substituted with one or more $R^4$ groups that are each independently $C_{3-8}$Cak($C_{0-6}$alkyl), Hca($C_{0-6}$alkyl), Ar($C_{0-6}$alkyl), Het ($C_{0-6}$alkyl), —O—$C_{0-6}$alkyl-$C_{3-8}$Cak, —O—$C_{0-6}$alkyl-Hca, —O—$C_{0-6}$alkyl-Ar, —O—$C_{0-6}$alkyl-Het, halogen, cyano, $C_{1-6}$alkyl, $C_{1-6}$haloalkyl, —$C_1$-$C_6$alkoxy, —OR, —SR, —NR₂, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR) wherein each Ar, Het, Cak, Hca, alkyl, alkoxy and haloalkyl group is optionally substituted by one or two -R$^{Ax}$ groups,
wherein each -R$^{Ax}$ is independently halogen, cyano, C$_{1-6}$alkyl, C$_{1-6}$haloalkyl, —C$_1$-C$_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).

(1b) The group of (1a), wherein A is a 5-membered Het.
(1c) The group of (1a), wherein A is pyrrolyl, furanyl, thiophenyl, pyrazolyl, imidazolyl, isoxazolyl, oxazolyl, isothiazolyl or thiazolyl.
(1d) The group of (1a), wherein A is pyrrolyl, pyrazolyl or imidazolyl.
(1e) The group of (1a), wherein A is furanyl, thiophenyl, isoxazolyl, oxazolyl, isothiazolyl or thiazolyl.
(1f) The group of (1a), wherein A is furanyl, isoxazolyl or oxazolyl.
(1g) The group of (1a), wherein A is pyrrolyl.
(1h) The group of (1a), wherein A is N-methylpyrrolyl.
(1i) The group of (1a), wherein A is a 6-membered Het
(1j) The group of (1a), wherein A is pyridyl, pyrimidinyl, pyrazinyl or pyridazinyl.
(1k) The group of (1a), wherein A is pyrimidinyl, pyrazinyl or pyridazinyl.
(1l) The group of (1a), wherein A is pyridyl.
(1m) The group of (1a), wherein A is pyrimidinyl or pyridazinyl.
(1n) The group of (1a), wherein A is pyrimidinyl.
(1o) The group of any one of (1a)-(1n), wherein each R$^A$ is independently halogen, cyano, C$_{1-6}$alkyl, C$_{1-6}$haloalkyl, —C$_1$-C$_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR) wherein each alkyl, alkoxy and haloalkyl group is optionally substituted by one or two -R$^{Ax}$ groups,
wherein each -R$^{Ax}$ is independently halogen, cyano, C$_{1-6}$alkyl, C$_{1-6}$haloalkyl, —C$_1$-C$_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).

(1p) One of R$^1$ and R$^2$ is Ar or Het,
wherein Ar and Het are optionally substituted with one or more independently selected R$^A$ groups; and
the other is hydrogen, halogen, cyano, C$_{1-6}$alkyl, C$_{1-6}$haloalkyl, —C$_1$-C$_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).

(1q) The group of (1p), wherein R$^1$ is Ar or Het.
(1r) The group of (1p), wherein R$^1$ is Ar.
(1s) The group of (1p), wherein R$^1$ is phenyl.
(1t) The group of (1p), wherein R$^1$ is Het.
(1u) The group of (1p), wherein R$^2$ is Ar or Het.
(1v) The group of (1p), wherein R$^2$ is Ar.
(1w) The group of (1p), wherein R$^2$ is Het.
(1x) The group of (1s), wherein each R$^A$ is independently halogen, cyano, C$_{1-6}$alkyl, C$_{1-6}$haloalkyl, —C$_1$-C$_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).
(1y) The group of (1s), wherein each R$^A$ is independently halogen, cyano, C$_{1-6}$alkyl, C$_{1-6}$haloalkyl, —C$_1$-C$_6$alkoxy, —OR, —SR or —NR$_2$.
(1z) The group of (1s), wherein each R$^A$ is independently halogen, C$_{1-6}$alkyl, C$_{1-6}$haloalkyl, —OR, —SR or —NR$_2$.
(1aa) The group of (1s), wherein each R$^A$ is independently halogen, C$_{1-6}$alkyl or —OR.
(1bb) The group of (1s), wherein each R$^A$ is independently halogen or C$_{1-6}$alkyl.
(1cc) The group of (1s), wherein each R$^A$ is independently halogen or —OR.
(1dd) The group of (1s), wherein each R$^A$ is independently C$_{1-6}$alkyl or —OR.
(1ee) The group of (1s), wherein R$^A$ is halogen.
(1ff) The group of (1s), wherein each R$^A$ is independently R$^A$ is chloro of fluoro.
(1gg) The group of (1s), wherein R$^A$ is C$_{1-6}$alkyl.
(1hh) The group of (1s), wherein R$^A$ is methyl.
(1ii) The group of (1s), wherein R$^A$ is —OR.
(1jj) The group of (1s), wherein R$^A$ is —OH.
(1kk) The group of (1s), wherein R$^A$ is —OMe.
(1ll) The group of (1s), wherein each R$^A$ is independently cyano, C$_{1-6}$alkyl, C$_{1-6}$haloalkyl or —C$_1$-C$_6$alkoxy.
(1mm) The group of (1s), wherein each R$^A$ is independently C$_{1-6}$alkyl, C$_{1-6}$haloalkyl or —C$_1$-C$_6$alkoxy.
(1nn) The group of (1s), wherein each R$^A$ is independently C$_{1-6}$alkyl or C$_{1-6}$haloalkyl.
(1oo) The group of (1s), wherein R$^A$ is C$_{1-6}$haloalkyl.
(1pp) The group of (1s), wherein R$^A$ is —C$_1$-C$_6$alkoxy.
(1qq) The group of (1s), wherein each R$^A$ is independently —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).
(1rr) The group of (1s), wherein each R$^A$ is independently —C(O)R, —C(O)OR, —C(O)NR$_2$, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).
(1ss) The group of (1s), wherein each R$^A$ is independently —S(O)$_2$NR$_2$, —S(O)$_2$R, —OP(O)(OR)$_2$ or —CH$_2$—OP(O)(OR).
(1tt) The group of (1s), wherein each R$^A$ is independently —N(R)C(O)R, —OC(O)OR, —OC(O)NR$_2$, —N(R)C(O)OR, —N(R)C(O)NR$_2$ or —N(R)S(O)$_2$R.
(1uu) The group of (1s), wherein R$^A$ is —C(O)OR.
(1vv) The group of (1s), wherein R$^A$ is —C(O)OMe.
(1ww) The group of (1s), wherein R$^A$ is —C(O)OH.
(1xx) The group of (1s), wherein each R$^A$ is independently —OP(O)(OR)$_2$ or —CH$_2$—OP(O)(OR).
(1yy) The group of (1s), wherein R$^A$ is —CH$_2$—OP(O)(OR).
(1zz) Any of the groups of (1q)-(1t) or (1x)-(1yy), wherein R$^2$ is hydrogen, halogen, cyano, C$_{1-6}$alkyl, C$_{1-6}$haloalkyl, —C$_1$-C$_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).
(1aaa) The group of (1zz), wherein R$^2$ is hydrogen, halogen, C$_{1-6}$alkyl, C$_{1-6}$haloalkyl or —C$_1$-C$_6$alkoxy.

(1bbb) The group of (1zz), wherein $R^2$ is hydrogen, halogen or $C_{1-6}$alkyl.
(1ccc) The group of (1zz), wherein $R^2$ is hydrogen or halogen.
(1ddd) The group of (1zz), wherein $R^2$ is hydrogen or $C_{1-6}$alkyl.
(1eee) The group of (1zz), wherein $R^2$ is halogen or $C_{1-6}$alkyl.
(1fff) The group of (1zz), wherein $R^2$ is halogen.
(1ggg) The group of (1zz), wherein $R^2$ is $C_{1-6}$alkyl.
(1hhh) The group of (1zz), wherein $R^2$ is hydrogen, halogen, $C_{1-6}$haloalkyl or —$C_1$-$C_6$alkoxy.
(1iii) The group of (1zz), wherein $R^2$ is halogen, $C_{1-6}$haloalkyl or —$C_1$-$C_6$alkoxy.
(1jjj) The group of (1zz), wherein $R^2$ is —$C_1$-$C_6$alkoxy.
(1kkk) The group of (1zz), wherein $R^2$ is hydrogen.
(1lll) The group of (1zz), wherein $R^2$ is hydrogen, halogen, cyano, —OR, —SR or —$NR_2$.
(1mmm) The group of (1zz), wherein $R^2$ is hydrogen, halogen, or —OR.
(1nnn) The group of (1zz), wherein $R^2$ is hydrogen or —OR.
(1ooo) The group of (1zz), wherein $R^2$ is halogen, or —OR.
(1ppp) The group of (1zz), wherein $R^2$ is —OR.
(1qqq) The group of (1zz), wherein $R^2$ is hydrogen, halogen, cyano, $C_{1-6}$alkyl, $C_{1-6}$haloalkyl, —$C_1$-$C_6$alkoxy, —OR, —SR, —$NR_2$, —C(O)OR, —C(O)$NR_2$, —S(O)$_2NR_2$ or —S(O)$_2$R.
(1rrr) The group of (1zz), wherein $R^2$ is hydrogen, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —CH$_2$—OP(O)(OR).
(1sss) The group of (1zz), wherein $R^2$ is hydrogen, —C(O)R, —C(O)OR, —C(O)$NR_2$, —S(O)$_2NR_2$, —S(O)$_2$R, —OC(O)R, —N(R)C(O)R, —OC(O)OR or —OC(O)$NR_2$.
(1ttt) The group of (1zz), wherein $R^2$ is hydrogen or —C(O)OR.
(1uuu) The group of (1zz), wherein $R^2$ is —C(O)OR.

$R^3$ is Selected from One of the Following Groups (2a)-(2oo):

(2a) $R^3$ is hydrogen, halogen, cyano, $C_{1-6}$alkyl, $C_{1-6}$haloalkyl, —$C_1$-$C_6$alkoxy, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —CH$_2$—OP(O)(OR).
(2b) $R^3$ is halogen, cyano, $C_{1-6}$alkyl, $C_{1-6}$haloalkyl, —$C_1$-$C_6$alkoxy, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —CH$_2$—OP(O)(OR).
(2c) $R^3$ is hydrogen, halogen, cyano, $C_{1-6}$alkyl, $C_{1-6}$haloalkyl, —$C_1$-$C_6$alkoxy, —OR, —SR, —$NR_2$.
(2d) $R^3$ is hydrogen, halogen, $C_{1-6}$alkyl, $C_{1-6}$haloalkyl, —$C_1$-$C_6$alkoxy.
(2e) $R^3$ is hydrogen, halogen, $C_{1-6}$alkyl.
(2f) $R^3$ is hydrogen or halogen.
(2g) $R^3$ is hydrogen or $C_{1-6}$alkyl.
(2h) $R^3$ is halogen, cyano, $C_{1-6}$alkyl, $C_{1-6}$haloalkyl, —$C_1$-$C_6$alkoxy, —OR, —SR, —$NR_2$.
(2i) $R^3$ is halogen, $C_{1-6}$alkyl, $C_{1-6}$haloalkyl, —$C_1$-$C_6$alkoxy.
(2j) $R^3$ is halogen or $C_{1-6}$alkyl.
(2k) $R^3$ is halogen, $C_{1-6}$alkyl, $C_{1-6}$haloalkyl, —$C_1$-$C_6$alkoxy.
(2l) $R^3$ is hydrogen, $C_{1-6}$haloalkyl, —$C_1$-$C_6$alkoxy.
(2m) $R^3$ is halogen.
(2n) $R^3$ is fluoro or chloro.
(2o) $R^3$ is fluoro.
(2p) $R^3$ is chloro.
(2q) $R^3$ is $C_{1-6}$alkyl.
(2r) $R^3$ is methyl, ethyl or isopropyl.
(2s) $R^3$ is methyl or ethyl.
(2t) $R^3$ is methyl.
(2u) $R^3$ is ethyl.
(2v) $R^3$ is hydrogen.
(2w) $R^3$ is hydrogen, cyano, —OR, —SR, —$NR_2$.
(2x) $R^3$ is hydrogen, —OR, —SR, —$NR_2$.
(2y) $R^3$ is —OR, —SR, —$NR_2$.
(2z) $R^3$ is hydrogen or —OR.
(2aa) $R^3$ is —OR.
(2bb) $R^3$ is hydrogen, —C(O)R, —C(O)OR or —C(O)$NR_2$.
(2cc) $R^3$ is hydrogen, —C(O)OR or —C(O)$NR_2$.
(2dd) $R^3$ is hydrogen or —C(O)OR.
(2ee) $R^3$ is —C(O)OR.
(2ff) $R^3$ is hydrogen or —C(O)$NR_2$.
(2gg) $R^3$ is —C(O)$NR_2$.
(2hh) $R^3$ is hydrogen, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —CH$_2$—OP(O)(OR).
(2ii) $R^3$ is hydrogen, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —CH$_2$—OP(O)(OR).
(2jj) $R^3$ is hydrogen, —S(O)$_2NR_2$ or —S(O)$_2$R.
(2kk) $R^3$ is hydrogen, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —CH$_2$—OP(O)(OR).
(2ll) $R^3$ is hydrogen, —OC(O)R, —OC(O)OR, —OC(O)$NR_2$.
(2mm) $R^3$ is hydrogen, —N(R)C(O)R, —N(R)C(O)OR, —N(R)C(O)$NR_2$, —N(R)S(O)$_2$R.
(2nn) $R^3$ is hydrogen, —OC(O)R, —N(R)C(O)R, —OC(O)OR, —OC(O)$NR_2$, —N(R)C(O)OR, —N(R)C(O)$NR_2$ or —N(R)S(O)$_2$R.
(2oo) $R^3$ is hydrogen, —OP(O)(OR)$_2$ or —CH$_2$—OP(O)(OR).

$R^4$ is Selected from One of the Following Groups (3a)-(3mm):

(3a) $R^4$ is hydrogen, halogen, cyano, $C_{1-6}$alkyl, $C_{1-6}$haloalkyl, —$C_1$-$C_6$alkoxy, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —CH$_2$—OP(O)(OR).
(3b) $R^4$ is halogen, cyano, $C_{1-6}$alkyl, $C_{1-6}$haloalkyl, —$C_1$-$C_6$alkoxy, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —CH$_2$—OP(O)(OR).
(3c) $R^4$ is hydrogen, halogen, cyano, $C_{1-6}$alkyl, $C_{1-6}$haloalkyl, —$C_1$-$C_6$alkoxy, —OR, —SR, —$NR_2$.
(3d) $R^4$ is hydrogen, halogen, $C_{1-6}$alkyl, $C_{1-6}$haloalkyl, —$C_1$-$C_6$alkoxy.
(3e) $R^4$ is hydrogen, halogen, $C_{1-6}$alkyl.
(3f) $R^4$ is hydrogen or halogen.
(3g) $R^4$ is hydrogen or $C_{1-6}$alkyl.
(3h) $R^4$ is halogen, cyano, $C_{1-6}$alkyl, $C_{1-6}$haloalkyl, —$C_1$-$C_6$alkoxy, —OR, —SR, —$NR_2$.
(3i) $R^4$ is halogen, $C_{1-6}$alkyl, $C_{1-6}$haloalkyl, —$C_1$-$C_6$alkoxy.
(3j) $R^4$ is halogen or $C_{1-6}$alkyl.
(3k) $R^4$ is halogen, $C_{1-6}$alkyl, $C_{1-6}$haloalkyl, —$C_1$-$C_6$alkoxy.
(3l) $R^4$ is hydrogen, $C_{1-6}$haloalkyl, —$C_1$-$C_6$alkoxy.

(3m) $R^4$ is halogen, $C_{1-6}$alkyl.
(3n) $R^4$ is halogen.
(3o) $R^4$ is $C_{1-6}$alkyl.
(3p) $R^4$ is methyl, ethyl or isopropyl.
(3q) $R^4$ is methyl or ethyl.
(3r) $R^4$ is methyl.
(3s) $R^4$ is ethyl.
(3t) $R^4$ is hydrogen.
(3u) $R^4$ is hydrogen, cyano, —OR, —SR, —NR$_2$.
(3v) $R^4$ is hydrogen, —OR, —SR, —NR$_2$.
(3w) $R^4$ is —OR, —SR, —NR$_2$.
(3x) $R^4$ is hydrogen or —OR.
(3y) $R^4$ is —OR.
(3z) $R^4$ is hydrogen, —C(O)R, —C(O)OR or —C(O)NR$_2$.
(3aa) $R^4$ is hydrogen, —C(O)OR or —C(O)NR$_2$.
(3bb) $R^4$ is hydrogen or —C(O)OR.
(3cc) $R^4$ is —C(O)OR.
(3dd) $R^4$ is hydrogen or —C(O)NR$_2$.
(3ee) $R^4$ is —C(O)NR$_2$.
(3ff) $R^4$ is hydrogen, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).
(3gg) $R^4$ is hydrogen, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).
(3hh) $R^4$ is hydrogen, —S(O)$_2$NR$_2$ or —S(O)$_2$R.
(3ii) $R^4$ is hydrogen, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).
(3jj) $R^4$ is hydrogen, —OC(O)R, —OC(O)OR, —OC(O)NR$_2$.
(3kk) $R^4$ is hydrogen, —N(R)C(O)R, —N(R)C(O)OR, —N(R)C(O)NR$_2$, —N(R)S(O)$_2$R.
(3ll) $R^4$ is hydrogen, —OC(O)R, —N(R)C(O)R, —OC(O)OR, —OC(O)NR$_2$, —N(R)C(O)OR, —N(R)C(O)NR$_2$ or —N(R)S(O)$_2$R.
(3mm) $R^4$ is hydrogen, —OP(O)(OR)$_2$ or —CH$_2$—OP(O)(OR).

Y is Selected from One of the Following Groups (4a)-(4cc):

(4a) Y is —NR$_2$, —CN, —C(O)OR$^Y$, —C(O)NHOH,

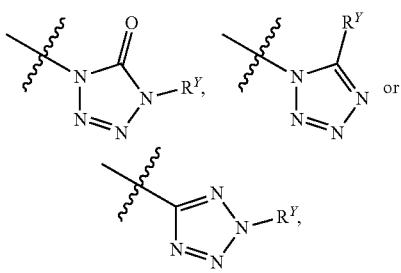

(4b) Y is —C(O)NHOH,

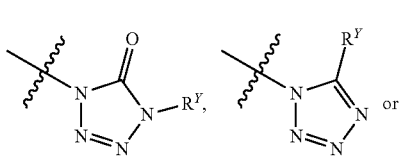

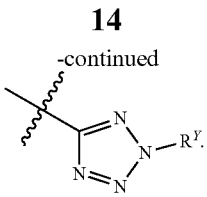

(4c) Y is —C(O)OR$^Y$, —C(O)NHOH or

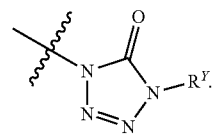

(4d) Y is —C(O)OH, —C(O)NHOH

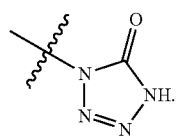 [SMILES: *n1nn[nH]c1=O]

(4e) Y is —C(O)NHOH or

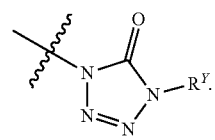

(4f) Y is —C(O)NHOH or

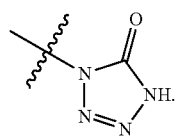 [SMILES: *n1nn[nH]c1=O]

(4g) Y is

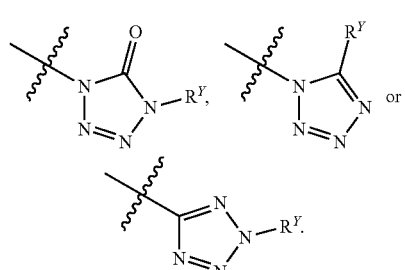

(4h) Y is —NR$_2$, —CN, —C(O)OR$^Y$ or —C(O)NHOH.
(4i) Y is —C(O)OH or —C(O)NHOH.
(4j) Y is —NR$_2$ or —CN.
(4k) Y is —NR$_2$, or —C(O)NHOH.
(4l) Y is —NR$_2$, or —C(O)OR$^Y$.
(4m) Y is —CN or —C(O)NHOH.
(4n) Y is —CN or —C(O)OR$^Y$.
(4o) Y is —NR$_2$.

(4p) Y is NH$_2$.
(4q) Y is —CN.
(4r) Y is —C(O)OR$^Y$.
(4s) Y is —C(O)OH.
(4t) Y is —C(O)NHOH.
(4u) Y is

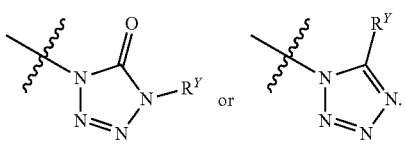

(4v) Y is

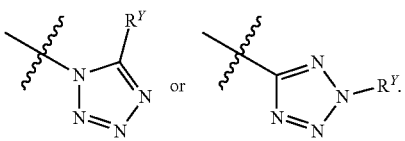

(4w) Y is

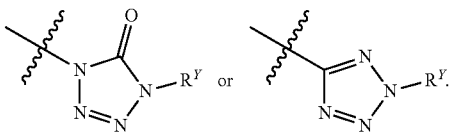

(4x) Y is

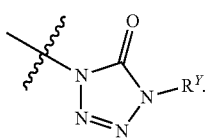

(4y) Y is

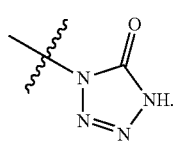

(4z) Y is

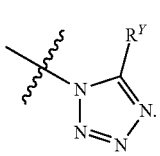

(4aa) Y is

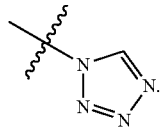 [SMILES: *n1cnnn1]

(4bb) Y is

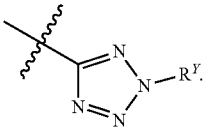

(4cc) Y is

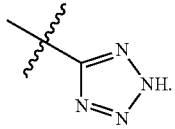 [SMILES: *c1nn[nH]n1]

Particular embodiments of this aspect of the invention comprise compounds of any one of the formulae (I), and (Ia)-(Ig), each as defined in each of the following rows (or a pharmaceutically acceptable salt, prodrug, or N-oxide thereof, or a solvate or hydrate thereof), wherein each entry is a group number as defined above (e.g., (3y) refers to R$^3$ is —OR), and a dash "-" indicates that the variable is as defined in embodiment I$_1$ or defined according to any one of the applicable variable definitions (1a)-(4cc) [e.g., when R$^1$ is a dash, it can be either as defined in any of embodiments I$_1$-I$_8$ or any one of definitions (3a)-(3mm)]:

|        | (I)  | R$^1$/R$^2$ | R$^3$ | R$^4$ | Y     |
|--------|------|-------------|-------|-------|-------|
| (1)-1  | (Ia) | (1a)        | (2a)  | (3a)  | (4a)  |
| (1)-2  | (Ia) | (1b)        | (2c)  | (3c)  | (4c)  |
| (1)-3  | (Ia) | (1g)        | (2d)  | (3g)  | (4i)  |
| (1)-4  | (Ia) | (1h)        | (2f)  | (3h)  | (4j)  |
| (1)-5  | (Ia) | (1i)        | (2h)  | (3o)  | (4l)  |
| (1)-6  | (Ia) | (1p)        | (2k)  | (3p)  | (4u)  |
| (1)-7  | (Ia) | (1r)        | (2m)  | (3r)  | (4x)  |
| (1)-8  | (Ia) | (1s)        | (2n)  | (3t)  | (4))  |
| (1)-9  | (Ia) | (1x)        | (2o)  | (3u)  | (4z)  |
| (1)-10 | (Ia) | (1ii)       | (2p)  | (3x)  | (4aa) |
| (1)-11 | (Ia) | (1jj)       | (2t)  | (3g)  | (4bb) |
| (1)-12 | (Ia) | (1zz)       | (2d)  | (3h)  | (4cc) |
| (1)-13 | (Ia) | (1bbb)      | (2f)  | (3o)  | (4a)  |
| (1)-14 | (Ia) | (1kkk)      | (2h)  | (3p)  | (4c)  |
| (1)-15 | (Ia) | (1a)        | (2k)  | (3c)  | (4i)  |
| (1)-16 | (Ia) | (1b)        | (2m)  | (3g)  | (4j)  |
| (1)-17 | (Ia) | (1g)        | (2c)  | (3h)  | (4l)  |
| (1)-18 | (Ia) | (1h)        | (2d)  | (3o)  | (4u)  |
| (1)-19 | (Ia) | (1i)        | (2f)  | (3p)  | (4x)  |
| (1)-20 | (Ia) | (1p)        | (2h)  | (3r)  | (4y)  |
| (1)-21 | (Ia) | (1r)        | (2k)  | (3t)  | (4z)  |
| (1)-22 | (Ia) | (1s)        | (2m)  | (3u)  | (4aa) |
| (1)-23 | (Ia) | (1x)        | (2n)  | (3x)  | (4bb) |
| (1)-24 | (Ia) | (1ii)       | (2o)  | (3g)  | (4cc) |
| (1)-25 | (Ia) | (1jj)       | (2p)  | (3h)  | (4j)  |
| (1)-26 | (Ia) | (1zz)       | (2t)  | (3o)  | (4l)  |
| (1)-27 | (Ia) | (1bbb)      | (2d)  | (3p)  | (4u)  |
| (1)-28 | (Ia) | (1kkk)      | (2f)  | (3c)  | (4x)  |
| (1)-29 | (Ia) | (1a)        | (2h)  | (3g)  | (4y)  |

|  | (I) | R¹/R² | R³ | R⁴ | Y |
|---|---|---|---|---|---|
| (1)-30 | (Ia) | (1b) | (2k) | (3h) | (4z) |
| (1)-31 | (Ia) | (1g) | (2m) | (3o) | (4aa) |
| (1)-32 | (Ia) | (1h) | (2c) | (3p) | (4bb) |
| (1)-33 | (Ia) | (1i) | (2d) | (3r) | (4cc) |
| (1)-34 | (Ia) | (1p) | (2f) | (3t) | (4a) |
| (1)-35 | (Ia) | (1r) | (2h) | (3u) | (4c) |
| (1)-36 | (Ia) | (1s) | (2k) | (3x) | (4i) |
| (1)-37 | (Ia) | (1x) | (2m) | (3g) | (4j) |
| (1)-38 | (Ia) | (1ii) | (2n) | (3h) | (4l) |
| (1)-39 | (Ia) | (1jj) | (2o) | (3o) | (4u) |
| (1)-40 | (Ia) | (1zz) | (2p) | (3p) | (4x) |
| (1)-41 | (Ib) | (1bbb) | (2t) | (3a) | (4y) |
| (1)-42 | (Ib) | (1kkk) | (2c) | (3c) | (4a) |
| (1)-43 | (Ib) | (1g) | (2d) | (3g) | (4c) |
| (1)-44 | (Ib) | (1h) | (2f) | (3h) | (4i) |
| (1)-45 | (Ib) | (1i) | (2h) | (3o) | (4j) |
| (1)-46 | (Ib) | (1p) | (2k) | (3p) | (4l) |
| (1)-47 | (Ib) | (1r) | (2m) | (3r) | (4a) |
| (1)-48 | (Ib) | (1s) | (2f) | (3t) | (4c) |
| (1)-49 | (Ib) | (1x) | (2m) | (3u) | (4i) |
| (1)-50 | (Ib) | (1ii) | (2n) | (3x) | (4j) |
| (1)-51 | (Ib) | (1jj) | (2n) | (3c) | (4l) |
| (1)-52 | (Ib) | (1zz) | (2o) | (3g) | (4u) |
| (1)-53 | (Ib) | (1bbb) | (2p) | (3h) | (4x) |
| (1)-54 | (Ib) | (1kkk) | (2t) | (3o) | (4y) |
| (1)-55 | (Ib) | (1a) | (2c) | (3p) | (4u) |
| (1)-56 | (Ic) | (1b) | (2d) | (3r) | (4x) |
| (1)-57 | (Ic) | (1g) | (2c) | (3t) | (4y) |
| (1)-58 | (Ic) | (1h) | (2d) | (3g) | (4z) |
| (1)-59 | (Ic) | (1i) | (2f) | (3h) | (4aa) |
| (1)-60 | (Ic) | (1p) | (2h) | (3o) | (4y) |
| (1)-61 | (Ic) | (1a) | (2k) | (3p) | (4z) |
| (1)-62 | (Ic) | (1b) | (2m) | (3r) | (4aa) |
| (1)-63 | (Ic) | (1g) | (2n) | (3t) | (4u) |
| (1)-64 | (Ic) | (1h) | (2o) | (3u) | (4x) |
| (1)-65 | (Ic) | (1i) | (2p) | (3x) | (4y) |
| (1)-66 | (Ic) | (1p) | (2t) | (3c) | (4z) |
| (1)-67 | (Ic) | (1r) | (2c) | (3g) | (4aa) |
| (1)-68 | (Ic) | (1a) | (2d) | (3h) | (4y) |
| (1)-69 | (Ic) | (1b) | (2f) | (3o) | (4a) |
| (1)-70 | (Ic) | (1g) | (2h) | (3c) | (4c) |
| (1)-71 | (Ic) | (1h) | (2k) | (3g) | (4i) |
| (1)-72 | (Ic) | (1i) | (2m) | (3h) | (4c) |
| (1)-73 | (Ic) | (1p) | (2h) | (3o) | (4i) |
| (1)-74 | (Ic) | (1r) | (2k) | (3p) | (4j) |
| (1)-75 | (Ic) | (1s) | (2m) | (3r) | (4l) |
| (1)-76 | (Ic) | (1x) | (2c) | (3t) | (4u) |
| (1)-77 | (Ic) | (1ii) | (2d) | (3h) | (4x) |
| (1)-78 | (Ic) | (1a) | (2a) | (3o) | (4y) |
| (1)-79 | (Ic) | (1b) | (2c) | (3p) | (4aa) |
| (1)-80 | (Ic) | (1g) | (2d) | (3r) | (4l) |
| (1)-81 | (Ic) | (1a) | (2f) | (3t) | (4u) |
| (1)-82 | (Ic) | (1a) | (2h) | (3u) | (4x) |
| (1)-83 | (Ic) | (1b) | (2k) | (3x) | (4y) |
| (1)-84 | (Ic) | (1g) | (2m) | (3p) | (4z) |
| (1)-85 | (Ic) | (1h) | (2n) | (3r) | (4aa) |
| (1)-86 | (Ic) | (1i) | (2o) | (3t) | (4bb) |
| (1)-87 | (Ic) | (1p) | (2p) | (3u) | (4cc) |
| (1)-88 | (Ic) | (1r) | (2h) | (3a) | (4u) |
| (1)-89 | (Ic) | (1s) | (2k) | (3c) | (4x) |
| (1)-90 | (Ic) | (1x) | (2m) | (3g) | (4z) |
| (1)-91 | (Ic) | (1ii) | (2a) | (3h) | (4aa) |
| (1)-92 | (Ic) | (1jj) | (2c) | (3p) | (4l) |
| (1)-93 | (Ic) | (1zz) | (2d) | (3r) | (4u) |
| (1)-94 | (Ic) | (1bbb) | (2f) | (3u) | (4x) |
| (1)-95 | (Ic) | (1kkk) | (2h) | (3u) | (4y) |
| (1)-96 | (Id) | (1a) | (2k) | (3a) | (4z) |
| (1)-97 | (Id) | (1b) | (2m) | (3c) | (4aa) |
| (1)-98 | (Id) | (1g) | (2n) | (3g) | (4bb) |
| (1)-99 | (Id) | (1h) | (2o) | (3h) | (4cc) |
| (1)-100 | (Id) | (1i) | (2p) | (3o) | (4u) |
| (1)-101 | (Id) | (1p) | (2t) | (3p) | (4x) |
| (1)-102 | (Id) | (1a) | (2d) | (3r) | (4y) |
| (1)-103 | (Id) | (1b) | (2f) | (3t) | (4z) |
| (1)-104 | (Id) | (1g) | (2h) | (3u) | (4aa) |
| (1)-105 | (Id) | (1h) | (2k) | (3x) | (4a) |
| (1)-106 | (Id) | (1i) | (2m) | (3p) | (4c) |
| (1)-107 | (Id) | (1p) | (2d) | (3r) | (4i) |
| (1)-108 | (Id) | (1r) | (2f) | (3t) | (4j) |
| (1)-109 | (Id) | (1s) | (2h) | (3u) | (4l) |
| (1)-110 | (Id) | (1x) | (2k) | (3c) | (4u) |
| (1)-111 | (Id) | (1a) | (2m) | (3g) | (4x) |
| (1)-112 | (Id) | (1b) | (2n) | (3h) | (4y) |
| (1)-113 | (Id) | (1g) | (2o) | (3o) | (4z) |
| (1)-114 | (Id) | (1h) | (2p) | (3p) | (4aa) |
| (1)-115 | (Id) | (1i) | (2t) | (3r) | (4bb) |
| (1)-116 | (Id) | (1p) | (2m) | (3t) | (4cc) |
| (1)-117 | (Id) | (1r) | (2a) | (3a) | (4x) |
| (1)-118 | (Id) | (1s) | (2d) | (3c) | (4z) |
| (1)-119 | (Id) | (1x) | (2f) | (3g) | (4aa) |
| (1)-120 | (Id) | (1ii) | (2h) | (3h) | (4c) |
| (1)-121 | (Id) | (1jj) | (2k) | (3o) | (4i) |
| (1)-122 | (Id) | (1zz) | (2m) | (3p) | (4j) |
| (1)-123 | (Id) | (1bbb) | (2c) | (3r) | (4l) |
| (1)-124 | (Id) | (1kkk) | (2d) | (3t) | (4u) |
| (1)-125 | (Id) | (1r) | (2f) | (3u) | (4x) |
| (1)-126 | (Id) | (1s) | (2h) | (3x) | (4y) |
| (1)-127 | (Id) | (1x) | (2k) | (3a) | (4z) |
| (1)-128 | (Id) | (1a) | (2m) | (3c) | (4aa) |
| (1)-129 | (Id) | (1b) | (2n) | (3g) | (4bb) |
| (1)-130 | (Id) | (1g) | (2o) | (3h) | (4cc) |
| (1)-131 | (Id) | (1h) | (2p) | (3g) | (4l) |
| (1)-132 | (Id) | (1r) | (2t) | (3h) | (4u) |
| (1)-133 | (Id) | (1s) | (2h) | (3o) | (4x) |
| (1)-134 | (Id) | (1x) | (2k) | (3p) | (4y) |
| (1)-135 | (Id) | (1a) | (2m) | (3r) | (4z) |
| (1)-136 | (Ie) | (1b) | (2a) | (3t) | (4aa) |
| (1)-137 | (Ie) | (1g) | (2c) | (3h) | (4bb) |
| (1)-138 | (Ie) | (1h) | (2d) | (3o) | (4cc) |
| (1)-139 | (Ie) | (1i) | (2f) | (3p) | (4x) |
| (1)-140 | (Ie) | (1h) | (2h) | (3r) | (4z) |
| (1)-141 | (Ie) | (1i) | (2k) | (3t) | (4aa) |
| (1)-142 | (Ie) | (1p) | (2m) | (3u) | (4a) |
| (1)-143 | (Ie) | (1r) | (2n) | (3x) | (4c) |
| (1)-144 | (Ie) | (1s) | (2o) | (3c) | (4i) |
| (1)-145 | (Ie) | (1x) | (2p) | (3g) | (4j) |
| (1)-146 | (Ie) | (1ii) | (2t) | (3h) | (4l) |
| (1)-147 | (Ie) | (1jj) | (2d) | (3o) | (4u) |
| (1)-148 | (Ie) | (1zz) | (2f) | (3p) | (4x) |
| (1)-149 | (Ie) | (1bbb) | (2h) | (3r) | (4y) |
| (1)-150 | (Ie) | (1kkk) | (2k) | (3t) | (4z) |
| (1)-151 | (If) | (1a) | (2m) | (3o) | (4aa) |
| (1)-152 | (If) | (1b) | (2a) | (3p) | (4bb) |
| (1)-153 | (If) | (1g) | (2c) | (3r) | (4cc) |
| (1)-154 | (If) | (1h) | (2d) | (3t) | (4x) |
| (1)-155 | (If) | (1i) | (2f) | (3u) | (4z) |
| (1)-156 | (If) | (1p) | (2h) | (3x) | (4aa) |
| (1)-157 | (If) | (1r) | (2k) | (3a) | (4a) |
| (1)-158 | (If) | (1s) | (2m) | (3c) | (4c) |
| (1)-159 | (If) | (1x) | (2n) | (3a) | (4i) |
| (1)-160 | (If) | (1ii) | (2o) | (3c) | (4j) |
| (1)-161 | (If) | (1jj) | (2p) | (3g) | (4l) |
| (1)-162 | (If) | (1zz) | (2t) | (3h) | (4u) |
| (1)-163 | (If) | (1bbb) | (2h) | (3c) | (4x) |
| (1)-164 | (If) | (1kkk) | (2k) | (3g) | (4y) |
| (1)-165 | (If) | (1r) | (2m) | (3h) | (4z) |
| (1)-166 | (If) | (1s) | (2c) | (3o) | (4aa) |
| (1)-167 | (If) | (1x) | (2d) | (3p) | (4bb) |
| (1)-168 | (If) | (1a) | (2f) | (3r) | (4cc) |
| (1)-169 | (If) | (1b) | (2h) | (3t) | (4c) |
| (1)-170 | (If) | (1g) | (2k) | (3u) | (4i) |
| (1)-171 | (If) | (1h) | (2m) | (3x) | (4j) |
| (1)-172 | (If) | (1i) | (2n) | (3c) | (4l) |
| (1)-173 | (If) | (1a) | (2o) | (3g) | (4u) |
| (1)-174 | (If) | (1b) | (2p) | (3h) | (4x) |
| (1)-175 | (If) | (1g) | (2t) | (3o) | (4y) |
| (1)-176 | (If) | (1h) | (2d) | (3p) | (4z) |
| (1)-177 | (If) | (1i) | (2f) | (3r) | (4aa) |
| (1)-178 | (If) | (1p) | (2h) | (3t) | (4bb) |
| (1)-179 | (If) | (1r) | (2k) | (3h) | (4cc) |
| (1)-180 | (If) | (1s) | (2m) | (3o) | (4j) |
| (1)-181 | (If) | (1x) | (2d) | (3p) | (4l) |
| (1)-182 | (If) | (1ii) | (2f) | (3r) | (4u) |
| (1)-183 | (If) | (1jj) | (2h) | (3t) | (4x) |

|  | (I) | R¹/R² | R³ | R⁴ | Y |
|---|---|---|---|---|---|
| (1)-184 | (If) | (1zz) | (2k) | (3u) | (4y) |
| (1)-185 | (If) | (1bbb) | (2m) | (3x) | (4i) |
| (1)-186 | (If) | (1kkk) | (2n) | (3a) | (4j) |
| (1)-187 | (If) | (1r) | (2o) | (3c) | (4l) |
| (1)-188 | (If) | (1s) | (2p) | (3g) | (4u) |
| (1)-189 | (If) | (1x) | (2t) | (3h) | (4x) |
| (1)-190 | (If) | (1a) | (2d) | (3o) | (4y) |
| (1)-191 | (Ig) | (1b) | (2f) | (3p) | (4z) |
| (1)-192 | (Ig) | (1g) | (2h) | (3r) | (4aa) |
| (1)-193 | (Ig) | (1h) | (2k) | (3t) | (4bb) |
| (1)-194 | (Ig) | (1i) | (2m) | (3u) | (4cc) |
| (1)-195 | (Ig) | (1i) | (2a) | (3x) | (4j) |
| (1)-196 | (Ig) | (1p) | (2c) | (3o) | (4l) |
| (1)-197 | (Ig) | (1r) | (2d) | (3p) | (4u) |
| (1)-198 | (Ig) | (1s) | (2f) | (3r) | (4x) |
| (1)-199 | (Ig) | (1x) | (2h) | (3t) | (4y) |
| (1)-200 | (Ig) | (1ii) | (2k) | (3o) | (4c) |
| (1)-201 | (Ig) | (1jj) | (2m) | (3a) | (4i) |
| (1)-202 | (Ig) | (1zz) | (2n) | (3c) | (4j) |
| (1)-203 | (Ig) | (1bbb) | (2o) | (3g) | (4l) |
| (1)-204 | (Ig) | (1kkk) | (2p) | (3h) | (4u) |
| (1)-205 | (Ig) | (1jj) | (2t) | (3o) | (4x) |
| (1)-206 | (Ih) | (1a) | (2k) | (3p) | (4y) |
| (1)-207 | (Ih) | (1b) | (2a) | (3r) | (4z) |
| (1)-208 | (Ih) | (1g) | (2c) | (3t) | (4aa) |
| (1)-209 | (Ih) | (1h) | (2d) | (3u) | (4bb) |
| (1)-210 | (Ih) | (1i) | (2f) | (3x) | (4cc) |
| (1)-211 | (Ih) | (1p) | (2h) | (3o) | (4u) |
| (1)-212 | (Ih) | (1r) | (2k) | (3p) | (4x) |
| (1)-213 | (Ih) | (1s) | (2m) | (3r) | (4y) |
| (1)-214 | (Ih) | (1x) | (2n) | (3t) | (4z) |
| (1)-215 | (Ih) | (1ii) | (2o) | (3o) | (4aa) |
| (1)-216 | (Ih) | (1jj) | (2p) | (3h) | (4bb) |
| (1)-217 | (Ih) | (1zz) | (2t) | (3o) | (4cc) |
| (1)-218 | (Ih) | (1bbb) | (2m) | (3p) | (4a) |
| (1)-219 | (Ih) | (1kkk) | (2a) | (3r) | (4c) |
| (1)-220 | (Ih) | (1b) | (2c) | (3t) | (4i) |
| (1)-221 | (Ih) | (1g) | (2d) | (3u) | (4j) |
| (1)-222 | (Ih) | (1h) | (2f) | (3x) | (4l) |
| (1)-223 | (Ih) | (1i) | (2a) | (3o) | (4u) |
| (1)-224 | (Ih) | (1i) | (2c) | (3p) | (4x) |
| (1)-225 | (Ih) | (1p) | (2d) | (3r) | (4y) |
| (1)-226 | (Ih) | (1r) | (2f) | (3t) | (4z) |
| (1)-227 | (Ih) | (1s) | (2h) | (3o) | (4aa) |
| (1)-228 | (Ih) | (1a) | (2k) | (3g) | (4bb) |
| (1)-229 | (Ih) | (1b) | (2m) | (3h) | (4cc) |
| (1)-230 | (Ih) | (1g) | (2n) | (3o) | (4a) |
| (1)-231 | (Ih) | (1h) | (2o) | (3p) | (4c) |
| (1)-232 | (Ih) | (1i) | (2p) | (3r) | (4i) |
| (1)-233 | (Ih) | (1a) | (2t) | (3t) | (4j) |
| (1)-234 | (Ih) | (1b) | (2h) | (3u) | (4l) |
| (1)-235 | (Ih) | (1g) | (2a) | (3x) | (4u) |
| (1)-236 | (Ih) | (1h) | (2c) | (3o) | (4x) |
| (1)-237 | (Ih) | (1i) | (2d) | (3p) | (4y) |
| (1)-238 | (Ih) | (1p) | (2f) | (3r) | (4z) |
| (1)-239 | (Ih) | (1r) | (2h) | (3t) | (4aa) |
| (1)-240 | (Ih) | (1s) | (2k) | (3o) | (4bb) |
| (1)-241 | (Ih) | (1x) | (2m) | (3a) | (4cc) |
| (1)-242 | (Ih) | (1ii) | (2n) | (3c) | (4u) |
| (1)-243 | (Ih) | (1jj) | (2o) | (3g) | (4x) |
| (1)-244 | (Ih) | (1zz) | (2p) | (3h) | (4y) |
| (1)-245 | (Ih) | (1bbb) | (2t) | (3o) | (4z) |
| (1)-246 | (Ii) | (1kkk) | (2h) | (3p) | (4aa) |
| (1)-247 | (Ii) | (1b) | (2a) | (3r) | (4bb) |
| (1)-248 | (Ii) | (1g) | (2c) | (3t) | (4cc) |
| (1)-249 | (Ii) | (1h) | (2d) | (3u) | (4u) |
| (1)-250 | (Ii) | (1i) | (2f) | (3x) | (4x) |
| (1)-251 | (Ii) | (1p) | (2h) | (3o) | (4y) |
| (1)-252 | (Ii) | (1r) | (2k) | (3p) | (4z) |
| (1)-253 | (Ii) | (1s) | (2m) | (3r) | (4c) |
| (1)-254 | (Ii) | (1x) | (2n) | (3t) | (4i) |
| (1)-255 | (Ii) | (1ii) | (2o) | (3o) | (4j) |
| (1)-256 | (Ii) | (1jj) | (2p) | (3a) | (4l) |
| (1)-257 | (Ii) | (1zz) | (2t) | (3c) | (4u) |
| (1)-258 | (Ii) | (1bbb) | (2m) | (3g) | (4x) |
| (1)-259 | (Ii) | (1kkk) | (2a) | (3h) | (4y) |
| (1)-260 | (Ii) | (1h) | (2c) | (3g) | (4z) |
| (1)-261 | (Ii) | (1i) | (2d) | (3h) | (4aa) |
| (1)-262 | (Ii) | (1p) | (2f) | (3o) | (4bb) |
| (1)-263 | (Ii) | (1r) | (2c) | (3p) | (4cc) |
| (1)-264 | (Ij) | (1s) | (2d) | (3r) | (4u) |
| (1)-265 | (Ij) | (1b) | (2f) | (3t) | (4u) |
| (1)-266 | (Ij) | (1g) | (2h) | (3u) | (4x) |
| (1)-267 | (Ij) | (1h) | (2k) | (3x) | (4y) |
| (1)-268 | (Ij) | (1i) | (2m) | (3a) | (4z) |
| (1)-269 | (Ij) | (1p) | (2n) | (3c) | (4a) |
| (1)-270 | (Ij) | (1r) | (2o) | (3g) | (4c) |
| (1)-271 | (Ij) | (1s) | (2p) | (3h) | (4i) |
| (1)-272 | (Ij) | (1x) | (2t) | (3a) | (4j) |
| (1)-273 | (Ij) | (1ii) | (2m) | (3c) | (4l) |
| (1)-274 | (Ij) | (1jj) | (2a) | (3g) | (4u) |
| (1)-275 | (Ij) | (1zz) | (2c) | (3h) | (4x) |
| (1)-276 | (Ij) | (1bbb) | (2d) | (3g) | (4y) |
| (1)-277 | (Ij) | (1kkk) | (2f) | (3h) | (4z) |
| (1)-278 | (Ij) | (1h) | (2d) | (3o) | (4aa) |
| (1)-279 | (Ij) | (1i) | (2f) | (3p) | (4bb) |
| (1)-280 | (Ij) | (1p) | (2h) | (3r) | (4cc) |
| (1)-281 | (Ij) | (1r) | (2k) | (3t) | (4a) |
| (1)-282 | (Ij) | (1s) | (2m) | (3u) | (4c) |
| (1)-283 | (Ik) | (1a) | (2n) | (3x) | (4i) |
| (1)-284 | (Ik) | (1b) | (2o) | (3a) | (4j) |
| (1)-285 | (Ik) | (1g) | (2p) | (3c) | (4l) |
| (1)-286 | (Ik) | (1h) | (2t) | (3g) | (4u) |
| (1)-287 | (Ik) | (1i) | (2a) | (3h) | (4a) |
| (1)-288 | (Ik) | (1p) | (2c) | (3o) | (4c) |
| (1)-289 | (Ik) | (1r) | (2d) | (3p) | (4a) |
| (1)-290 | (Ik) | (1s) | (2f) | (3r) | (4c) |
| (1)-291 | (Ik) | (1x) | (2h) | (3t) | (4i) |
| (1)-292 | (Ik) | (1ii) | (2k) | (3u) | (4j) |
| (1)-293 | (Ik) | (1jj) | (2m) | (3x) | (4l) |
| (1)-294 | (Ik) | (1zz) | (2n) | (3g) | (4u) |
| (1)-295 | (Ik) | (1bbb) | (2o) | (3h) | (4x) |
| (1)-296 | (Ik) | (1kkk) | (2p) | (3o) | (4y) |
| (1)-297 | (Ik) | (1a) | (2t) | (3p) | (4z) |
| (1)-298 | (Ik) | (1b) | (2m) | (3r) | (4aa) |
| (1)-299 | (Ik) | (1g) | (2a) | (3t) | (4bb) |
| (1)-300 | (Ik) | (1h) | (2c) | (3u) | (4cc) |

In some embodiments, the compound of formulae (I), (Ia)-(Ig) is one of the following compounds (or a pharmaceutically acceptable salt, prodrug, or N-oxide thereof, or a solvate or hydrate thereof) in Table 1:

TABLE 1

| No. | Structure | Name |
|---|---|---|
| 1 | 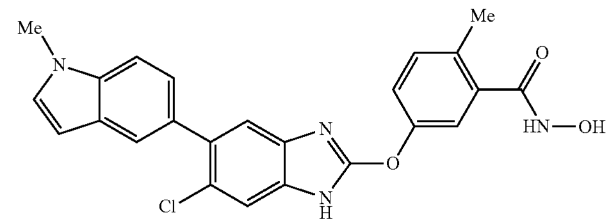 [SMILES: Cc1ccc(Oc2nc3cc(-c4ccc5c(ccn5C)c4)c(Cl)cc3[nH]2)cc1C(=O)NO] | 5-((6-chloro-5-(1-methyl-1H-indol-5-yl)-1H-benzo[d]imidazol-2-yl)oxy)-N-hydroxy-2-methylbenzamide; |
| 2 | 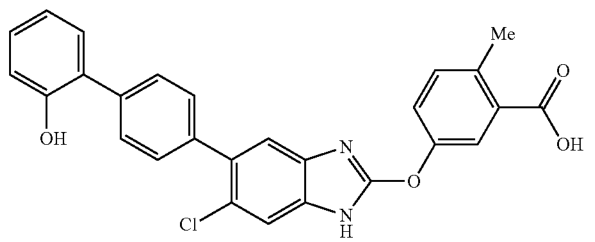 [SMILES: Cc1ccc(Oc2nc3cc(-c4ccc(-c5ccccc5O)cc4)c(Cl)cc3[nH]2)cc1C(=O)O] | 5-((6-chloro-5-(2'-hydroxy-[1,1'-biphenyl]-4-yl)-1H-benzo[d]imidazol-2-yl)oxy)-2-methylbenzonic acid; |
| 3 | 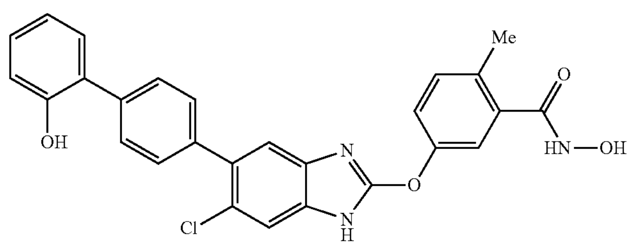 [SMILES: Cc1ccc(Oc2nc3cc(-c4ccc(-c5ccccc5O)cc4)c(Cl)cc3[nH]2)cc1C(=O)NO] | 5-((6-chloro-5-(2'-hydroxy-[1,1'-biphenyl]-4-yl)-1H-benzo[d]imidazol-2-yl)oxy)-N-hydroxy-2-methylbenzamide; |
| 4 | 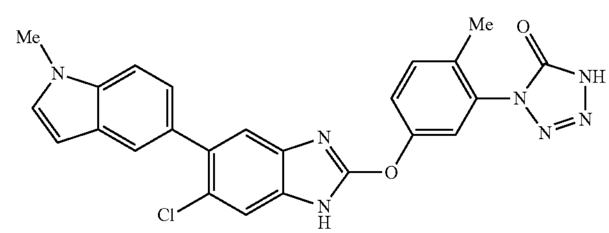 [SMILES: Cc1ccc(Oc2nc3cc(-c4ccc5c(ccn5C)c4)c(Cl)cc3[nH]2)cc1-n1nn[nH]c1=O] | 1-(5-((6-chloro-5-(1-methyl-1H-indol-5-yl)-1H-benzo[d]imidazol-2-yl)oxy)-2-methylphenyl)-1,4-dihydro-5H-tetrazol-5-one; |
| 5 | 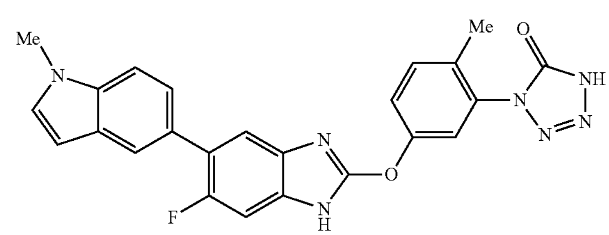 [SMILES: Cc1ccc(Oc2nc3cc(-c4ccc5c(ccn5C)c4)c(F)cc3[nH]2)cc1-n1nn[nH]c1=O] | 1-(5-((6-fluoro-5-(1-methyl-1H-indol-5-yl)-1H-benzo[d]imidazol-2-yl)oxy)-2-methylphenyl)-1,4-dihydro-5H-tetrazol-5-one; |
| 6 | 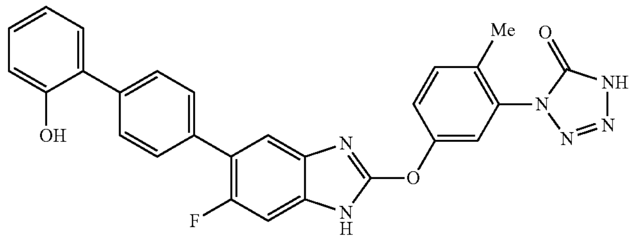 [SMILES: Cc1ccc(Oc2nc3cc(-c4ccc(-c5ccccc5O)cc4)c(F)cc3[nH]2)cc1-n1nn[nH]c1=O] | 1-(5-((6-fluoro-5-(2'-hydroxy-[1,1'-biphenyl]-4-yl)-1H-benzo[d]imidazol-2-yl)oxy)-2-methylphenyl)-1,4-dihydro-5H-tetrazol-5-one; |

TABLE 1-continued

| No. | Structure | Name |
|---|---|---|
| 7 | 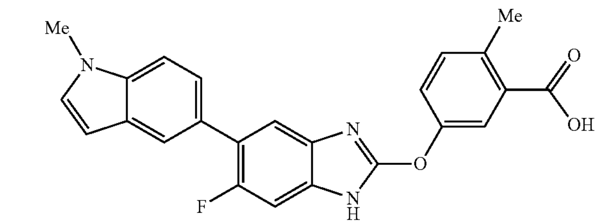 [SMILES: Cc1ccc(Oc2nc3cc(-c4ccc5c(ccn5C)c4)c(F)cc3[nH]2)cc1C(=O)O] | 5-((6-fluoro-5-(1-methyl-1H-indol-5-yl)-1H-benzo[d]imidazol-2-yl)oxy)-2-methylbenzoic acid |
| 8 | 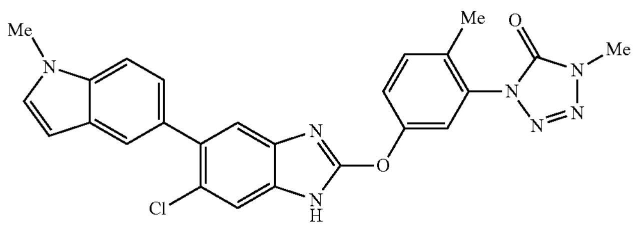 [SMILES: Cc1ccc(Oc2nc3cc(-c4ccc5c(ccn5C)c4)c(Cl)cc3[nH]2)cc1-n1nnn(C)c1=O] | 1-(5-((6-chloro-5-(1-methyl-1H-indol-5-yl)-1H-benzo[d]imidazol-2-yl)oxy)-2-methylphenyl)-4-methyl-1,4-dihydro-5H-tetrazol-5-one |
| 9 | 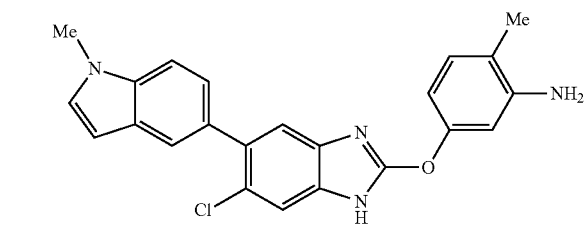 [SMILES: Cc1ccc(Oc2nc3cc(-c4ccc5c(ccn5C)c4)c(Cl)cc3[nH]2)cc1N] | 5-((6-chloro-5-(1-methyl-1H-indol-5-yl)-1H-benzo[d]imidazol-2-yl)oxy)-2-methylaniline |
| 10 | 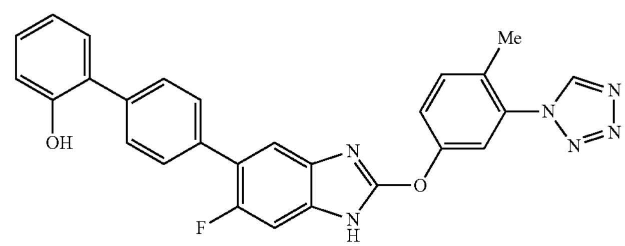 [SMILES: Cc1ccc(Oc2nc3cc(-c4ccc(-c5ccccc5O)cc4)c(F)cc3[nH]2)cc1-n1cnnn1] | 4'-(6-fluoro-2-(4-methyl-3-(1H-tetrazol-1-yl)phenoxy)-1H-benzo[d]imidazol-5-yl)-[1,1'-biphenyl]-2-ol |
| 11 | 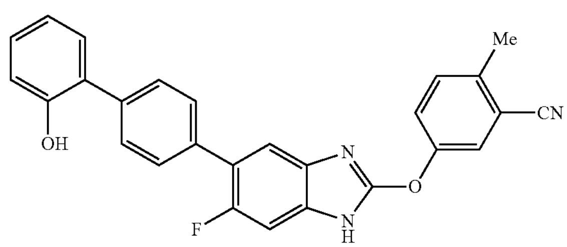 [SMILES: Cc1ccc(Oc2nc3cc(-c4ccc(-c5ccccc5O)cc4)c(F)cc3[nH]2)cc1C#N] | 5-((6-fluoro-5-(2'-hydroxy-[1,1'-biphenyl]-4-yl)-1H-benzo[d]imidazol-2-yl)oxy)-2-methylbenzonitrile |
| 12 | 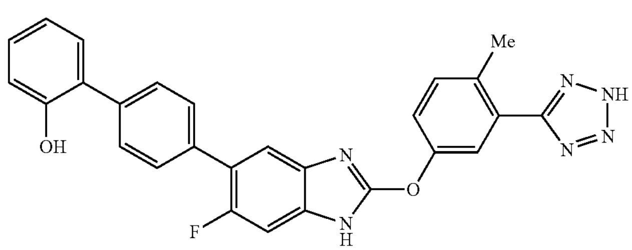 [SMILES: Cc1ccc(Oc2nc3cc(-c4ccc(-c5ccccc5O)cc4)c(F)cc3[nH]2)cc1-c1nn[nH]n1] | 4'-(6-fluoro-2-(4-methyl-3-(2H-tetrazol-5-yl)phenoxy)-1H-benzo[d]imidazol-5-yl)-[1,1'-biphenyl]-2-ol |

TABLE 1-continued

| No. | Structure | Name |
|---|---|---|
| 13 | 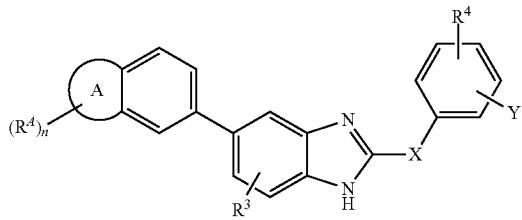 | 1-(5-((6-fluoro-5-(2'-hydroxy-[1,1'-biphenyl]-4-yl)-1H-benzo[d]imidazol-2-yl)oxy)-2-methylphenyl)-4-methyl-1,4-dihydro-5H-tetrazol-5-one |

In embodiment $II_1$ of this aspect, the invention comprises compounds having the structure of formula (II):

(II)

or a pharmaceutically acceptable salt, prodrug or N-oxide thereof, or solvate or hydrate thereof,
wherein
ring A is a 5- or 6-membered Het;
each $R^A$ is independently $C_{3-8}Cak(C_{0-6}alkyl)$, $Hca(C_{0-6}alkyl)$, $Ar(C_{0-6}alkyl)$, Het $(C_{0-6}alkyl)$, —O—$C_{0-6}alkyl$-$C_{3-8}Cak$, —O—$C_{0-6}alkyl$-Hca, —O—$C_{0-6}alkyl$-Ar, —O—$C_{0-6}alkyl$-Het, halogen, cyano, $C_{1-6}alkyl$, $C_{1-6}haloalkyl$, —$C_1$-$C_6alkoxy$, —OR, —SR, —$NR_2$, —C(O)R, —C(O)OR, —$C(O)NR_2$, —$S(O)_2NR_2$, —$S(O)_2R$, —OC(O)R, —N(R)C(O)R, —OC(O)OR, —$OC(O)NR_2$, —N(R)C(O)OR, —$N(R)C(O)NR_2$, —$N(R)S(O)_2R$, —$OP(O)(OR)_2$, wherein each Ar, Het, Cak, Hca, alkyl, alkoxy and haloalkyl group is optionally substituted by one or two -$R^{Ax}$ groups,
wherein each -$R^{Ax}$ is independently halogen, cyano, $C_{1-6}alkyl$, $C_{1-6}haloalkyl$, —$C_1$-$C_6alkoxy$, —OR, —SR, —$NR_2$, —C(O)R, —C(O)OR, —$C(O)NR_2$, —$S(O)_2NR_2$, —$S(O)_2R$, —OC(O)R, —N(R)C(O)R, —OC(O)OR, —$OC(O)NR_2$, —N(R)C(O)OR, —$N(R)C(O)NR_2$, —$N(R)S(O)_2R$, —$OP(O)(OR)_2$ or —$CH_2$—OP(O)(OR);
$R^3$ and $R^4$ are independently hydrogen, halogen, cyano, $C_{1-6}alkyl$, $C_{1-6}haloalkyl$, —$C_1$-$C_6alkoxy$, —OR, —SR, —$NR_2$, —C(O)R, —C(O)OR, —$C(O)NR_2$, —$S(O)_2NR_2$, —$S(O)_2R$, —OC(O)R, —N(R)C(O)R, —OC(O)OR, —$OC(O)NR_2$, —N(R)C(O)OR, —$N(R)C(O)NR_2$, —$N(R)S(O)_2R$, —$OP(O)(OR)_2$ or —$CH_2$—OP(O)(OR);
X is —O—, —S—, —NR— or —$CF_2$—;
Y is —$NR_2$, —CN, —$C(O)OR^Y$, —C(O)NHOH,

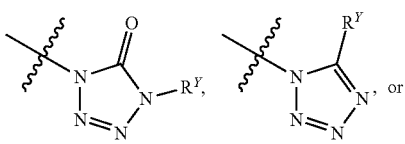

-continued

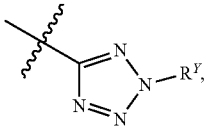

wherein $R^Y$ is hydrogen or $C_{1-6}alkyl$; and
each R is independently hydrogen, $C_1$-$C_6alkyl$, $C_1$-$C_6haloalkyl$, —$(C_0$-$C_6alkyl)$-Ar, —$(C_0$-$C_6alkyl)$-Het, —$(C_0$-$C_6alkyl)$-Cak, or —$(C_0$-$C_6alkyl)$-Hca, wherein Ar, Het, Cak, Hca, alkyl, and haloalkyl are optionally substituted with $C_1$-$C_6alkyl$, halogen, $C_1$-$C_6haloalkyl$ or cyano; and
n is 1, 2, 3 or 4.
In embodiment $II_2$ of this aspect, the invention comprises compounds of embodiment $II_1$, wherein
ring A is pyridyl, pyrimidinyl, pyrazinyl, pyridazinyl, pyrrolyl, furanyl, thiophenyl, pyrazolyl, imidazolyl, isoxazolyl, oxazolyl, isothiazolyl or thiazolyl.
In embodiment $II_3$, the compounds are of any of embodiments $I_1$ or $I_2$, or a pharmaceutically acceptable salt, prodrug, or N-oxide thereof, or a solvate or hydrate thereof, wherein
each $R^A$ is independently halogen, cyano, $C_{1-6}alkyl$, $C_{1-6}haloalkyl$, —$C_1$-$C_6alkoxy$, —OR, —SR, —$NR_2$, —C(O)R, —C(O)OR, —$C(O)NR_2$, —$S(O)_2NR_2$, —$S(O)_2R$, —OC(O)R, —N(R)C(O)R, —OC(O)OR, —$OC(O)NR_2$, —N(R)C(O)OR, —$N(R)C(O)NR_2$, —$N(R)S(O)_2R$, —$OP(O)(OR)_2$ or —$CH_2$—OP(O)(OR), wherein each alkyl, alkoxy and haloalkyl group is optionally substituted by one or two -$R^{Ax}$ groups,
wherein each -$R^{Ax}$ is independently halogen, cyano, $C_{1-6}alkyl$, $C_{1-6}haloalkyl$, —$C_1$-$C_6alkoxy$, —OR, —SR, —$NR_2$, —C(O)R, —C(O)OR, —$C(O)NR_2$, —$S(O)_2NR_2$, —$S(O)_2R$, —OC(O)R, —N(R)C(O)R, —OC(O)OR, —$OC(O)NR_2$, —N(R)C(O)OR, —$N(R)C(O)NR_2$, —$N(R)S(O)_2R$, —$OP(O)(OR)_2$ or —$CH_2$—OP(O)(OR).
In embodiment $II_4$, the compounds are of any of embodiments $II_1$-$I_3$, or a pharmaceutically acceptable salt, prodrug, or N-oxide thereof, or a solvate or hydrate thereof, wherein
X is —O—.
In embodiment $II_5$, the compounds are of any of embodiments $II_1$-$I_4$, or a pharmaceutically acceptable salt, prodrug, or N-oxide thereof, or a solvate or hydrate thereof, wherein
each R is independently hydrogen, $C_1$-$C_6alkyl$ or $C_1$-$C_6haloalkyl$.
In embodiment $II_6$, the compounds of the invention are one of formulae (IIa)-(IIg), wherein $R^3$, $R^4$, X, Y, $R^a$ and n are as defined in any of embodiments $II_1$-$II_5$ above:

Structural Formula (II) is One of Formulae (IIa)-(IIg):

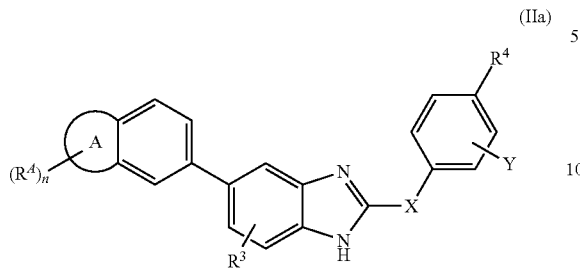
(IIa)

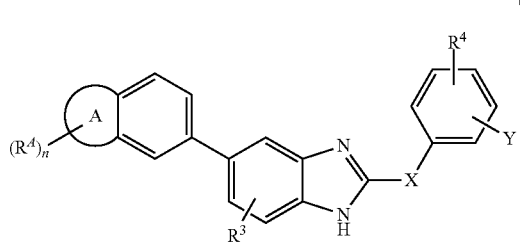
(IIb)

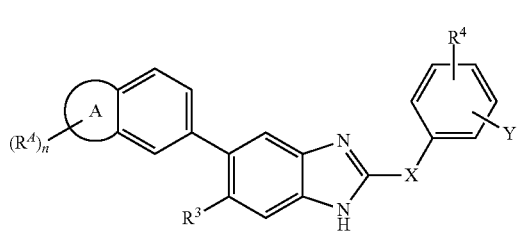
(IIc)

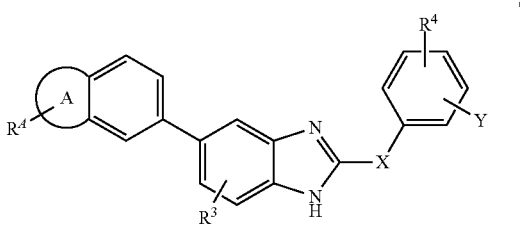
(IId)

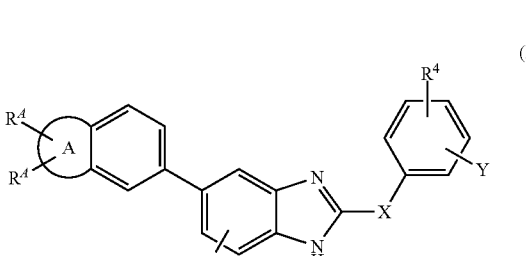
(IIe)

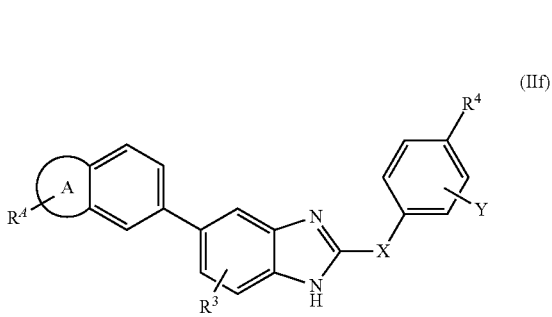
(IIf)

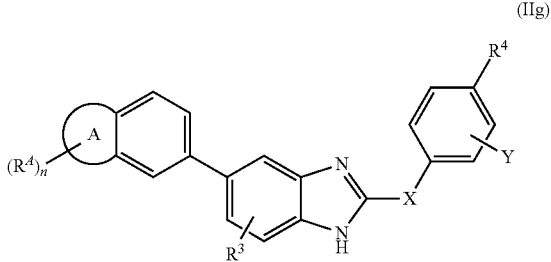
(IIg)

Particular embodiments of this aspect of the invention comprise compounds of any one of the formulae (II), and (IIa)-(IIg), each as defined in each of the following rows (or a pharmaceutically acceptable salt, prodrug, or N-oxide thereof, or a solvate or hydrate thereof), wherein each entry is a group number as defined above (e.g., (3y) refers to $R^1$ is —OR, and a dash "-" indicates that the variable is as defined in embodiment hi or defined according to any one of the applicable variable definitions (1a)-(1uuu), (2a)-(2oo), (3a)-(3mm) and (4a)-(4cc) [e.g., when $R^1$ is a dash, it can be either as defined in any of embodiments $II_1$-$II_6$ or any one of the applicable definitions (1a)-(1uuu)]:

|  | (II) | A | $R^3$ | $R^4$ | Y |
|---|---|---|---|---|---|
| (2)-1 | (IIa) | (1a) | (2a) | (3a) | (4a) |
| (2)-2 | (IIa) | (1b) | (2c) | (3c) | (4c) |
| (2)-3 | (IIa) | (1c) | (2d) | (3g) | (4i) |
| (2)-4 | (IIa) | (1d) | (2f) | (3h) | (4j) |
| (2)-5 | (IIa) | (1l) | (2h) | (3o) | (4l) |
| (2)-6 | (IIa) | (1m) | (2k) | (3p) | (4u) |
| (2)-7 | (IIa) | (1g) | (2m) | (3r) | (4x) |
| (2)-8 | (IIa) | (1h) | (2n) | (3t) | (4y) |
| (2)-9 | (IIa) | (1e) | (2o) | (3u) | (4z) |
| (2)-10 | (IIa) | (1f) | (2p) | (3x) | (4aa) |
| (2)-11 | (IIa) | (1g) | (2t) | (3g) | (4bb) |
| (2)-12 | (IIa) | (1h) | (2d) | (3h) | (4cc) |
| (2)-13 | (IIa) | (1i) | (2f) | (3o) | (4a) |
| (2)-14 | (IIa) | (1j) | (2h) | (3p) | (4c) |
| (2)-15 | (IIa) | (1a) | (2p) | (3t) | (4u) |
| (2)-16 | (IIa) | (1b) | (2t) | (3x) | (4x) |
| (2)-17 | (IIa) | (1c) | (2d) | (3g) | (4y) |
| (2)-18 | (IIa) | (1d) | (2a) | (3a) | (4z) |
| (2)-19 | (IIa) | (1l) | (2c) | (3c) | (4aa) |
| (2)-20 | (IIa) | (1m) | (2d) | (3g) | (4bb) |
| (2)-21 | (IIa) | (1g) | (2d) | (3p) | (4a) |
| (2)-22 | (IIa) | (1h) | (2f) | (3r) | (4c) |
| (2)-23 | (IIa) | (1a) | (2h) | (3c) | (4j) |
| (2)-24 | (IIa) | (1b) | (2a) | (3g) | (4l) |
| (2)-25 | (IIa) | (1c) | (2c) | (3h) | (4a) |
| (2)-26 | (IIa) | (1d) | (2d) | (3o) | (4c) |
| (2)-27 | (IIa) | (1l) | (2f) | (3p) | (4i) |
| (2)-28 | (IIa) | (1m) | (2a) | (3t) | (4j) |
| (2)-29 | (IIa) | (1g) | (2c) | (3r) | (4l) |
| (2)-30 | (IIb) | (1h) | (2d) | (3a) | (4a) |
| (2)-31 | (IIb) | (1b) | (2c) | (3c) | (4c) |
| (2)-32 | (IIb) | (1c) | (2d) | (3g) | (4i) |
| (2)-33 | (IIb) | (1d) | (2f) | (3h) | (4j) |
| (2)-34 | (IIb) | (1l) | (2h) | (3o) | (4l) |
| (2)-35 | (IIb) | (1m) | (2k) | (3p) | (4u) |
| (2)-36 | (IIb) | (1g) | (2m) | (3r) | (4x) |
| (2)-37 | (IIb) | (1h) | (2n) | (3t) | (4y) |
| (2)-38 | (IIb) | (1e) | (2o) | (3u) | (4z) |
| (2)-39 | (IIb) | (1f) | (2p) | (3x) | (4aa) |
| (2)-40 | (IIb) | (1g) | (2t) | (3g) | (4bb) |
| (2)-41 | (IIb) | (1h) | (2d) | (3h) | (4cc) |
| (2)-42 | (IIb) | (1i) | (2f) | (3o) | (4a) |
| (2)-43 | (IIb) | (1j) | (2h) | (3p) | (4c) |
| (2)-44 | (IIb) | (1a) | (2p) | (3x) | (4i) |
| (2)-45 | (IIb) | (1b) | (2t) | (3g) | (4j) |
| (2)-46 | (IIb) | (1c) | (2d) | (3a) | (4l) |
| (2)-47 | (IIb) | (1d) | (2d) | (3c) | (4a) |

|  | (II) | A | R³ | R⁴ | Y |
|---|---|---|---|---|---|
| (2)-48 | (IIb) | (1l) | (2f) | (3g) | (4c) |
| (2)-49 | (IIb) | (1m) | (2h) | (3p) | (4u) |
| (2)-50 | (IIb) | (1g) | (2a) | (3r) | (4x) |
| (2)-51 | (IIb) | (1h) | (2c) | (3c) | (4y) |
| (2)-52 | (IIb) | (1a) | (2d) | (3g) | (4z) |
| (2)-53 | (IIb) | (1b) | (2d) | (3h) | (4aa) |
| (2)-54 | (IIb) | (1c) | (2a) | (3o) | (4bb) |
| (2)-55 | (IIb) | (1d) | (2c) | (3p) | (4i) |
| (2)-56 | (IIb) | (1l) | (2d) | (3t) | (4j) |
| (2)-57 | (IIb) | (1m) | (2f) | (3r) | (4l) |
| (2)-58 | (IIb) | (1g) | (2a) | (3r) | (4u) |
| (2)-59 | (IIc) | (1h) | (2c) | (3a) | (4x) |
| (2)-60 | (IIc) | (1b) | (2d) | (3c) | (4y) |
| (2)-61 | (IIc) | (1c) | (2d) | (3g) | (4z) |
| (2)-62 | (IIc) | (1d) | (2f) | (3h) | (4aa) |
| (2)-63 | (IIc) | (1l) | (2h) | (3o) | (4bb) |
| (2)-64 | (IIc) | (1m) | (2k) | (3p) | (4u) |
| (2)-65 | (IIc) | (1g) | (2m) | (3r) | (4x) |
| (2)-66 | (IIc) | (1h) | (2n) | (3t) | (4y) |
| (2)-67 | (IIc) | (1e) | (2o) | (3u) | (4z) |
| (2)-68 | (IIc) | (1f) | (2p) | (3x) | (4aa) |
| (2)-69 | (IIc) | (1g) | (2t) | (3g) | (4bb) |
| (2)-70 | (IIc) | (1h) | (2d) | (3h) | (4cc) |
| (2)-71 | (IIe) | (1i) | (2f) | (3o) | (4a) |
| (2)-72 | (IIe) | (1j) | (2h) | (3p) | (4c) |
| (2)-73 | (IIe) | (1a) | (2a) | (3p) | (4i) |
| (2)-74 | (IIe) | (1b) | (2c) | (3r) | (4j) |
| (2)-75 | (IIe) | (1c) | (2d) | (3c) | (4l) |
| (2)-76 | (IIe) | (1d) | (2a) | (3p) | (4a) |
| (2)-77 | (IIe) | (1l) | (2c) | (3r) | (4c) |
| (2)-78 | (IIe) | (1m) | (2d) | (3c) | (4c) |
| (2)-79 | (IIe) | (1g) | (2t) | (3h) | (4u) |
| (2)-80 | (IIe) | (1h) | (2d) | (3a) | (4x) |
| (2)-81 | (IIe) | (1a) | (2f) | (3e) | (4y) |
| (2)-82 | (IIe) | (1b) | (2p) | (3g) | (4z) |
| (2)-83 | (IIe) | (1c) | (20) | (3p) | (4aa) |
| (2)-84 | (IIc) | (1d) | (2d) | (3r) | (4bb) |
| (2)-85 | (IIc) | (1l) | (2a) | (3c) | (4a) |
| (2)-86 | (IIc) | (1m) | (2c) | (3h) | (4c) |
| (2)-87 | (IIc) | (1g) | (2d) | (3o) | (4j) |
| (2)-88 | (IIc) | (1h) | (2f) | (3p) | (4l) |
| (2)-89 | (IId) | (1a) | (2a) | (3t) | (4a) |
| (2)-90 | (IId) | (1b) | (2c) | (3c) | (4c) |
| (2)-91 | (IId) | (1c) | (2d) | (3g) | (4i) |
| (2)-92 | (IId) | (1d) | (2f) | (3h) | (4j) |
| (2)-93 | (IId) | (1l) | (2h) | (3o) | (4l) |
| (2)-94 | (IId) | (1m) | (2k) | (3p) | (4u) |
| (2)-95 | (IId) | (1g) | (2m) | (3r) | (4x) |
| (2)-96 | (IId) | (1h) | (2n) | (3t) | (4y) |
| (2)-97 | (IId) | (1e) | (2o) | (3u) | (4z) |
| (2)-98 | (IId) | (1f) | (2p) | (3x) | (4aa) |
| (2)-99 | (IId) | (1g) | (2t) | (3g) | (4bb) |
| (2)-100 | (IId) | (1h) | (2d) | (3h) | (4cc) |
| (2)-101 | (IId) | (1i) | (2f) | (3o) | (4a) |
| (2)-102 | (IId) | (1j) | (2h) | (3p) | (4c) |
| (2)-103 | (IId) | (1a) | (2a) | (3r) | (4a) |
| (2)-104 | (IId) | (1b) | (2c) | (3e) | (4c) |
| (2)-105 | (IId) | (1c) | (2d) | (3h) | (4y) |
| (2)-106 | (IId) | (1d) | (2d) | (3g) | (4z) |
| (2)-107 | (IId) | (1l) | (2f) | (3a) | (4aa) |
| (2)-108 | (IId) | (1m) | (2a) | (3e) | (4c) |
| (2)-109 | (IId) | (1g) | (2c) | (3g) | (4u) |
| (2)-110 | (IId) | (1h) | (2d) | (3p) | (4x) |
| (2)-111 | (IId) | (1a) | (2f) | (3r) | (4u) |
| (2)-112 | (IId) | (1b) | (2h) | (3c) | (4x) |
| (2)-113 | (IId) | (1c) | (2p) | (3g) | (4y) |
| (2)-114 | (IId) | (1d) | (2t) | (3h) | (4z) |
| (2)-115 | (IId) | (1l) | (2d) | (3o) | (4aa) |
| (2)-116 | (IId) | (1m) | (2a) | (3p) | (4c) |
| (2)-117 | (IId) | (1g) | (2c) | (3t) | (4u) |
| (2)-118 | (IIe) | (1h) | (2d) | (3a) | (4x) |
| (2)-119 | (IIe) | (1b) | (2c) | (3c) | (4c) |
| (2)-120 | (IIe) | (1c) | (2d) | (3g) | (4i) |
| (2)-121 | (IIe) | (1d) | (2f) | (3h) | (4j) |
| (2)-122 | (IIe) | (1l) | (2h) | (3o) | (4l) |
| (2)-123 | (IIe) | (1m) | (2k) | (3p) | (4u) |
| (2)-124 | (IIe) | (1g) | (2m) | (3r) | (4x) |
| (2)-125 | (IIe) | (1h) | (2n) | (3t) | (4y) |
| (2)-126 | (IIe) | (1e) | (2o) | (3u) | (4z) |
| (2)-127 | (IIe) | (1f) | (2p) | (3x) | (4aa) |
| (2)-128 | (IIe) | (1g) | (2t) | (3g) | (4bb) |
| (2)-129 | (IIe) | (1h) | (2d) | (3h) | (4cc) |
| (2)-130 | (IIe) | (1i) | (2f) | (3o) | (4a) |
| (2)-131 | (IIe) | (1j) | (2h) | (3p) | (4c) |
| (2)-132 | (IIe) | (1a) | (2p) | (3p) | (4a) |
| (2)-133 | (IIe) | (1b) | (2t) | (3r) | (4c) |
| (2)-134 | (IIe) | (1c) | (2d) | (3c) | (4a) |
| (2)-135 | (IIe) | (1d) | (2t) | (3h) | (4c) |
| (2)-136 | (IIe) | (1l) | (2d) | (3p) | (4u) |
| (2)-137 | (IIe) | (1m) | (2f) | (3t) | (4x) |
| (2)-138 | (IIe) | (1g) | (2h) | (3x) | (4y) |
| (2)-139 | (IIe) | (1h) | (2a) | (3g) | (4y) |
| (2)-140 | (IIe) | (1a) | (2c) | (3a) | (4z) |
| (2)-141 | (IIe) | (1b) | (2d) | (3c) | (4aa) |
| (2)-142 | (IIe) | (1c) | (2c) | (3g) | (4c) |
| (2)-143 | (IIe) | (1d) | (2d) | (3p) | (4u) |
| (2)-144 | (IIe) | (1l) | (2f) | (3r) | (4x) |
| (2)-145 | (IIe) | (1m) | (2p) | (3c) | (4c) |
| (2)-146 | (IIe) | (1g) | (2t) | (3g) | (4u) |
| (2)-147 | (IIf) | (1h) | (2d) | (3a) | (4x) |
| (2)-148 | (IIf) | (1b) | (2c) | (3c) | (4c) |
| (2)-149 | (IIf) | (1c) | (2d) | (3g) | (4i) |
| (2)-150 | (IIf) | (1d) | (2f) | (3h) | (4j) |
| (2)-151 | (IIf) | (1l) | (2h) | (3o) | (4l) |
| (2)-152 | (IIf) | (1m) | (2k) | (3p) | (4u) |
| (2)-153 | (IIf) | (1g) | (2m) | (3r) | (4x) |
| (2)-154 | (IIf) | (1h) | (2n) | (30) | (4y) |
| (2)-155 | (IIf) | (1e) | (2o) | (3u) | (4z) |
| (2)-156 | (IIf) | (1f) | (2p) | (3x) | (4aa) |
| (2)-157 | (IIf) | (1g) | (2t) | (3g) | (4bb) |
| (2)-158 | (IIf) | (1h) | (2d) | (3h) | (4cc) |
| (2)-159 | (IIf) | (1i) | (2f) | (3o) | (4a) |
| (2)-160 | (IIf) | (1j) | (2h) | (3p) | (4c) |
| (2)-161 | (IIf) | (1a) | (2a) | (3h) | (4x) |
| (2)-162 | (IIf) | (1b) | (2c) | (3o) | (4y) |
| (2)-163 | (IIf) | (1c) | (2d) | (3p) | (4bb) |
| (2)-164 | (IIf) | (1d) | (2a) | (3t) | (4c) |
| (2)-165 | (IIf) | (1l) | (2c) | (3g) | (4u) |
| (2)-166 | (IIf) | (1m) | (2d) | (3x) | (4x) |
| (2)-167 | (IIf) | (1g) | (2d) | (3g) | (4a) |
| (2)-168 | (IIf) | (1h) | (2p) | (3a) | (4c) |
| (2)-169 | (IIf) | (1a) | (2t) | (3c) | (4u) |
| (2)-170 | (IIf) | (1b) | (2d) | (3g) | (4x) |
| (2)-171 | (IIf) | (1c) | (2a) | (3p) | (4y) |
| (2)-172 | (IIf) | (1d) | (2c) | (3r) | (4z) |
| (2)-173 | (IIf) | (1l) | (2d) | (3c) | (4aa) |
| (2)-174 | (IIf) | (1m) | (2f) | (3g) | (4bb) |
| (2)-175 | (IIg) | (1g) | (2a) | (3a) | (4a) |
| (2)-176 | (IIg) | (1h) | (2c) | (3c) | (4c) |
| (2)-177 | (IIg) | (1c) | (2d) | (3g) | (4i) |
| (2)-178 | (IIg) | (1d) | (2f) | (3h) | (4j) |
| (2)-179 | (IIg) | (1l) | (2h) | (3o) | (4l) |
| (2)-180 | (IIg) | (1m) | (2k) | (3p) | (4u) |
| (2)-181 | (IIg) | (1g) | (2m) | (3r) | (4x) |
| (2)-182 | (IIg) | (1h) | (2n) | (3t) | (4y) |
| (2)-183 | (IIg) | (1e) | (2o) | (3u) | (4z) |
| (2)-184 | (IIg) | (1f) | (2p) | (3x) | (4aa) |
| (2)-185 | (IIg) | (1g) | (2t) | (3g) | (4bb) |
| (2)-186 | (IIg) | (1h) | (2d) | (3h) | (4cc) |
| (2)-187 | (IIg) | (1i) | (2f) | (3o) | (4a) |
| (2)-188 | (IIg) | (1j) | (2h) | (3p) | (4c) |
| (2)-189 | (IIg) | (1a) | (2p) | (3h) | (4bb) |
| (2)-190 | (IIg) | (1b) | (2t) | (3o) | (4x) |
| (2)-191 | (IIg) | (1c) | (2d) | (3p) | (4y) |
| (2)-192 | (IIg) | (1d) | (2t) | (3t) | (4a) |
| (2)-193 | (IIg) | (1l) | (2d) | (3g) | (4c) |
| (2)-194 | (IIg) | (1m) | (2a) | (3a) | (4u) |
| (2)-195 | (IIg) | (1g) | (2c) | (3c) | (4x) |
| (2)-196 | (IIg) | (1h) | (2d) | (3g) | (4y) |
| (2)-197 | (IIg) | (1a) | (2a) | (3p) | (4z) |
| (2)-198 | (IIg) | (1b) | (2c) | (3r) | (4c) |
| (2)-199 | (IIg) | (1c) | (2d) | (3c) | (4u) |
| (2)-200 | (IIg) | (1d) | (2f) | (3g) | (4x) |

In embodiment III₁ of this aspect, the invention comprises compounds having the structure of formula (III):

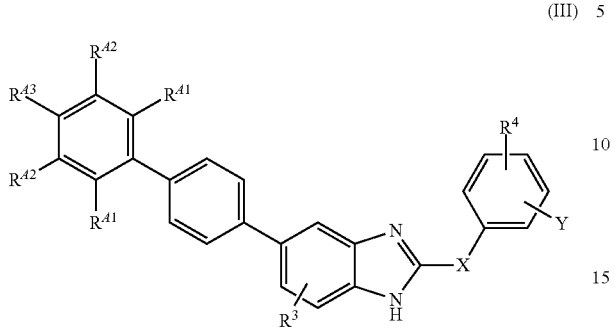

(III)

or a pharmaceutically acceptable salt, prodrug or N-oxide thereof, or solvate or hydrate thereof, wherein each $R^{A1}$ is independently hydrogen, $C_{3-8}$Cak($C_{0-6}$alkyl), Hca($C_{0-6}$alkyl), Ar($C_{0-6}$alkyl), Het($C_{0-6}$alkyl), —O—$C_{0-6}$alkyl-$C_{3-8}$Cak, —O—$C_{0-6}$alkyl-Hca, —O—$C_{0-6}$alkyl-Ar, —O—$C_{0-6}$alkyl-Het, cyano, $C_{1-6}$haloalkyl, —$C_1$-$C_6$alkoxy, —OR, —SR, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂ or —CH₂—OP(O)(OR);

each $R^{A2}$ is independently hydrogen, $C_{3-8}$Cak($C_{0-6}$alkyl), Hca($C_{0-6}$alkyl), Ar($C_{0-6}$alkyl), Het($C_{0-6}$alkyl), —O—$C_{0-6}$alkyl-$C_{3-8}$Cak, —O—$C_{0-6}$alkyl-Hca, —O—$C_{0-6}$alkyl-Ar, —O—$C_{0-6}$alkyl-Het, cyano, $C_{1-6}$alkyl, $C_{1-6}$haloalkyl, —$C_1$-$C_6$alkoxy, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂ or —CH₂—OP(O)(OR);

$R^{A3}$ is hydrogen, $C_{3-8}$Cak($C_{0-6}$alkyl), Hca($C_{0-6}$alkyl), Ar($C_{0-6}$alkyl), Het($C_{0-6}$alkyl), —O—$C_{0-6}$alkyl-$C_{3-8}$Cak, —O—$C_{0-6}$alkyl-Hca, —O—$C_{0-6}$alkyl-Ar, —O—$C_{0-6}$alkyl-Het, $C_{1-6}$alkyl, $C_{1-6}$haloalkyl, —$C_1$-$C_6$alkoxy, —SR, —NR₂, —C(O)R, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂ or —CH₂—OP(O)(OR);

wherein each Ar, Het, Cak, Hca, alkyl, alkoxy and haloalkyl group in each $R^{A1}$, $R^{A2}$ and $R^{A3}$ is optionally substituted by one or two -$R^{Ax}$ groups, wherein each -$R^{Ax}$ is independently halogen, cyano, $C_{1-6}$alkyl, $C_{1-6}$haloalkyl, —$C_1$-$C_6$alkoxy, —OR, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂ or —CH₂—OP(O)(OR);

$R^3$ is hydrogen, halogen, cyano, $C_{1-6}$alkyl, $C_{1-6}$haloalkyl, —$C_1$-$C_6$alkoxy, —OR, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂ or —CH₂—OP(O)(OR);

$R^4$ is halogen, cyano, $C_{1-6}$alkyl, $C_{1-6}$haloalkyl, —$C_1$-$C_6$alkoxy, —OR, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂ or —CH₂—OP(O)(OR);

X is —O—, —S—, —NR— or —CF₂—;
Y is —NR₂, —CN, —C(O)OR$^Y$, —C(O)NHOH,

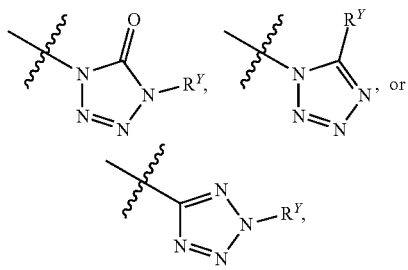

wherein R$^Y$ is hydrogen or $C_{1-6}$alkyl; and
each R is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano;
provided that
(a) at least one of $R^{A1}$, $R^{A2}$ or $R^{A3}$ is not hydrogen;
(b) when $R^{A1}$ or $R^{A5}$ is hydroxyl, $R^3$ is not fluoro; and
(c) when $R^{A1}$ or $R^{A5}$ is methoxy, $R^3$ is not chloro.

In embodiment III₂, the compounds are of embodiment III₁, or a pharmaceutically acceptable salt, prodrug, or N-oxide thereof, or a solvate or hydrate thereof, wherein each $R^{A1}$ is independently hydrogen, cyano, $C_{1-6}$haloalkyl, —$C_1$-$C_6$alkoxy, —OR, —SR, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂ or —CH₂—OP(O)(OR);

each $R^{A2}$ is independently hydrogen, cyano, $C_{1-6}$alkyl, $C_{1-6}$haloalkyl, —$C_1$-$C_6$alkoxy, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂ or —CH₂—OP(O)(OR);

$R^{A3}$ is hydrogen, $C_{1-6}$alkyl, $C_{1-6}$haloalkyl, —$C_1$-$C_6$alkoxy, —SR, —NR₂, —C(O)R, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂ or —CH₂—OP(O)(OR);

wherein each alkyl, alkoxy and haloalkyl group in each $R^{A1}$, $R^{A2}$ and $R^{A3}$ is optionally substituted by one or two -$R^{Ax}$ groups.

In embodiment III₃ of this aspect, the invention comprises compounds having the structure of formula (IIIa):

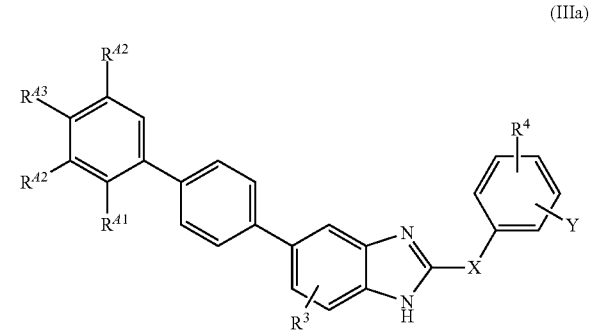

(IIIa)

or a pharmaceutically acceptable salt, prodrug or N-oxide thereof, or solvate or hydrate thereof, wherein $R^{A1}$ is $C_{3-8}$Cak($C_{0-6}$alkyl), Hca($C_{0-6}$alkyl), Ar($C_{0-6}$alkyl), Het($C_{0-6}$alkyl), —O—$C_{0-6}$alkyl-$C_{3-8}$Cak, —O—$C_{0-6}$alkyl-Hca, —O—$C_{0-6}$alkyl-Ar, —O—$C_{0-6}$alkyl-Het, cyano, $C_{1-6}$haloalkyl, —$C_1$-$C_6$alkoxy, —OH, —SR, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

each $R^{A2}$ group is independently hydrogen, $C_{3-8}$Cak($C_{0-6}$alkyl), Hca($C_{0-6}$alkyl), Ar ($C_{0-6}$alkyl), Het($C_{0-6}$alkyl), —O—$C_{0-6}$alkyl-$C_{3-8}$Cak, —O—$C_{0-6}$alkyl-Hca, —O—$C_{0-6}$alkyl-Ar, —O—$C_{0-6}$alkyl-Het, cyano, $C_{1-6}$alkyl, $C_{1-6}$haloalkyl, —$C_1$-$C_6$alkoxy, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

$R^{A3}$ is hydrogen, $C_{3-8}$Cak($C_{0-6}$alkyl), Hca($C_{0-6}$alkyl), Ar($C_{0-6}$alkyl), Het($C_{0-6}$alkyl), —O—$C_{0-6}$alkyl-$C_{3-8}$Cak, —O—$C_{0-6}$alkyl-Hca, —O—$C_{0-6}$alkyl-Ar, —O—$C_{0-6}$alkyl-Het, $C_{1-6}$alkyl, $C_{1-6}$haloalkyl, —$C_1$-$C_6$alkoxy, —SR, —NR$_2$, —C(O)R, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

wherein each Ar, Het, Cak, Hca, alkyl, alkoxy and haloalkyl group in each $R^{A1}$, $R^{A2}$ and $R^{A3}$ is optionally substituted by one or two -$R^{Ax}$ groups, wherein each -$R^{Ax}$ is independently halogen, cyano, $C_{1-6}$alkyl, $C_{1-6}$haloalkyl, —$C_1$-$C_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

$R^3$ is hydrogen, chloro, bromo, cyano, $C_{1-6}$alkyl, $C_{1-6}$haloalkyl, —$C_1$-$C_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

$R^4$ is halogen, cyano, $C_{1-6}$alkyl, $C_{1-6}$haloalkyl, —$C_1$-$C_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

X is —O—, —S—, —NR— or —CF$_2$—;

Y is, —NR$_2$, —CN, —C(O)OR, —C(O)NHOH,

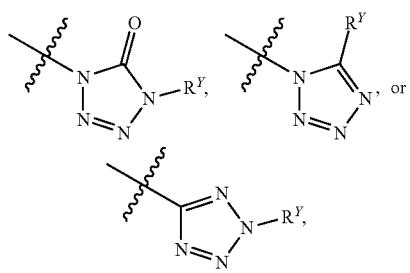

wherein $R^Y$ is hydrogen or $C_{1-6}$alkyl; and each R is independently hydrogen, $C_1$-$C_6$alkyl, $C_1$-$C_6$haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano.

In embodiment III$_4$, the compounds are of embodiment III$_3$, or a pharmaceutically acceptable salt, prodrug, or N-oxide thereof, or a solvate or hydrate thereof, wherein $R^{A1}$ is cyano, $C_{1-6}$haloalkyl, —$C_1$-$C_6$alkoxy, —OH, —SR, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

each $R^{A2}$ group is independently hydrogen, cyano, $C_{1-6}$alkyl, $C_{1-6}$haloalkyl, —$C_1$-$C_6$alkoxy, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

$R^{A3}$ is hydrogen, $C_{1-6}$alkyl, $C_{1-6}$haloalkyl, —$C_1$-$C_6$alkoxy, —SR, —NR$_2$, —C(O)R, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

wherein each alkyl, alkoxy and haloalkyl group in each $R^{A1}$, $R^{A2}$ and $R^{A3}$ is optionally substituted by one or two -$R^{Ax}$ groups.

In embodiment III$_5$, the compounds are of any of embodiments I$_1$-I$_4$, or a pharmaceutically acceptable salt, prodrug, or N-oxide thereof, or a solvate or hydrate thereof, wherein X is —O—.

In embodiment III$_6$, the compounds are of any of embodiments III$_1$-I$_5$, or a pharmaceutically acceptable salt, prodrug, or N-oxide thereof, or a solvate or hydrate thereof, wherein each R is independently hydrogen, $C_1$-$C_6$alkyl or $C_1$-$C_6$haloalkyl.

In embodiment III$_7$, the compounds of the invention are of one of formulae (IIIa)-(IIIk), wherein $R^{A1}$, $R^{A2}$, $R^{A3}$, $R^3$, $R^4$, X and Y are as defined in embodiment III above:

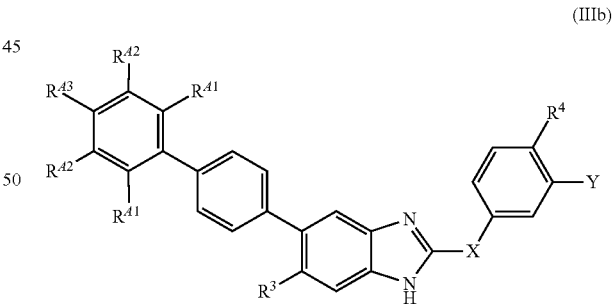

(IIIb)

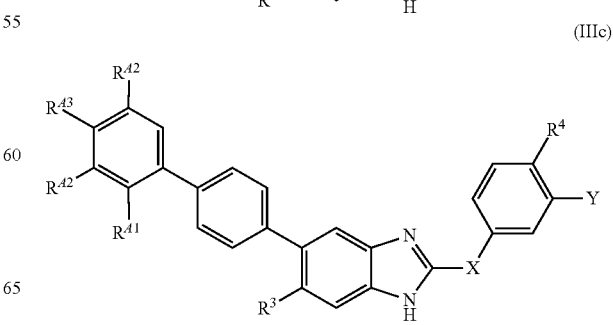

(IIIc)

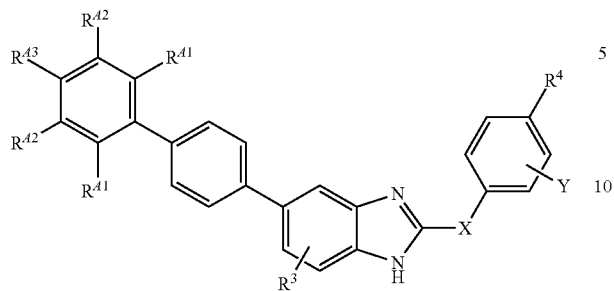

(IIId)

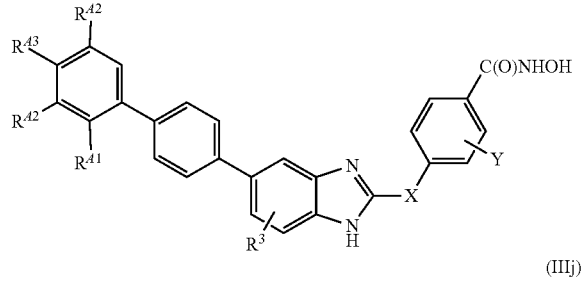

(IIIi)

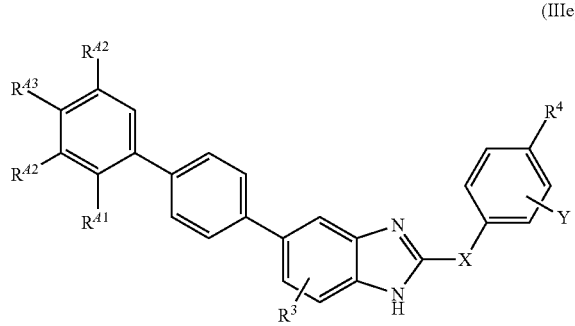

(IIIe)

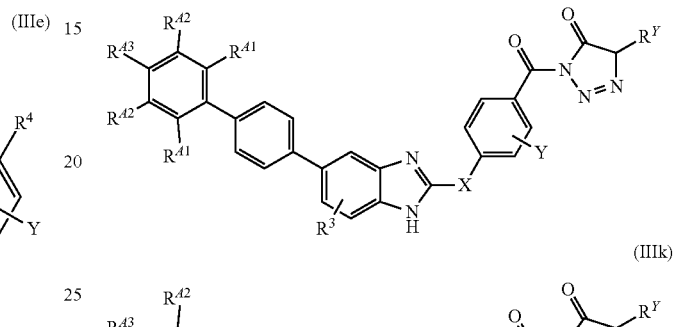

(IIIj)

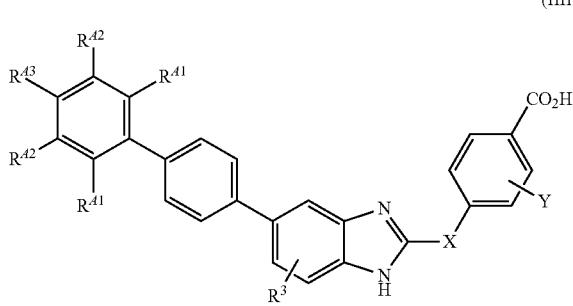

(IIIf)

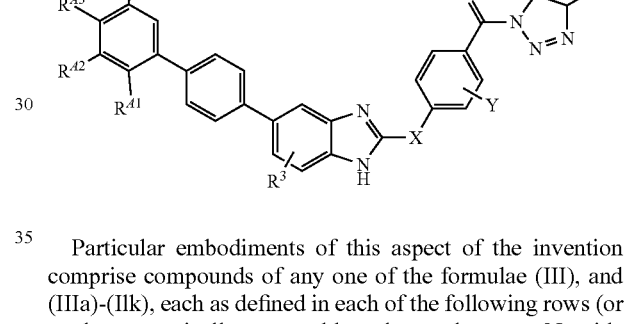

(IIIk)

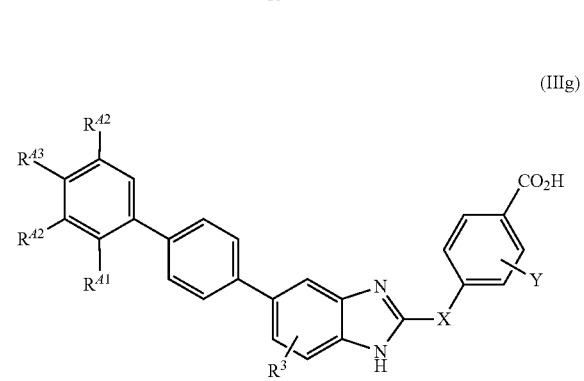

(IIIg)

Particular embodiments of this aspect of the invention comprise compounds of any one of the formulae (III), and (IIIa)-(IIk), each as defined in each of the following rows (or a pharmaceutically acceptable salt, prodrug, or N-oxide thereof, or a solvate or hydrate thereof), wherein each entry is a group number as defined above (e.g., (3y) refers to $R^1$ is —OR), an "X" indicates that the variable is covered by another group number (e.g., formula (IIIa) includes a Z group) and a dash "-" indicates that the variable is as defined in embodiment $I_1$ or defined according to any one of the applicable variable definitions (2a)-(oo), (3a)-(3mm) and (4a)-(4cc) [e.g., when $R^4$ is a dash, it can be either as defined in embodiment III or any one of the applicable definitions (3a)-(3mm)]:

(IIIh)

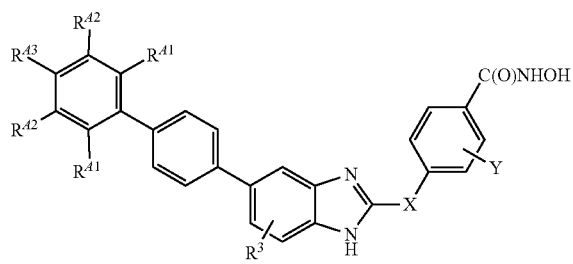

|  | (III) | $R^3$ | $R^4$ | Y |
|---|---|---|---|---|
| (3)-1 | (IIIa) | (2a) | (3b) | (4a) |
| (3)-2 | (IIIa) | (2c) | (3c) | (4c) |
| (3)-3 | (IIIa) | (2d) | (3g) | (4l) |
| (3)-4 | (IIIa) | (2f) | (3h) | (4j) |
| (3)-5 | (IIIa) | (2h) | (3o) | (4l) |
| (3)-6 | (IIIa) | (2k) | (3p) | (4u) |
| (3)-7 | (IIIa) | (2m) | (3r) | (4x) |
| (3)-8 | (IIIa) | (2n) | (3t) | (4y) |
| (3)-9 | (IIIa) | (2o) | (3u) | (4z) |
| (3)-10 | (IIIa) | (2p) | (3x) | (4aa) |
| (3)-11 | (IIIa) | (2t) | (3g) | (4bb) |
| (3)-12 | (IIIa) | (2d) | (3h) | (4cc) |
| (3)-13 | (IIIa) | (2a) | (3o) | (4u) |
| (3)-14 | (IIIa) | (2c) | (3p) | (4x) |
| (3)-15 | (IIIa) | (2d) | (3r) | (4z) |
| (3)-16 | (IIIa) | (2m) | (3t) | (4bb) |
| (3)-17 | (IIIa) | (2n) | (3g) | (4cc) |

| | (III) | R³ | R⁴ | Y |
|---|---|---|---|---|
| (3)-18 | (IIIa) | (2f) | (3h) | (4j) |
| (3)-19 | (IIIb) | (2a) | (3b) | (4a) |
| (3)-20 | (IIIb) | (2c) | (3c) | (4c) |
| (3)-21 | (IIIb) | (2d) | (3g) | (4i) |
| (3)-22 | (IIIb) | (2f) | (3h) | (4j) |
| (3)-23 | (IIIb) | (2h) | (3o) | (4l) |
| (3)-24 | (IIIb) | (2k) | (3p) | (4u) |
| (3)-25 | (IIIb) | (2m) | (3r) | (4x) |
| (3)-26 | (IIIb) | (2n) | (3t) | (4y) |
| (3)-27 | (IIIb) | (2o) | (3u) | (4z) |
| (3)-28 | (IIIb) | (2p) | (3x) | (4aa) |
| (3)-29 | (IIIb) | (2t) | (3g) | (4bb) |
| (3)-30 | (IIIb) | (2d) | (3h) | (4cc) |
| (3)-31 | (IIIb) | (2c) | (3g) | (4i) |
| (3)-32 | (IIIb) | (2d) | (3h) | (4j) |
| (3)-33 | (IIIb) | (2m) | (3p) | (4u) |
| (3)-34 | (IIIb) | (2m) | (3r) | (4x) |
| (3)-35 | (IIIb) | (2n) | (3t) | (4z) |
| (3)-36 | (IIIb) | (2t) | (3g) | (4i) |
| (3)-37 | (IIIc) | (2a) | (3h) | (4j) |
| (3)-38 | (IIIc) | (2c) | (3c) | (4c) |
| (3)-39 | (IIIc) | (2d) | (3g) | (4i) |
| (3)-40 | (IIIc) | (2f) | (3h) | (4j) |
| (3)-41 | (IIIc) | (2h) | (3o) | (4l) |
| (3)-42 | (IIIc) | (2k) | (3p) | (4u) |
| (3)-43 | (IIIc) | (2m) | (3r) | (4x) |
| (3)-44 | (IIIc) | (2n) | (3t) | (4y) |
| (3)-45 | (IIIc) | (2o) | (3u) | (4z) |
| (3)-46 | (IIIc) | (2p) | (3x) | (4aa) |
| (3)-47 | (IIIc) | (2t) | (3g) | (4bb) |
| (3)-48 | (IIIc) | (2d) | (3h) | (4cc) |
| (3)-49 | (IIIc) | (2m) | (3g) | (4i) |
| (3)-50 | (IIIc) | (2n) | (3h) | (4j) |
| (3)-51 | (IIIc) | (2t) | (3o) | (4bb) |
| (3)-52 | (IIIc) | (2c) | (3p) | (4cc) |
| (3)-53 | (IIIc) | (2d) | (3r) | (4x) |
| (3)-54 | (IIIc) | (2m) | (3t) | (4z) |
| (3)-55 | (IIId) | (2a) | (3b) | (4a) |
| (3)-56 | (IIId) | (2c) | (3e) | (4c) |
| (3)-57 | (IIId) | (2d) | (3g) | (4i) |
| (3)-58 | (IIId) | (2f) | (3h) | (4j) |
| (3)-59 | (IIId) | (2h) | (3o) | (4l) |
| (3)-60 | (IIId) | (2k) | (3p) | (4u) |
| (3)-61 | (IIId) | (2m) | (3r) | (4x) |
| (3)-62 | (IIId) | (2n) | (3t) | (4y) |
| (3)-63 | (IIId) | (2o) | (3u) | (4z) |
| (3)-64 | (IIId) | (2p) | (3x) | (4aa) |
| (3)-65 | (IIId) | (2t) | (3g) | (4bb) |
| (3)-66 | (IIId) | (2d) | (3h) | (4cc) |
| (3)-67 | (IIId) | (2m) | (3g) | (4i) |
| (3)-68 | (IIId) | (2n) | (3h) | (4j) |
| (3)-69 | (IIId) | (2t) | (3o) | (4u) |
| (3)-70 | (IIId) | (2d) | (3p) | (4x) |
| (3)-71 | (IIId) | (2m) | (3r) | (4z) |
| (3)-72 | (IIId) | (2n) | (3t) | (4i) |
| (3)-73 | (IIIe) | (2t) | (3b) | (4j) |
| (3)-74 | (IIIe) | (2c) | (3c) | (4c) |
| (3)-75 | (IIIe) | (2d) | (3g) | (4i) |
| (3)-76 | (IIIe) | (2f) | (3h) | (4j) |
| (3)-77 | (IIIe) | (2h) | (3o) | (4l) |
| (3)-78 | (IIIe) | (2k) | (3p) | (4u) |
| (3)-79 | (IIIe) | (2m) | (3r) | (4x) |
| (3)-80 | (IIIe) | (2n) | (3t) | (4y) |
| (3)-81 | (IIIe) | (2o) | (3u) | (4z) |
| (3)-82 | (IIIe) | (2p) | (3x) | (4aa) |
| (3)-83 | (IIIe) | (2t) | (3g) | (4bb) |
| (3)-84 | (IIIe) | (2d) | (3h) | (4cc) |
| (3)-85 | (IIIe) | (2c) | (3g) | (4i) |
| (3)-86 | (IIIe) | (2d) | (3h) | (4j) |
| (3)-87 | (IIIe) | (2m) | (3o) | (4x) |
| (3)-88 | (IIIe) | (2m) | (3p) | (4z) |
| (3)-89 | (IIIe) | (2n) | (3r) | (4i) |
| (3)-90 | (IIIe) | (2t) | (3t) | (4j) |
| (3)-91 | (IIIf) | (2a) | (3b) | (4a) |
| (3)-92 | (IIIf) | (2c) | (3c) | (4c) |
| (3)-93 | (IIIf) | (2d) | (3g) | (4i) |
| (3)-94 | (IIIf) | (2f) | (3h) | (4j) |
| (3)-95 | (IIIf) | (2h) | (3o) | (4l) |
| (3)-96 | (IIIf) | (2k) | (3p) | (4u) |
| (3)-97 | (IIIf) | (2m) | (3r) | (4x) |
| (3)-98 | (IIIf) | (2n) | (3t) | (4y) |
| (3)-99 | (IIIf) | (2o) | (3u) | (4z) |
| (3)-100 | (IIIf) | (2p) | (3x) | (4aa) |
| (3)-101 | (IIIf) | (2t) | (3g) | (4bb) |
| (3)-102 | (IIIf) | (2d) | (3h) | (4cc) |
| (3)-103 | (IIIf) | (2m) | (3o) | (4bb) |
| (3)-104 | (IIIf) | (2n) | (3p) | (4cc) |
| (3)-105 | (IIIf) | (2t) | (3r) | (4u) |
| (3)-106 | (IIIf) | (2d) | (3t) | (4x) |
| (3)-107 | (IIIf) | (2m) | (3h) | (4z) |
| (3)-108 | (IIIf) | (2m) | (3o) | (4i) |
| (3)-109 | (IIIg) | (2n) | (3b) | (4j) |
| (3)-110 | (IIIg) | (2t) | (3c) | (4c) |
| (3)-111 | (IIIg) | (2d) | (3g) | (4i) |
| (3)-112 | (IIIg) | (2f) | (3h) | (4j) |
| (3)-113 | (IIIg) | (2h) | (3o) | (4l) |
| (3)-114 | (IIIg) | (2k) | (3p) | (4u) |
| (3)-115 | (IIIg) | (2m) | (3r) | (4x) |
| (3)-116 | (IIIg) | (2n) | (3t) | (4y) |
| (3)-117 | (IIIg) | (2o) | (3u) | (4z) |
| (3)-118 | (IIIg) | (2p) | (3x) | (4aa) |
| (3)-119 | (IIIg) | (2t) | (3g) | (4bb) |
| (3)-120 | (IIIg) | (2d) | (3h) | (4cc) |
| (3)-121 | (IIIg) | (2m) | (3b) | (4bb) |
| (3)-122 | (IIIg) | (2n) | (3b) | (4cc) |
| (3)-123 | (IIIg) | (2t) | (3o) | (4j) |
| (3)-124 | (IIIg) | (2d) | (3p) | (4u) |
| (3)-125 | (IIIg) | (2m) | (3r) | (4x) |
| (3)-126 | (IIIg) | (2n) | (3t) | (4z) |
| (3)-127 | (IIIh) | (2t) | (3b) | (4a) |
| (3)-128 | (IIIh) | (2c) | (3c) | (4c) |
| (3)-129 | (IIIh) | (2d) | (3g) | (4i) |
| (3)-130 | (IIIh) | (2f) | (3h) | (4j) |
| (3)-131 | (IIIh) | (2h) | (3o) | (4l) |
| (3)-132 | (IIIh) | (2k) | (3p) | (4u) |
| (3)-133 | (IIIh) | (2m) | (3r) | (4x) |
| (3)-134 | (IIIh) | (2n) | (3t) | (4y) |
| (3)-135 | (IIIh) | (2o) | (3u) | (4z) |
| (3)-136 | (IIIh) | (2p) | (3x) | (4aa) |
| (3)-137 | (IIIh) | (2t) | (3g) | (4bb) |
| (3)-138 | (IIIh) | (2d) | (3h) | (4cc) |
| (3)-139 | (IIIh) | (2m) | (3b) | (4bb) |
| (3)-140 | (IIIh) | (2n) | (3o) | (4cc) |
| (3)-141 | (IIIh) | (2t) | (3p) | (4x) |
| (3)-142 | (IIIh) | (2d) | (3r) | (4z) |
| (3)-143 | (IIIh) | (2m) | (3t) | (4i) |
| (3)-144 | (IIIh) | (2m) | (3b) | (4j) |
| (3)-145 | (IIIi) | (2n) | (3b) | (4a) |
| (3)-146 | (IIIi) | (2o | (3c) | (4c) |
| (3)-147 | (IIIi) | (2d) | (3g) | (4i) |
| (3)-148 | (IIIi) | (2f) | (3h) | (4j) |
| (3)-149 | (IIIi) | (2h) | (3o) | (4l) |
| (3)-150 | (IIIi) | (2k) | (3p) | (4u) |
| (3)-151 | (IIIi) | (2m) | (3r) | (4x) |
| (3)-152 | (IIIi) | (2n) | (3t) | (4y) |
| (3)-153 | (IIIi) | (2o) | (3u) | (4z) |
| (3)-154 | (IIIi) | (2p) | (3x) | (4aa) |
| (3)-155 | (IIIi) | (2t) | (3g) | (4bb) |
| (3)-156 | (IIIi) | (2m) | (3h) | (4cc) |
| (3)-157 | (IIIi) | (2n) | (3b) | (4bb) |
| (3)-158 | (IIIi) | (2t) | (3o) | (4cc) |
| (3)-159 | (IIIi) | (2d) | (3p) | (4j) |
| (3)-160 | (IIIi) | (2m) | (3r) | (4u) |
| (3)-161 | (IIIi) | (2m) | (3t) | (4x) |
| (3)-162 | (IIIi) | (2n) | (3b) | (4z) |
| (3)-163 | (IIIj) | (2t) | (3b) | (4a) |
| (3)-164 | (IIIj) | (2c) | (3c) | (4c) |
| (3)-165 | (IIIj) | (2d) | (3g) | (4i) |
| (3)-166 | (IIIj) | (2f) | (3h) | (4j) |
| (3)-167 | (IIIj) | (2h) | (3o) | (4l) |
| (3)-168 | (IIIj) | (2k) | (3p) | (4u) |
| (3)-169 | (IIIj) | (2m) | (3r) | (4x) |
| (3)-170 | (IIIj) | (2n) | (3t) | (4y) |
| (3)-171 | (IIIj) | (2o) | (3u) | (4z) |

-continued

| (III) | R³ | R⁴ | Y |
|---|---|---|---|
| (3)-172 | (IIIj) | (2p) | (3x) | (4aa) |
| (3)-173 | (IIIj) | (2t) | (3g) | (4bb) |
| (3)-174 | (IIIj) | (2d) | (3h) | (4cc) |
| (3)-175 | (IIIj) | (2m) | (3o) | (4bb) |
| (3)-176 | (IIIj) | (2n) | (3p) | (4cc) |
| (3)-177 | (IIIj) | (2t) | (3r) | (4i) |
| (3)-178 | (IIIj) | (2c) | (3t) | (4j) |
| (3)-179 | (IIIj) | (2d) | (3p) | (4u) |
| (3)-180 | (IIIj) | (2m) | (3r) | (4x) |
| (3)-181 | (IIIk) | (2a) | (3t) | (4z) |
| (3)-182 | (IIIk) | (2c) | (3c) | (4c) |
| (3)-183 | (IIIk) | (2d) | (3g) | (4i) |
| (3)-184 | (IIIk) | (2f) | (3h) | (4j) |
| (3)-185 | (IIIk) | (2h) | (3o) | (4l) |
| (3)-186 | (IIIk) | (2k) | (3p) | (4u) |
| (3)-187 | (IIIk) | (2m) | (3r) | (4x) |
| (3)-188 | (IIIk) | (2n) | (3t) | (4y) |
| (3)-189 | (IIIk) | (2o) | (3u) | (4z) |
| (3)-190 | (IIIk) | (2p) | (3x) | (4aa) |
| (3)-191 | (IIIk) | (2t) | (3g) | (4bb) |
| (3)-192 | (IIIk) | (2d) | (3h) | (4cc) |
| (3)-193 | (IIIk) | (2c) | (3b) | (4bb) |
| (3)-194 | (IIIk) | (2m) | (3o) | (4cc) |
| (3)-195 | (IIIk) | (2n) | (3p) | (4j) |
| (3)-196 | (IIIk) | (2t) | (3r) | (4bb) |
| (3)-197 | (IIIk) | (2f) | (3o) | (4cc) |
| (3)-198 | (IIIk) | (2h) | (3p) | (4x) |
| (3)-199 | (IIIk) | (2k) | (3r) | (4z) |
| (3)-200 | (IIIk) | (2m) | (3t) | (4bb) |

In another aspect, the present invention comprises pharmaceutical compositions comprising a compound according to any one of the preceding aspects of the invention or any embodiment thereof, together with a pharmaceutically acceptable excipient, diluent, or carrier.

While not intending to be bound by theory, the inventors surmise that compounds of structural formulae (I)-(IIIk) are direct activators of AMPK, thereby activating the AMPK pathway. In one embodiment, the present compounds selectively activate one isoform of AMPK. For example, certain compounds selectively activate the $\alpha_2\beta_2\gamma_3$ isoform, such as with an $EC_{50}$ of two-fold, three-fold or even twenty-fold less than an $EC_{50}$ for another isoform. Such selectivity can confer tissue selectivity since different AMPK isoforms are expressed in different tissues. In particular the $\alpha_2$, $\beta_2$ and $\gamma_3$ subunit isoforms are found in skeletal muscle. Thus, in certain embodiments the present compounds are selective activators of AMPK in skeletal muscle.

Activation of the AMPK pathway has the effect of increasing glucose uptake, decreasing glycogen synthesis and increasing fatty acid oxidation, thereby reducing glycogen, intracellular triglyceride and fatty acid concentration and causing an increase in insulin sensitivity. Because they activate the AMPK pathway, compounds of structural formulae (I)-(IIIk) should also inhibit the inflammatory processes which occur during the early phases of atherosclerosis. Accordingly, compounds of structural formulae (I)-(IIIk) can be useful in the treatment of type II diabetes and in the treatment and prevention of atherosclerosis, cardiovascular disease, obesity and non-alcoholic fatty liver disease.

Accordingly, another aspect of the invention is a method of activating the AMPK pathway. According to this aspect of the invention, a method for activating the AMPK pathway in a cell includes contacting the cell with an effective amount of a compound, pharmaceutically acceptable salt, prodrug, solvate, hydrate, N-oxide or composition described above.

Another aspect of the invention is a method of increasing fatty acid oxidation in a cell. According to this aspect of the invention, a method of increasing fatty acid oxidation in a cell includes contacting the cell with an effective amount of a compound, pharmaceutically acceptable salt, prodrug, solvate, hydrate, N-oxide or composition described above. Acetyl Co-A carboxylase (ACC) catalyzes the formation of malonyl Co-A, a potent inhibitor of fatty acid oxidation; phosphorylation of ACC greatly reduces its catalytic activity, thereby reducing the concentration of malonyl Co-A and increasing the rate of fatty acid oxidation. Because compounds of the invention can increase the rate of phosphorylation of ACC, they can reduce the inhibition of fatty acid oxidation and therefore increase its overall rate.

Another aspect of the invention is a method of decreasing glycogen concentration in a cell. According to this aspect of the invention, a method of decreasing glycogen concentration in a cell includes contacting the cell with an effective amount of a compound, pharmaceutically acceptable salt, prodrug, solvate, hydrate, N-oxide or composition described above.

Another aspect of the invention is a method of increasing glucose uptake in a cell. According to this aspect of the invention, a method of increasing glucose uptake in a cell includes contacting the cell with an effective amount of a compound, pharmaceutically acceptable salt, prodrug, solvate, hydrate, N-oxide or composition described above.

Another aspect of the invention is a method of reducing triglyceride levels in a subject. According to this aspect of the invention, a method of reducing triglyceride levels in a subject includes administering to the subject an effective amount of a compound, pharmaceutically acceptable salt, prodrug, solvate, hydrate, N-oxide or composition described above.

Another aspect of the invention is a method of increasing the insulin sensitivity of a subject. According to this aspect of the invention, a method of increasing insulin sensitivity of a subject includes administering to the subject an effective amount of a compound, pharmaceutically acceptable salt, prodrug, solvate, hydrate, N-oxide or composition described above.

Another aspect of the invention is a method of treating type II diabetes. According to this aspect of the invention, a method of treating type II diabetes in a subject in need of such treatment includes administering to the subject an effective amount of a compound, pharmaceutically acceptable salt, prodrug, solvate, hydrate, N-oxide or composition described above.

Another aspect of the invention is a method of treating or preventing atherosclerosis or cardiovascular disease. According to this aspect of the invention, a method of treating or preventing atherosclerosis or cardiovascular disease in a subject includes administering to the subject an effective amount of a compound, pharmaceutically acceptable salt, prodrug, solvate, hydrate, N-oxide or composition described above.

In another aspect, the compounds of the invention, as activators of the AMPK pathway, the invention comprises modulating the AMPK pathway (either in vitro or in vivo) by contacting a cell with a compound, pharmaceutically acceptable salt, prodrug, solvate, hydrate, N-oxide or composition described above, or administering a compound, pharmaceutically acceptable salt, prodrug, solvate, hydrate, N-oxide or composition described above to a mammal (e.g., a human) in an amount sufficient to modulate the AMPK activity and study the effects thereby induced. Such methods are useful for studying the AMPK pathway and its role in biological mechanisms and disease states both in vitro and in vivo.

In certain embodiments, the compounds disclosed herein affect lipid signaling pathways. For example, in some embodiments, the compounds up-regulate ceramidase activity. Ceramide is a central player in sphingolipid metabolism, and is the immediate precursor of sphingomyelins and glycosphingolipids as well as the bioactive products sphingosine and sphingosine-1-phosphate. Moreover, endogenous ceramide itself mediates, at least in part, the actions of a variety of stimuli on cell differentiation, apoptosis, and growth suppression. Ceramide is deacylated by ceramidase to form sphingosine, which is in turn phosphorylated to sphingosine-1-phosphate by sphingosine kinase.

Elevated ceramide levels have been shown to induce cell apoptosis, differentiation and senescence. Moreover, elevated ceramide levels are linked to a variety of diseases and disorders, including, for example, Batten's disease, inflammatory bowel diseases, diffuse intravascular coagulation, fever, protein catabolism and/or lipid depletion, hepatosplenomegaly associated with inflammatory or metabolic liver diseases, endomyocarditis, endolithial cell and leucocyte activation, capillary thrombosis, meningo-encephalitis due to infectious agents, complications in organ transplantation, rheumatoid arthritis and connective tissue diseases, autoimmune diseases, hyperthyroidism, damage by radiation/chemotherapy agents and chronic fatigue syndrome.

Up-regulating ceramidase function (and therefore reducing the concentration of ceramide) can be used to treat disorders involving deficient cell proliferation (growth) or in which cell proliferation is otherwise desired, for example, degenerative disorders, growth deficiencies, lesions, physical trauma, and diseases in which ceramide accumulates within cells, such as Fabry disease. Other disorders that may benefit from the activation of ceramidase include neurodegenerative disorders such as Alzheimer's disease and amyotrophic lateral sclerosis and disorders of aging such as immune dysfunction, as well as disorders, such as those listed above, linked to elevated ceramide levels.

The compounds, salts, prodrugs, N-oxides, solvates and hydrates described herein can be administered, for example, to a mammalian host to retard cellular responses associated with the activation of the ceramide-mediated signal transduction pathway. The compounds can be useful, for example, in providing protection against cell senescence or apoptosis, such as occurs as a result of trauma (for example, radiation dermatitis) and aging (for example, of the skin or other organs).

Another embodiment is a method for up-regulating ceramidase function in a cell (either in vivo or in vitro), the method including contacting the cell with an effective amount of a compound, pharmaceutically acceptable salt, prodrug, N-oxide (or solvate or hydrate thereof) or composition of a compound described above.

In another embodiment, a method for decreasing ceramide concentration in a cell (either in vivo or in vitro) includes contacting the cell with an effective amount of a compound, pharmaceutically acceptable salt, prodrug, N-oxide (or solvate or hydrate thereof) or composition of a compound described above.

In another embodiment, a method for inhibiting ceramide-activated responses to stimuli in a cell (either in vivo or in vitro) includes contacting the cell with an effective amount of a compound, pharmaceutically acceptable salt, prodrug, N-oxide (or solvate or hydrate thereof) or composition described above. The stimuli can be, for example, stimuli for cell senescence and/or apoptosis.

Another embodiment is a method for treating or preventing a disease or disorder in which cell proliferation is deficient or desired in a subject, the method including administering to the subject an effective amount of a compound, pharmaceutically acceptable salt, prodrug, N-oxide (or solvate or hydrate thereof) or composition of a compound described above. Various applicable diseases and disorders are described above.

Another embodiment is a method for treating a disease or disorder linked to elevated ceramide levels in a subject, the method including administering to the subject an effective amount of a compound, pharmaceutically acceptable salt, prodrug, N-oxide (or solvate or hydrate thereof) or composition as described herein. Various applicable diseases and disorders are described above. In certain embodiments, the subject has a ceramide level higher than about 50 pmol/$10^6$ cells.

Moreover, since some drugs can induce high levels of ceramide, the compounds, salts, prodrugs, N-oxides, solvates and hydrates described herein can be usefully co-administered with such drugs in order to at least partially ameliorate this effect. For example, in certain embodiments, an effective amount of a compound, pharmaceutically acceptable salt, prodrug, N-oxide (or solvate or hydrate thereof) or composition as described herein is co-administered with a corticosteroid (for example, dexamethasone), an anti-inflammatory (for example, indomethacin), an antiviral (for example, interfereon), an immunosuppressant (for example, cyclosporin), a chemotherapy agent (for example, adriamicin), and immunopotentiant (for example, an immunoglobulin or a vaccine), or an andocrinological agent (for example, metimazole). As the person of skill in the art will appreciate, co-administration contemplates not only administration at the same time, but also administration at different times, but with time-overlapping pharmacological effects.

Another embodiment is a method for reducing the effect of aging in the skin of a subject, the method including contacting the skin with a compound, pharmaceutically acceptable salt, prodrug, N-oxide (or solvate or hydrate thereof) or composition as described herein.

Another embodiment is a method for treating or preventing radiation dermatitis in the skin of a subject, the method including contacting the skin with a compound, pharmaceutically acceptable salt, prodrug, N-oxide (or solvate or hydrate thereof) or composition as described herein.

The presently disclosed AMPK activating compounds are useful for increasing metabolic efficiency, for example by increasing fiber oxidative capacity, endurance and aerobic workload. In particular, the present compounds are useful for treating and regulating disorders of mitochondrial function, including, without limitation, exercise intolerance, chronic fatigue syndrome, muscle weakness, myoclonus, myoclonus epilepsy, such as associated with ragged-red fibers syndrome, Kearns-Sayre syndrome, Leigh's syndrome, mitochondrial myopathy encephalopathy lactacidosis stroke (MELAS) syndrome and stroke like episodes. The disclosed compounds also are useful for treating muscular dystrophic states, such as Duchenne's and Becker's muscular dystrophies and Friedreich's ataxia.

The presently disclosed AMPK activating compounds also function to reduce oxidative stress and secondary effects of such stress. Many diseases, including several of those listed above, have secondary effects caused by damage due to excessive oxidative stress which can be treated using the compounds disclosed herein. For example, free radical damage has been implicated in neurological disorders, such as Parkinson's disease, amyotrophic lateral sclerosis (Lou Gehrig's disease) and Alzheimers disease. Additional diseases in which excessive free radical damage occurs generally include hypoxic conditions and a variety of other disorders. More specifically, such disorders include ischemia, ischemic reperfusion injury (such as coronary or cerebral reperfusion injury), myocardial ischemia or infarction, cerebrovascular accidents (such as a thromboembolic or hemorrhagic stroke) that can lead to ischemia in the brain, operative ischemia, traumatic hemorrhage (for example, a hypovolemic stroke that can lead to CNS hypoxia or anoxia), resuscitation injury, spinal cord trauma, inflammatory diseases, autoimmune disorders (such as rheumatoid arthritis or systemic lupus erythematosis), Down's syndrome, Hallervorden-Spatz disease, Huntingtons chorea, Wilson's disease, diabetic angiopathy (such as peripheral vascular disease or retinal degeneration), uveitis, chronic obstructive pulmonary disease (COPD), including chronic bronchitis and emphysema, asthma, neoplasia, Crohn's disease, inflammatory bowel disease and pancreatitis. Free radical damage is also implicated in a variety of age-related disorders, particularly ophthalmic conditions such as cataracts and age-related macular degeneration.

In particular the present compounds are useful for treating neurological disorders associated with reduced mitochondrial function, oxidative stress, or both. For example, Alzheimer's disease, dementia and Parkinson's disease can be treated using the present AMPK activating compounds.

Metabolic efficiency is enhanced by the disclosed AMPK activating compounds. Thus the compounds can be administered to a subject to improve exercise efficiency and athletic performance. Moreover, conditions including, without limitation, hypoxic states, angina pectoris, coronary ischemia and organ damage secondary to coronary vessel occlusion, intermittent claudication, multi-infarct dementia, myocardial infarction, stroke, high altitude sickness and heart failure, including congestive heart failure can be treated using the disclosed compounds.

Inflammatory disorders and effects can be treated using the present compounds. For example, in one aspect, the present compounds are particularly useful for treating lung inflammation, such as is involved in asthma, COPD and transplant rejection. Similarly, the present compounds are useful in reducing organ inflammation, particularly macrophage-associated inflammation, such as inflammation of the kidney, liver and other organs. The anti-inflammatory activity of the presently disclosed compounds can be assessed as is known to those of skill in the art, for example, by using the mixed lymphocyte response in vitro.

Accordingly, one aspect of the disclosure relates to a method for treating or ameliorating a disorder or condition related to oxidative stress, mitochondrial dysfunction, free radical damage and/or metabolic inefficiency in a subject in need thereof, the method including administering to the subject an effective amount of a compound, pharmaceutically acceptable salt, prodrug, N-oxide (or solvate or hydrate thereof) or pharmaceutical composition described above.

Another aspect of the present disclosure relates to a method for the treatment or amelioration of a disorder of mitochondrial dysfunction in a subject in need thereof, the method including administering to the subject an effective amount of a compound, pharmaceutically acceptable salt, prodrug, N-oxide (or solvate or hydrate thereof) or pharmaceutical composition described above. In certain embodiments, the disorder is selected from the group consisting of exercise intolerance, chronic fatigue syndrome, muscle weakness, myoclonus, myoclonus epilepsy (such as associated with ragged-red fibers syndrome), Kearns-Sayre syndrome, Leigh's syndrome, mitochondrial myopathy encephalopathy lactacidosis stroke (MELAS) syndrome and stroke like episodes.

Another aspect of the disclosure relates to a method of increasing metabolic efficiency in a subject in need thereof, the method including administering to the subject an effective amount of a compound, pharmaceutically acceptable salt, prodrug, N-oxide (or solvate or hydrate thereof) or pharmaceutical composition described above. Such methods can be used to increase fiber oxidative capacity, endurance, aerobic workload, or any combination thereof. These methods can be used, for example, to improve exercise efficiency, exercise endurance and/or athletic performance in a subject.

Another aspect of the present disclosure relates to methods for mimicking the effects of exercise in a subject in need thereof, the method including administering to the subject an effective amount of a compound, pharmaceutically acceptable salt, prodrug, N-oxide (or solvate or hydrate thereof) or pharmaceutical composition described above.

Another aspect of the disclosure relates to a method for treating or ameliorating a disorder in a subject in need thereof, the disorder being selected from the group consisting of hypoxic states, angina pectoris, coronary ischemia and organ damage secondary to coronary vessel occlusion, intermittent claudication, multi-infarct dementia, myocardial infarction, stroke, high altitude sickness and heart failure, including congestive heart failure, the method including administering to the subject an effective amount of a compound, pharmaceutically acceptable salt, prodrug, N-oxide (or solvate or hydrate thereof) or pharmaceutical composition described above.

Another aspect of the disclosure relates to a method for the treatment of amelioration of a muscular dystrophic state in a subject in need thereof, the method including administering to the subject an effective amount of a compound, pharmaceutically acceptable salt, prodrug, N-oxide (or solvate or hydrate thereof) or pharmaceutical composition described above. In certain emobimdnents, the muscular dystrophic state is Duchenne's muscular dystrophy, Becker's muscular dystrophy, or Freidreich's ataxia.

Another aspect of the disclosure relates to a method for increasing oxidative capacity of a muscle fiber, the method including contacting the muscle fiber with a compound, pharmaceutically acceptable salt, prodrug, N-oxide (or solvate or hydrate thereof) or pharmaceutical composition described above. The contacting may be performed in vitro or in vivo.

Another aspect of the disclosure relates to a method for reducing oxidative stress in a subject in need thereof, the method including administering to the subject an effective amount of a compound, pharmaceutically acceptable salt, prodrug, N-oxide (or solvate or hydrate thereof) or pharmaceutical composition described above.

Another aspect of the disclosure relates to a method for reducing free radical damage in a subject in need thereof, the method including administering to the subject an effective amount of a compound, pharmaceutically acceptable salt, prodrug, N-oxide (or solvate or hydrate thereof) or pharmaceutical composition described above.

Another aspect of the disclosure relates to a method for treating or ameliorating a disorder or condition in a subject in need thereof, the disorder or condition selected from the group consisting of neurological disorders, hypoxic conditions, ischemia, ischemic reperfusion injury, myocardial ischemia or infarction, cerebrovascular accidents, operative ischemia, traumatic hemorrhage, resuscitation injury, spinal cord trauma, inflammatory diseases, autoimmune disorders, Down's syndrome, Hallervorden-Spatz disease, Huntingtons chorea, Wilson's disease, diabetic angiopathy, uveitis, chronic obstructive pulmonary disease (COPD), asthma, neoplasia, Crohn's disease, inflammatory bowel disease, pancreatitis and age-related disorders, the method including administering to the subject an effective amount of a compound, pharmaceutically acceptable salt, prodrug, N-oxide (or solvate or hydrate thereof) or pharmaceutical composition described above. Particular examples of such disorders and conditions are discussed above.

Another aspect of the disclosure is a method for treating or ameliorating a neurological disorder in a subject in need thereof, the neurological disorder being associated with reduced mitochondrial function, oxidative stress, or both, the method including administering to the subject an effective amount of a compound, pharmaceutically acceptable salt, prodrug, N-oxide (or solvate or hydrate thereof) or pharmaceutical composition described above. Particular examples of such neurological disorders are discussed above.

Another aspect of the disclosure relates to a method for reducing oxidative stress in a cell, the method including contacting the cell with a compound, pharmaceutically acceptable salt, prodrug, N-oxide (or solvate or hydrate thereof) or pharmaceutical composition described above. The contacting may be performed in vitro or in vivo.

Another aspect of the disclosure relates to a method for reducing free radical damage in a cell, the method including contacting the cell with a compound, pharmaceutically acceptable salt, prodrug, N-oxide (or solvate or hydrate thereof) or pharmaceutical composition described above. The contacting may be performed in vitro or in vivo.

Another aspect of the disclosure is a method for treating an inflammatory disorder or effect in a subject in need thereof, the method including including administering to the subject an effective amount of a compound, pharmaceutically acceptable salt, prodrug, N-oxide (or solvate or hydrate thereof) or pharmaceutical composition described above. For example, in one embodiment, the inflammatory disorder or effect is lung inflammation, such as is involved in asthma, COPD and transplant rejection. In another embodiment, the inflammatory disorder or effect is organ inflammation, particularly macrophage-associated inflammation, such as inflammation of the kidney, liver and other organs.

The presently disclosed AMPK-activating compounds act on particular aspects of metabolism; for example, the present compounds negatively regulate glycogen synthase and positively regulate glycogen phosphorylase. Thus, the present compounds are useful in treating disorders of glycogen storage, such as Pompe disease. The present compounds also increase autophagy, which is decreased in Pompe disease. The present compounds can be used to treat Pompe disease either alone or in adjunctively with enzyme replacement therapy, such as alglucosidase alfa (sold under the trade name MYOZYME) or the targeted enzyme therapy BMN-701 (IFG2-GAA). The compounds are useful in treating other rare metabolic disorders, including Fabry disease.

Another aspect of the disclosure is a method of increasing vascular flow in a subject in need thereof, the method including administering to the subject a therapeutically-effective amount of an AMPK-activating compound or a pharmaceutically acceptable salt, prodrug or N-oxide thereof (or a solvate or hydrate thereof). Accordingly, one embodiment of the disclosure is a method of treating a disorder of vascular flow in a subject in need thereof, the method including administering to the subject a therapeutically-effective amount of an AMPK-activating compound or a pharmaceutically acceptable salt, prodrug or N-oxide thereof (or a solvate or hydrate thereof). In certain embodiments, the disorder of vascular flow is selected from erectile dysfunction, primary or secondary Reynaud's disease, peripheral vascular disease, diabetic angiopathy and peripheral artery disease. In other embodiments, the disorder of vascular flow is selected from arteriosclerosis obliterans and Buerger's disease, and progressive systemic sclerosis, systemic erythematosus, vibration syndrome, aneurysm, and vasculitis. The person of ordinary skill in the art will determine a therapeutically-effective amount for a particular patient and a particular cancer using standard methods in the art.

Another aspect of the disclosure is a method of treating pulmonary arterial hypertension in a subject in need thereof, the method including administering to the subject a therapeutically-effective amount of an AMPK-activating compound or a pharmaceutically acceptable salt, prodrug or N-oxide thereof (or a solvate or hydrate thereof). Pulmonary arterial hypertension is a life-threatening disease involving endothelial dysfunction, vasoconstriction in small pulmonary arteries, dysregulated proliferation of certain vascular cells, and dysregulated inflammatory signaling leading to vascular remodeling, pulmonary fibrosis, and right ventricular hypertrophy. The presently disclosed compounds have antioxidative and anti-inflammatory properties, and exert beneficial effects on endothelial dysfunction, as well as inhibiting excessive proliferation of certain cells. Pulmonary arterial hypertension is described in S. L. Archer et al., Circulation, vol. 121, 2045-66 (2010), which is hereby incorporated herein by reference in its entirety. The person of ordinary skill in the art will determine a therapeutically-effective amount for a particular patient and a particular pulmonary arterial hypertensive state using standard methods in the art.

Another aspect of the disclosure is a method of treating vasculitis or venous ulcers in a subject in need thereof, the method including administering to the subject a therapeutically-effective amount of an AMPK-activating compound or a pharmaceutically acceptable salt, prodrug or N-oxide thereof (or a solvate or hydrate thereof). Accordingly, one embodiment of the disclosure is a method of treating a vasculitis in a subject in need thereof, the method including administering to the subject a therapeutically-effective amount of an AMPK-activating compound or a pharmaceutically acceptable salt, prodrug or N-oxide thereof (or a solvate or hydrate thereof). Another embodiment of the disclosure is a method of treating a venous ulcers in a subject in need thereof, the method including administering to the subject a therapeutically-effective amount of an AMPK-activating compound or a pharmaceutically acceptable salt, prodrug or N-oxide thereof (or a solvate or hydrate thereof). The person of ordinary skill in the art will determine a therapeutically-effective amount for a particular patient and a particular disorder to be treated using standard methods in the art.

The methods described herein can be useful with a wide variety of subjects. For example, in certain embodiments, the subject suffers from oxidative stress. In other embodiments, the subject does not suffer from oxidative stress. Similarly, in certain embodiments, the subject suffers from diabetes or hyperglycemia. In other embodiments, the subject does not suffer from diabetes or hyperglycemia.

Definitions

Terms used herein may be preceded and/or followed by a single dash, "-", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, arylalkyl, arylalkyl-, and -alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as $(A)_a$-B—, wherein a is 0 or 1. In such instances, when a is 0 the moiety is B— and when a is 1 the moiety is A-B—.

As used herein, the term "alkyl" includes alkyl, alkenyl and alkynyl groups of a designed number of carbon atoms, such as 1 to 6 carbons (i.e., inclusive of 1 and 6), 1 to 6 carbons, 1 to 3 carbons, or 1, 2, 3, 4, 5 or 6. The term "$C_m$-$C_n$alkyl" means an alkyl group having from m to n carbon atoms (i.e., inclusive of m and n). The term "$C_m$-$C_n$alkyl" means an alkyl group having from m to n carbon atoms. For example, "$C_1$-$C_6$alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "$C_0$alkyl"), the group is simply a single covalent bond if it is a divalent radical or is a hydrogen atom if it is a monovalent radical. For example, the moiety "—($C_0$-$C_6$alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 6 carbons.

The term "haloalkyl" is an alkyl group substituted with one or more halogen atoms, e.g. F, Cl, Br and I. A more specific term, e.g., "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like. In certain embodiments of the compounds disclosed herein, each haloalkyl is a fluoroalkyl.

The term "aryl" or "Ar" represents an aromatic ring system having a single ring (e.g., phenyl) which is optionally fused to other aromatic hydrocarbon rings or non-aromatic hydrocarbon rings. "Aryl" includes ring systems having multiple condensed rings and in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. In certain examples, aryl groups include those having a first carbocyclic, aromatic ring fused to an aromatic or aliphatic heterocycle, for example, 2,3-dihydrobenzofuranyl. The aryl groups herein are unsubstituted or, when specified as "optionally substituted", can unless stated otherwise be substituted in one or more substitutable positions with various groups, as described below.

The term "heteroaryl" or "Het" refers to an aromatic ring system containing at least one heteroatom selected from nitrogen, oxygen and sulfur in an aromatic ring. Most commonly, the heteroaryl groups will have 1, 2, 3, or 4 heteroatoms. The heteroaryl may be fused to one or more non-aromatic ring, for example, cycloalkyl or heterocycloalkyl rings, wherein the cycloalkyl (Cak) and heterocycloalkyl (Hca) rings are described herein. In one embodiment of the present compounds the heteroaryl group is bonded to the remainder of the structure through an atom in a heteroaryl group aromatic ring. In another embodiment, the heteroaryl group is bonded to the remainder of the structure through a non-aromatic ring atom. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" or "Hca" refers to a non-aromatic ring or ring system containing at least one heteroatom that is preferably selected from nitrogen, oxygen and sulfur, wherein said heteroatom is in a non-aromatic ring. The heterocycloalkyl may have 1, 2, 3 or 4 heteroatoms. The heterocycloalkyl may be saturated (i.e., a heterocycloalkyl) or partially unsaturated (i.e., a heterocycloalkenyl). Heterocycloalkyl includes monocyclic groups of three to eight annular atoms as well as bicyclic and polycyclic ring systems, including bridged and fused systems, wherein each ring includes three to eight annular atoms. The heterocycloalkyl ring is optionally fused to other heterocycloalkyl rings and/or non-aromatic hydrocarbon rings and/or phenyl rings. In certain embodiments, the heterocycloalkyl groups have from 3 to 7 members in a single ring. In other embodiments, heterocycloalkyl groups have 5 or 6 members in a single ring. In some embodiments, the heterocycloalkyl groups have 3, 4, 5, 6 or 7 members in a single ring. Examples of heterocycloalkyl groups include, for example, azabicyclo[2.2.2]octyl (in each case also "quinuclidinyl" or a quinuclidine derivative), azabicyclo[3.2.1]octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butryolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted," can unless stated otherwise be substituted in one or more substitutable positions with various groups, as described below.

The term "cycloalkyl" or "Cak" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., bridged systems) to other cycloalkyl rings. Certain examples of cycloalkyl groups present in the disclosed compounds have from 3 to 7 members in a single ring, such as having 5 or 6 members in a single ring. In some embodiments, the cycloalkyl groups have 3, 4, 5, 6 or 7 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups.

The term "ring system" encompasses monocycles, as well as fused and/or bridged polycycles.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "electron withdrawing group" means a group that withdraws electron density from the structure to which it is attached than would a similarly-attached hydrogen atom. For example, electron withdrawing groups can be selected from the group consisting of halo (e.g., fluoro, chloro, bromo, and iodo), cyano, —($C_1$-$C_4$ fluoroalkyl), —O—($C_1$-$C_4$ fluoroalkyl), —C(O)—($C_0$-$C_4$alkyl), —C(O)O—($C_0$-$C_4$alkyl), —C(O)N($C_0$-$C_4$alkyl)($C_0$-$C_4$alkyl), —S(O)$_2$O—($C_0$-$C_4$alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group.

The term "substituted," when used to modify a specified group or radical, means that one or more hydrogen atoms of the specified group or radical are each, independently of one another, replaced with the same or different substituent groups as defined below, unless specified otherwise.

Substituent groups for substituting for hydrogens on saturated carbon atoms in the specified group or radical are, unless otherwise specified, -$R^{60}$, halo, —$O^-M^+$, =O, —$OR^{70}$, —$SR^{70}$, —$S^-M^+$, =S, —$NR^{80}R^{80}$, =$NR^{70}$, =N—$OR^{70}$, trihalomethyl, —$CF_3$, —CN, —OCN, —SCN, —NO, —$NO_2$, =$N_2$, —$N_3$, —$SO_2R^{70}$, —$SO_2O^-M^+$, —$SO_2OR^{70}$, —$OSO_2R^{70}$, —$OSO_2O^-M^+$, —$OSO_2OR^{70}$, —$P(O)(O^-)_2(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$. Each $R^{60}$ is independently selected from the group consisting of alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —$O^-M^+$, =O, —$OR^{71}$, —$SR^{71}$, —$S^-M^+$, =S, —$NR^{81}R^{81}$, =$NR^{71}$, =N—$OR^{71}$, trihalomethyl, —$CF_3$, —CN, —OCN, —SCN, —NO, —$NO_2$, =$N_2$, —$N_3$, —$SO_2R^{71}$, —$SO_2O^-M^+$, —$SO_2OR^{71}$, —$OSO_2R^{71}$, —$OSO_2O^-M^+$, —$OSO_2OR^{71}$, —$P(O)(O^-)_2(M^+)_2$, —$P(O)(OR^{71})O^-M^+$, —$P(O)(OR^{71})_2$, —$C(O)R^{71}$, —$C(S)R^{71}$, —$C(NR^{71})R^{71}$, —$C(O)O^-M^+$, —$C(O)OR^{71}$, —$C(S)OR^{71}$, —$C(O)NR^{81}R^{81}$, —$C(NR^{71})NR^{81}R^{81}$, —$OC(O)R^{71}$, —$OC(S)R^{71}$, —$OC(O)O^-M^+$, —$OC(O)OR^{71}$, —$OC(S)OR^{71}$, —$NR^{71}C(O)R^{71}$, —$NR^{71}C(S)R^{71}$, —$NR^{71}CO_2^-M^+$, —$NR^{71}CO_2R^{71}$, —$NR^{71}C(S)OR^{71}$, —$NR_{71}C(O)NR^{81}R^{81}$, —$NR^{71}C(NR^{71})R^{71}$ and —$NR^{71}C(NR^{71})NR^{81}R^{81}$. Each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$alkyl substitution; and each $M^+$ is a counter ion with a net single positive charge. Each $R^{71}$ is independently hydrogen or $R^{61}$ in which $R^{61}$ is alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{72}$, —SR$^{72}$, —S$^-$M$^+$, =S, —NR$^{82}$R$^{82}$, =NR$^{72}$, =N—OR$^{72}$, trihalomethyl, —CF$_3$, —CN, —OCN, —SCN, —NO, —NO$_2$, =N$_2$, —N$_3$, —SO$_2$R$^{71}$, —SO$_2$O$^-$M$^+$, —SO$_2$OR$^{72}$, —OSO$_2$R$^{72}$, —OSO$_2$O$^-$M$^+$, —OSO$_2$OR$^{72}$, —P(O)(O$^-$)$_2$(M$^+$)$_2$, —P(O)(OR$^{72}$)O$^-$M$^+$, —P(O)(OR$^{72}$)$_2$, —C(O)R$^{72}$, —C(S)R$^{72}$, —C(NR$^{72}$)R$^{72}$, —C(O)O$^-$M$^+$, —C(O)OR$^{72}$, —C(S)OR$^{72}$, —C(O)NR$^{82}$R$^{82}$, —C(NR$^{72}$)NR$^{82}$R$^{82}$, —OC(O)R$^{72}$, —OC(S)R$^{72}$, —OC(O)O$^-$M$^+$, —OC(O)OR$^{72}$, —OC(S)OR$^{72}$, —NR$^{72}$C(O)R$^{72}$, —NR$^{72}$C(S)R$^{72}$, —NR$^{72}$CO$_2^-$M$^+$, —NR$^{72}$CO$_2$R$^{72}$, —NR$^{72}$C(S)OR$^{72}$, —NR$^{72}$C(O)NR$^{82}$R$^{82}$, —NR$^{72}$C(NR$^{72}$)R$^{72}$ and —NR$^{72}$C(NR$^{72}$)NR$^{82}$R$^{82}$; and each R$^{81}$ is independently R$^{71}$ or alternatively, two R$^{81}$s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution. Each R$^{72}$ is independently hydrogen, (C$_1$-C$_6$alkyl) or (C$_1$-C$_6$fluoroalkyl); each R$^{82}$ is independently R$^{72}$ or alternatively, two R$^{82}$s, taken together with the nitrogen atom to which they are bonded, form a 5-, 6- or 7-membered heterocycloalkyl which may optionally include 1, 2, 3 or 4 of the same or different additional heteroatoms selected from the group consisting of O, N and S, of which N may have —H or C$_1$-C$_3$alkyl substitution. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means e.g. that one of the counter ions for such divalent alkali earth ions can be an ionized form of a presently disclosed compound and the other a typical counter ion such as chloride, or two ionized presently disclosed molecules can serve as counter ions for such divalent alkali earth ions, or a doubly ionized compound can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4-methyl-piperazin-1-yl and N-morpholinyl.

Substituent groups for hydrogens on unsaturated carbon atoms in "substituted" alkene, alkyne, aryl and heteroaryl groups are, unless otherwise specified, -R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OC$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

Substituent groups for hydrogens on nitrogen atoms in "substituted" heteroalkyl and heterocycloalkyl groups are, unless otherwise specified, -R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In certain embodiments of the compounds disclosed herein, a group that is substituted has 1, 2, 3, or 4 substituents, 1, 2, or 3 substituents, 1 or 2 substituents, or 1 substituent.

In certain embodiments, substituent groups on "substituted" alkyl, cycloalkyl, heterocycloalkyl, aryl and heteroaryl groups are -halo, —OH, —O—(C$_1$-C$_4$alkyl), —O—(C$_1$-C$_4$haloalkyl), —N(C$_0$-C$_4$ alkyl)(C$_0$-C$_4$alkyl), —SH, —S(O)$_{0-2}$-(C$_1$-C$_4$alkyl), —(C$_1$-C$_4$alkyl), —(C$_1$-C$_4$haloalkyl), —C(O)—(C$_0$-C$_4$alkyl), —C(O)N(C$_0$-C$_4$alkyl)(C$_0$-C$_4$alkyl), —N(C$_0$-C$_4$alkyl)C(O)(C$_0$-C$_4$alkyl)(C$_0$-C$_4$alkyl), —C(O)O—(C$_0$-C$_4$alkyl), —OC(O)—(C$_0$-C$_4$alkyl), S(O)$_2$—O(C$_0$-C$_4$alkyl), and —NO$_2$, in which no alkyl is further substituted.

The compounds disclosed herein can also be provided as pharmaceutically acceptable salts. The term "pharmaceutically acceptable salts" or "a pharmaceutically acceptable salt thereof" refer to salts prepared from pharmaceutically acceptable non-toxic acids or bases including inorganic acids and bases and organic acids and bases. If the compound is basic, salts may be prepared from pharmaceutically acceptable non-toxic acids. Such salts may be, for example, acid addition salts of at least one of the following acids: benzenesulfonic acid, citric acid, α-glucoheptonic acid, D-gluconic acid, glycolic acid, lactic acid, malic acid, malonic acid, mandelic acid, phosphoric acid, propanoic acid, succinic acid, sulfuric acid, tartaric acid (d, l, or dl), tosic acid (toluenesulfonic acid), valeric acid, palmitic acid, pamoic acid, sebacic acid, stearic acid, lauric acid, acetic acid, adipic acid, carbonic acid, 4-chlorobenzenesulfonic acid, ethanedisulfonic acid, ethylsuccinic acid, fumaric acid, galactaric acid (mucic acid), D-glucuronic acid, 2-oxo-glutaric acid, glycerophosphoric acid, hippuric acid, isethionic acid (ethanolsulfonic acid), lactobionic acid, maleic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, hydriodic acid, hydrobromic acid, hydrochloric acid, methanesulfonic acid, nicotinic acid, nitric acid, orotic acid, oxalic acid, picric acid, L-pyroglutamic acid, saccharine, salicylic acid, gentisic acid, and/or 4-acetamidobenzoic acid.

The compounds described herein can also be provided in prodrug form. "Prodrug" refers to a derivative of an active compound (drug) that undergoes a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Specific examples of suitable progroups and their respective promoieties will be apparent to those of skill in the art.

The compounds disclosed herein can also be provided as N-oxides.

The presently disclosed compounds, salts, prodrugs and N-oxides can be provided, for example, in solvate or hydrate form.

One of ordinary skill in the art of medicinal chemistry also will appreciate that the disclosed structures are intended to include isotopically enriched forms of the present compounds. As used herein "isotopes" includes those atoms having the same atomic number but different mass numbers. As is known to those of skill in the art, certain atoms, such as hydrogen occur in different isotopic forms. For example, hydrogen includes three isotopic forms, protium, deuterium and tritium. As will be apparent to those of skill in the art upon consideration of the present compounds, certain compounds can be enriched at a given position with a particular isotope of the atom at that position. For example, compounds having a fluorine atom, may be synthesized in a form enriched in the radioactive fluorine isotope $^{18}F$. Similarly, compounds may be enriched in the heavy isotopes of hydrogen: deuterium and tritium; and similarly can be enriched in a radioactive isotope of carbon, such as $^{13}C$. Such isotopic variant compounds undergo different metabolic pathways and can be useful, for example, in studying the ubiquitination pathway and its role in disease.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" an enzyme with a compound includes the administration of a compound described herein to an individual or patient, such as a human, as well as, for example, introducing a compound into a sample containing a cellular or purified preparation containing the enzyme.

As used herein, the terms "individual," "patient," or "subject" are used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed or otherwise susceptible to the disease, condition or disorder but does not yet experience or display the pathology or symptomatology of the disease;

(2) inhibiting the disease; for example, inhibiting a disease, condition, or disorder in an individual who is experiencing or displaying the pathology or symptomatology of the disease, condition or disorder; or (3) ameliorating the disease (including a symptom thereof); for example, ameliorating a disease, condition, or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" mean (i) ameliorating the referenced disease state, condition, or disorder (or a symptom thereof), such as, for example, ameliorating a disease, condition or disorder in an individual who is experiencing or displaying the pathology or symptomatology of the disease, condition or disorder (e.g., reversing or improving the pathology and/or symptomatology) such as decreasing the severity of disease or symptom thereof.

As used here, the terms "activating" and "activation" are meant to represent the biological effect of increasing the activity (i.e., phosphorylation of downstream substrates) of fully phosphorylated AMPK or increasing the phosphorylation of AMPK. An "activator" is a compound capable of achieving this biological effect.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Pharmaceutical Formulations and Dosage Forms

The compounds of structural formulae (I)-(III) can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like.

Pharmaceutical compositions can be made using the presently disclosed compounds. For example, in one embodiment, a pharmaceutical composition includes a pharmaceutically acceptable carrier, diluent or excipient, and compound as described above with reference to structural formulae (I)-(III).

In the pharmaceutical compositions disclosed herein, one or more compounds of structural formulae (I)-(III) may be present in association with one or more pharmaceutically acceptable carriers, diluents or excipients, and, if desired, other active ingredients. The pharmaceutical compositions containing compounds of structural formulae (I)-(III) may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

In some embodiments, the pharmaceutically acceptable carrier, diluent, or excipient is not water. In other embodiments, the water comprises less than 50% of the composition. In some embodiments, compositions comprising less than 50% water have at least 1%, 2%, 3%, 4% or 5% water. In other embodiments, the water content is present in the composition in a trace amount.

In some embodiments, the pharmaceutically acceptable carrier, diluent, or excipient is not alcohol. In other embodiments, the alcohol comprises less than 50% of the composition. In some embodiments, compositions comprising less than 50% alcohol have at least 1%, 2%, 3%, 4% or 5% alcohol. In other embodiments, the alcohol content is present in the composition in a trace amount.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of structural formulae (I)-(III) can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of structural formula (I)-(III) can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

EXAMPLES

General Synthetic Methodologies

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/1, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The compounds disclosed herein can be made using procedures familiar to the person of ordinary skill in the art and as described herein. For example, compounds of structural formula (I) can be prepared according to Schemes 1-3, or analogous synthetic schemes.

One of skill in the art can adapt the reaction sequences of Schemes 1-3 to fit the desired target molecule. Of course, in certain situations one of skill in the art will use different reagents to affect one or more of the individual steps or to use protected versions of certain of the substituents. Additionally, one skilled in the art would recognize that compounds of structural formulae (I)-(III) can be synthesized using different routes altogether.

Compounds suitable for use in the presently disclosed pharmaceutical compositions include compounds of Table 1, above. These compounds can be made according to the general schemes described above, for example using a procedure similar to that described below in the Examples.

The following examples are intended to further illustrate certain embodiments and are not intended to limit the scope of the presently disclosed compounds.

Examples

Example 1: Synthesis and Characterization

Scheme 1: General Procedure for the Formation of Hydroxamic Acids from the Corresponding Carboxylic Acid

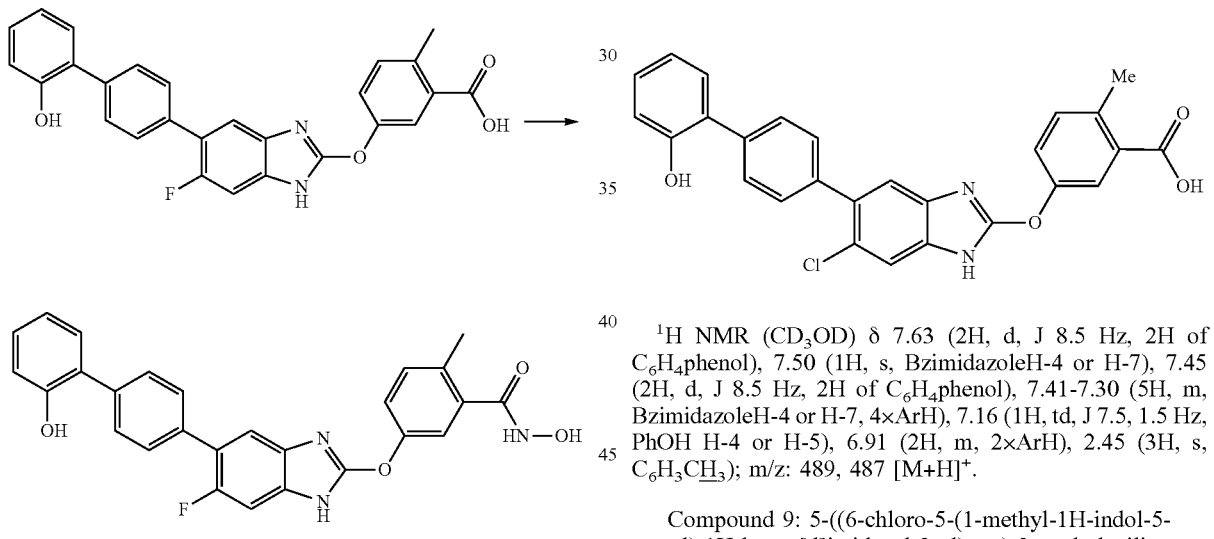

To a solution of the benzoic acid (0.013 g, 0.028 mmol, 1.0 eq) in dimethylformamide (0.5 mL) was added tetrahydropyranylhydroxylamine (0.005 g, 0.041 mmol, 1.5 eq). Triethylamine (0.008 mL, 0.055 mmol, 2.0 eq) was added followed by HATU (0.016 g, 0.041 mmol, 1.5 eq) and the reaction stirred at room temperature for 14 hours. The reaction was partitioned between EtOAc (40 mL) and water (35 mL). The organics were washed with brine (35 mL), water (35 mL) and brine (35 mL), dried (Na$_2$SO$_4$) and concentrated under reduced pressure. The crude material was dissolved in methanol (0.5 mL) and toluenesulfonic acid monohydrate (0.008 g, 0.041 mmol, 1.5 eq) added. The reaction was stirred at room temperature for 2 hours before adding brine (15 mL). The organics were extracted with EtOAc (3×20 mL), combined, dried (Na$_2$SO$_4$) and concentrated under reduced pressure. Column chromatography (silica, 0→10% MeOH—CH$_2$Cl$_2$) yielded the hydroxamic acid as a white solid.

Compound 1: 5-((6-chloro-5-(1-methyl-1H-indol-5-yl)-1H-benzo[d]imidazol-2-yl)oxy)-N-hydroxy-2-methylbenzamide

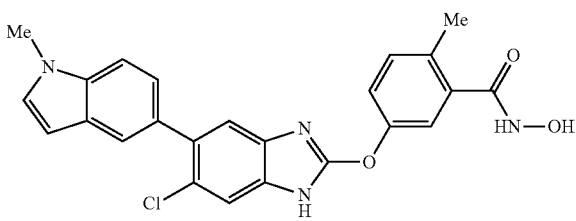 [SMILES: Cc1ccc(Oc2nc3cc(-c4ccc5c(ccn5C)c4)c(Cl)cc3[nH]2)cc1C(=O)NO]

$^1$H NMR (CD$_3$OD) δ 7.55 (1H, d, J 1.5 Hz, 1×ArH), 7.47 (1H, s, 1×ArH), 7.41-7.33 (5H, m, 5×ArH), 7.21 (1H, dd, J 8.5, 2.0 Hz, 1×ArH), 7.18 (1H, d, J 3.0 Hz, indoleH-2 or H-3), 6.45 (1H, dd, J 3.0, 1.0 Hz, indoleH-2 or H-3), 3.84 (3H, s, NCH$_3$), 2.44 (3H, s, ArCH$_3$); m/z: 450, 448 [M+H]$^+$ (found [M+H]$^+$, 448.1229, C$_{24}$H$_{19}$ClN$_4$O$_3$ requires [M+H]$^+$ 448.1218).

Compound 3: 5-((6-chloro-5-(2'-hydroxy-[1,1'-biphenyl]-4-yl)-1H-benzo[d]imidazol-2-yl)oxy)-N-hydroxy-2-methylbenzamide $^1$H NMR (CD$_3$OD) δ 7.63 (2H, d, J 8.5 Hz, 2H of C$_6$H$_4$phenol), 7.50 (1H, s, BzimidazoleH-4 or H-7), 7.45 (2H, d, J 8.5 Hz, 2H of C$_6$H$_4$phenol), 7.41-7.30 (5H, m, BzimidazoleH-4 or H-7, 4×ArH), 7.16 (1H, td, J 7.5, 1.5 Hz, PhOH H-4 or H-5), 6.91 (2H, m, 2×ArH), 2.45 (3H, s, C$_6$H$_3$CH$_3$); m/z: 489, 487 [M+H]$^+$.

Compound 9: 5-((6-chloro-5-(1-methyl-1H-indol-5-yl)-1H-benzo[d]imidazol-2-yl)oxy)-2-methylaniline

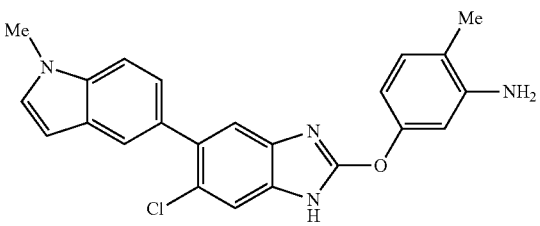 [SMILES: Cc1ccc(Oc2nc3cc(-c4ccc5c(ccn5C)c4)c(Cl)cc3[nH]2)cc1N]

$^1$H NMR (CD$_3$OD+CDCl$_3$) δ 7.56 (1H, d, J 2.0 Hz, indoleH-7), 7.44 (1H, s, benzimidazoleH-4 or H-7), 7.36 (1H, d, J 8.5 Hz, indoleH-4), 7.33 (1H, s, benzimidazoleH-4 or H-7), 7.22 (1H, dd, J 8.5, 2.0 Hz, indoleH-5), 7.14 (1H, d, J 3.5 Hz, indoleH-2 or H-3), 7.03 (1H, d, J 8.5 Hz, C$_6$H$_3$H-5), 6.64 (1H, d, J 2.5 Hz, C$_6$H$_3$H-2), 6.52 (1H, dd, J 8.0, 2.5 Hz, C$_6$H$_3$H-6), 6.45 (1H, d, J 3.0 Hz, indoleH-2 or H-3), 3.82 (3H, s, NCH$_3$), 2.15 (3H, s, ArCH$_3$); m/z: 406, 404 [M+H]$^+$ (found [M+H]$^+$, 403.1298, C$_{23}$H$_{19}$ClN$_{4}$O requires [M+H]$^+$ 403.1320).

Compound 11: 5-((6-fluoro-5-(2'-hydroxy-[1,1'-biphenyl]-4-yl)-1H-benzo[d]imidazol-2-yl)oxy)-2-methylbenzonitrile

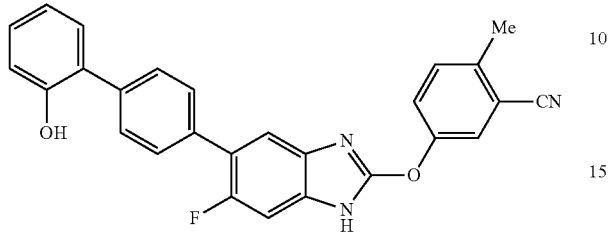

$^1$H NMR (CD$_3$OD) δ 7.78 (1H, d, J 2.0 Hz, C$_6$H$_3$H-2), 7.70 (2H, d, J 8.5 Hz, 2H of C$_6$H$_4$phenol), 7.64-7.55 (4H, m, 2H of C$_6$H$_4$phenol, BzimidazoleH-4, 1H of C$_6$H$_4$OH H-4 or H-5), 7.52 (1H, d, J 7.0 Hz, C$_6$H$_4$OH H-3 or H-6), 7.37 (1H, dd, J 8.0, 1.5 Hz, C$_6$H$_4$OH H-3 or H-6), 7.27 (1H, d, J 11.0 Hz, BzimidazoleH-7), 7.23 (1H, td, J 7.5, 2.0 Hz, C$_6$H$_4$OH H-4 or H-5), 7.01-6.96 (2H, m, C$_6$H$_3$H-5, H-6), 2.63 (3H, s, C$_6$H$_3$CH$_3$); $^{19}$F NMR (CD$_3$OD) δ −125.8; m/z: 437[M+H]$^+$ (found [M+H]$^+$, 436.1456, C$_{27}$H$_{18}$FN$_3$O$_2$ requires [M+H]$^+$ 436.1456).

Scheme 2: General Scheme for the Synthesis of Tetrazalone Compounds

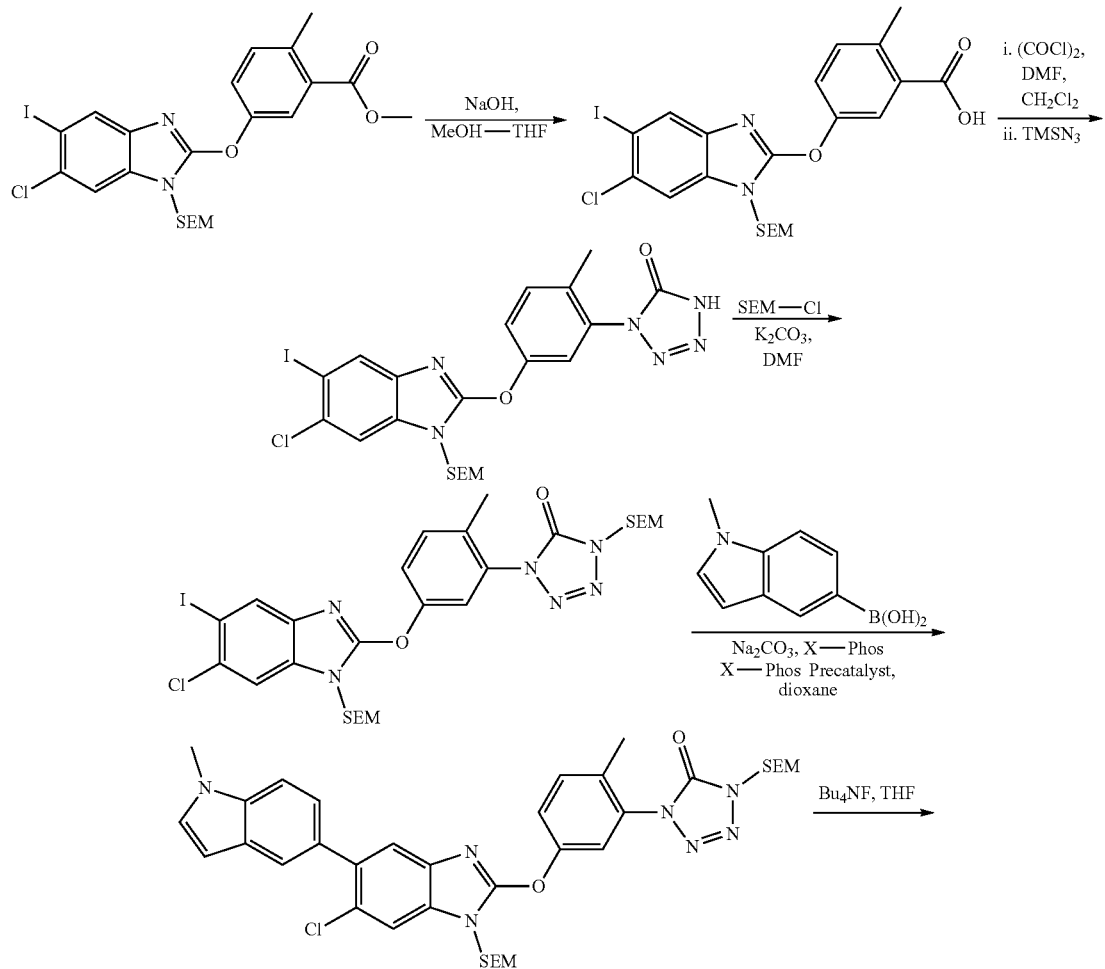

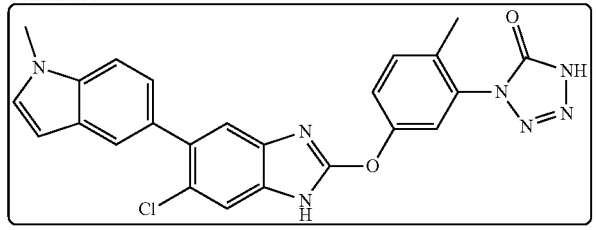

Formation of 5-(N-Methylindol-5-yl)-6-chlorobenzimidazole

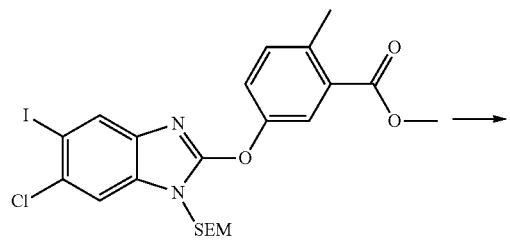

To a solution of the methyl ester (0.52 g, 0.908 mmol, 1.0 eq) in methanol-tetrahydrofuran (5:3, 8 mL) was added aqueous sodium hydroxide (2 mL of a 2.5M solution, 5.0 mmol). The reaction was stirred at room temperature for 14 hours and concentrated to remove methanol. The concentrate was partitioned between EtOAc (60 mL) and HCl (1M, 50 mL). The aqueous phase was extracted with EtOAc (2×50 mL). The combined organics were dried (Na$_2$SO$_4$) and concentrated under reduced pressure. Column chromatography (silica, 20→80% EtOAc-hexane) yielded the carboxylic acid (0.28 g, 55%); m/z: 562, 560 [M+H]$^+$.

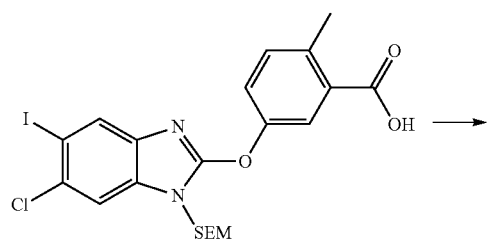

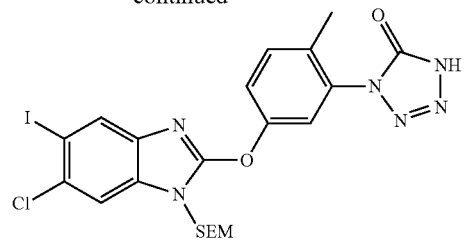

A solution of the benzoic acid (0.277 g, 0.496 mmol, 1.0 eq) in dichloromethane (5 mL) was cooled to 0° C. and oxalyl chloride (0.056 g, 0.645 mmol, 1.3 eq) added followed by dimethylformamide (1 drop). The reaction was stirred at 0° C. for 10 minutes and room temperature for 2 hours. The reaction was concentrated under reduced pressure, concentrating from ethyl acetate (2×10 mL). The residue was suspended in azidotrimethylsilane (5 mL). The reaction was allowed to warm slowly to 90° C. and stirred at 90° C. for 14 hours. The reaction was cooled and concentrated to dryness. Column chromatography (silica, 20→100% EtOAc-hexane) yielded the tetrazalone; $^1$H NMR (CDCl$_3$) δ 8.03 (0.5H, s, 1 isomer of Bzimidazole H-4 or H-7), 7.87 (0.5H, s, 1 isomer of Bzimidazole H-4 or H-7), 7.68 (0.5H, s, 1 isomer of Bzimidazole H-4 or H-7), 7.54 (1.5H, m, 1H of C$_6$H$_3$, 1 isomer of Bzimidazole H-4 or H-7), 7.42 (2H, m, 2H of C$_6$H$_3$), 5.49 (2H, s, NCH$_2$O), 3.64 (2H, m, OCH$_2$CH$_2$TMS), 2.33 (3H, s, C$_6$H$_3$CH$_3$), 0.96 (2H, m, OCH$_2$CH$_2$TMS), −0.02 (4.5H, s 1 isomer of Si(CH$_3$)$_3$), −0.02 (4.5H, s 1 isomer of Si(CH$_3$)$_3$); m/z: 601, 599 [M+H]$^+$.

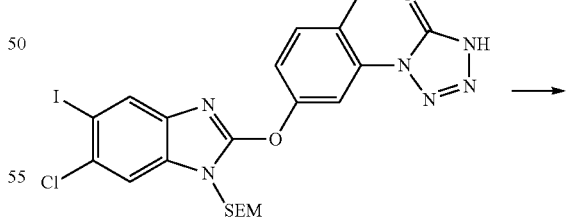

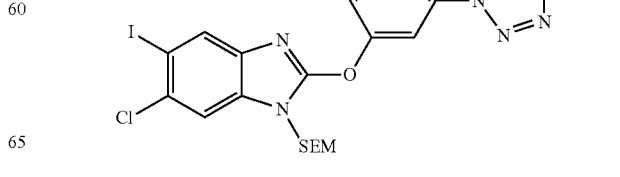

To a solution of the tetrazalone (0.050 g, 0.084 mmol, 1.0 eq) in dimethylformamide (1.0 mL) was added (trimethylsilyl)ethoxymethyl chloride (0.030 mL, 0.167 mmol, 2.0 eq) followed by ground potassium carbonate (0.029 g, 0.209 mmol, 2.5 eq). The reaction was stirred at room temperature for 18 hours and partitioned between EtOAc (40 mL) and water (40 mL). The organics were washed with brine (40 mL), water (40 mL) and brine (40 mL), dried (Na$_2$SO$_4$), and concentrated under reduced pressure. Column chromatography (silica, 10→40% EtOAc-hexane) yielded the SEM protected tetrazalone (0.031 g, 51%) as a white solid; $^1$H NMR (CDCl$_3$) δ 8.02 (0.5H, s, 1 isomer of Bzimidazole H-4 or H-7), 7.87 (0.5H, s, 1 isomer of Bzimidazole H-4 or H-7), 7.67 (0.5H, s, 1 isomer of Bzimidazole H-4 or H-7), 7.54 (0.5H, s, 1 isomer of Bzimidazole H-4 or H-7), 7.50 (1H, m, 1H of C$_6$H$_3$), 7.46 (2H, m, 2H of C$_6$H$_3$), 5.47 (2H, s, 1×NCH$_2$O), 5.39 (2H, s, 1×NCH$_2$O), 3.76 (2H, m, 1×OCH$_2$CH$_2$TMS), 3.63 (2H, m, 1×OCH$_2$CH$_2$TMS), 2.34 (3H, s, C$_6$H$_3$CH$_3$), 1.02-0.92 (4H, m, 2×OCH$_2$CH$_2$TMS), 0.02 (9H, s, 1×Si(CH$_3$)$_3$), −0.02 (4.5H, s, 1 isomer of Si(CH$_3$)$_3$), −0.03 (4.5H, s, 1 isomer of Si(CH$_3$)$_3$); m/z: 732, 730 [M+H]$^+$.

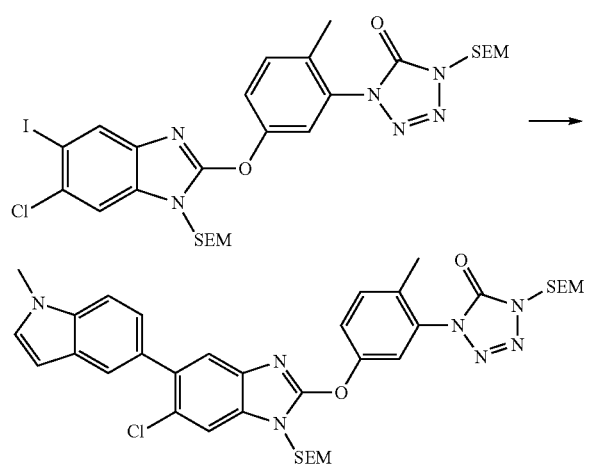

To a mixture of N-methyl-5-indoleboronic acid (0.009 g, 0.051 mmol, 1.2 eq), X-Phos (0.002, 0.004 mmol, 0.1 eq) was added aqueous sodium carbonate (0.043 mL, 2.0M, 0.085 mmol, 2.0 eq). A solution of iodobenzimidazole (0.031 g, 0.043 mmol, 1.0 eq) in dioxane (1.0 mL) was added and the reaction mixture degassed by bubbling argon through for five minutes. X-Phos precatalyst (0.003 g, 0.04 mmol, 0.1 eq) was added and the reaction further degassed before heating to 100° C. for 22 hours. The reaction was cooled and partitioned between EtOAc (40 mL) and water (40 mL). The aqueous phase was extracted with EtOAc (40 mL). The combined organics were washed with brine (40 mL), dried (Na$_2$SO$_4$) and concentrated under reduced pressure. Column chromatography (silica, 5→50% EtOAc-hexane) yielded the coupled product; m/z: 735, 733 [M+H]$^+$.

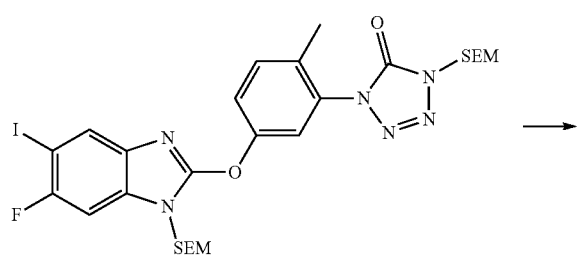

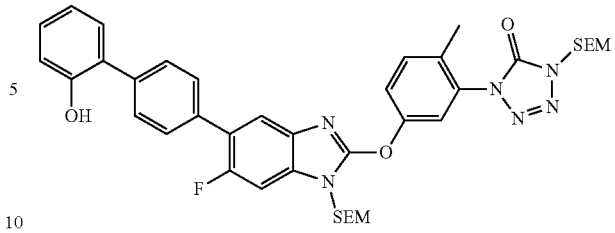

A similar procedure was used to that described above on a 0.035 mmol scale, with heating to 110° C. carried out for 24 hours before adding additional X-Phos (0.1 eq) and X-Phos precatalyst (0.1 eq) and stirring at 110° C. for a further 24 hours. Column chromatography (silica, 5→50% EtOAc-hexane) yielded starting material and coupled product (0.011 g) as a colourless oil.

Compound 4: 1-(5-((6-chloro-5-(1-methyl-1H-indol-5-yl)-1H-benzo[d]imidazol-2-yl)oxy)-2-methylphenyl)-1,4-dihydro-5H-tetrazol-5-one

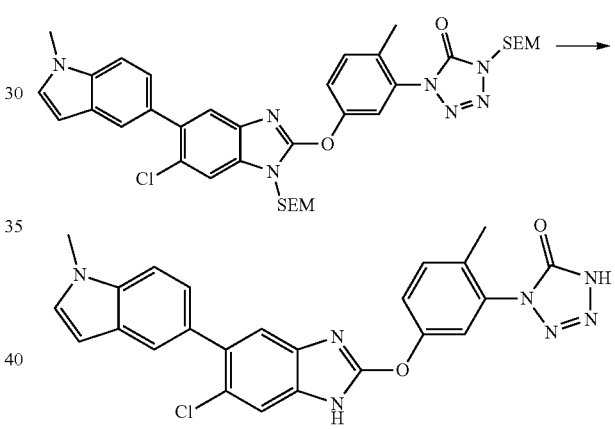

To a solution of the bis-(SEM) protected benzimidazole (0.012 g, 0.016 mmol, 1.0 eq) in tetrahydrofuran (0.5 mL) was added tetrabutylammonium fluoride (0.066 mL of a 1.0M solution in tetrahydrofuran, 0.066 mmol, 4.0 eq). The reaction was heated to 80° C. for 2 hours. Further tetrabutylammonium fluoride (0.066 mL of a 1.0M solution in tetrahydrofuran, 0.066 mmol, 4.0 eq) was added and the reaction stirred at 80° C. for 4 hours. The reaction was cooled and partitioned between EtOAc (50 mL) and KHSO$_4$ (40 mL). The aqueous phase was extracted with EtOAc (2×20 mL). The combined organics were washed with water (30 mL) and brine (30 mL), dried (Na$_2$SO$_4$) and concentrated under reduced pressure. Column chromatography (silica, 0→10% MeOH—CH$_2$Cl$_2$) yielded Compound 4: $^1$H NMR (CD$_3$OD) δ 7.55-7.48 (3H, m, 3×ArH), 7.46-7.43 (2H, m, 2×ArH), 7.39 (1H, d, J 9.0 Hz, C$_6$H$_3$H-6 or indoleH-7), 7.36 (1H, s, BzimidazoleH-4 or H-7), 7.21 (1H, dd, J 8.5, 2.0 Hz, C$_6$H$_3$H-5 or indoleH-6), 7.18 (1H, d, J 3.5 Hz, indoleH-2 or H-3), 6.45 (1H, dd, J 3.0, 1.0 Hz, indoleH-2 or H-3), 3.83 (3H, s, NCH$_3$), 2.29 (3H, s, C$_6$H$_3$CH$_3$); m/z: 475, 473 [M+H]$^+$ (found [M+H]$^+$, 472.1253, C$_{24}$H$_{18}$ClN$_7$O$_2$ requires [M+H]$^+$ 472.1283).

Mono-Deprotected Analog of Compound 4

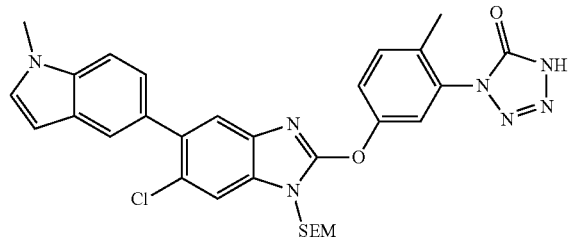 [SMILES: Cc1ccc(Oc2nc3cc(-c4ccc5c(ccn5C)c4)c(Cl)cc3n2COCC[Si](C)(C)C)cc1-n1nn[nH]c1=O]

In the deprotection reaction a sample of the monodeprotected product was isolated as a mixture of benzimidazole regioisomers; m/z: 605, 603 [M+H]+.

Compound 6: 1-(5-((6-fluoro-5-(2'-hydroxy-[1,1'-biphenyl]-4-yl)-1H-benzo[d]imidazol-2-yl)oxy)-2-methylphenyl)-1,4-dihydro-5H-tetrazol-5-one

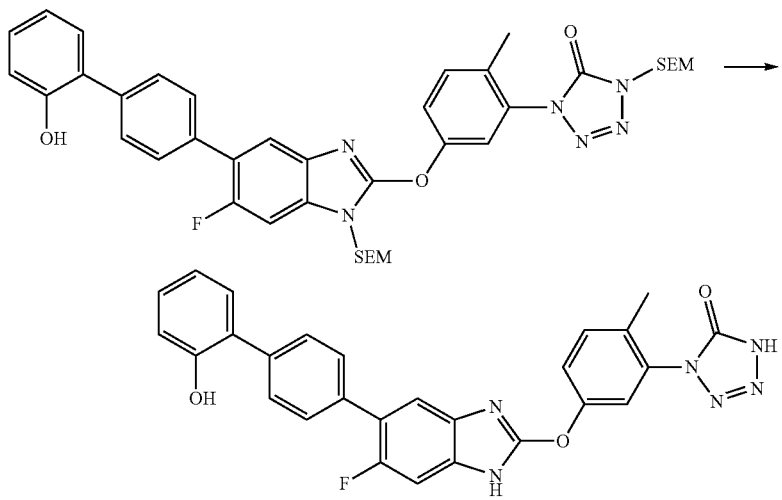

A similar deprotection procedure was used to that described above on a 0.015 mmol scale with the reaction stirred at 80° C. for 3 hours. Compound 6 was obtained as a white solid: $^1$H NMR (CD$_3$OD) δ 7.70 (2H, d, J 8.5 Hz, C$_6$H$_4$phenol), 7.62 (2H, dd, J 8.5, 1.5 Hz, 2H of C$_6$H$_4$phenol), 7.59 (1H, d, J 9.0 Hz, 1×ArH), 7.51 (3H, m, 3×ArH), 7.37 (1H, dd, J 8.0, 2.0 Hz, 1×ArH), 7.27 (1H, d, J 11.0 Hz, BzimidazoleH-3), 7.22 (1H, td, J 7.5, 2.0 Hz, PhOH H-4 or H-5), 6.97 (2H, m, 2×ArH), 2.36 (3H, s, C$_6$H$_3$CH$_3$); $^{19}$F NMR (CDCl$_3$) δ −125.8; m/z: 495 [M+H]+ (found [M+H]+, 495.1555, C$_{27}$H$_{19}$FN$_6$O$_3$ requires [M+H]+ 495.1575).

Compound 8: 1-(5-((6-chloro-5-(1-methyl-1H-indol-5-yl)-1H-benzo[d]imidazol-2-yl)oxy)-2-methylphenyl)-4-methyl-1,4-dihydro-5H-tetrazol-5-one

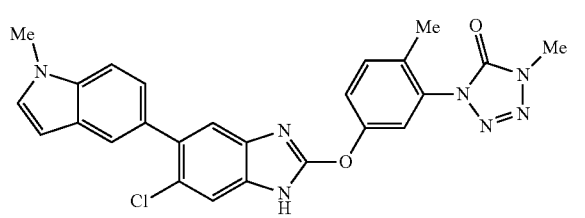 [SMILES: Cc1ccc(Oc2nc3cc(-c4ccc5c(ccn5C)c4)c(Cl)cc3[nH]2)cc1-n1nnn(C)c1=O]

A similar series of procedures was used to that described above except that the N-methyl tetrazalone was generated instead of the N-SEM tetrazalone by reaction with iodomethane. A similar deprotection procedure was used to that described above to obtain Compound 8 as a white solid; $^1$H NMR (CD$_3$OD+CDCl$_3$) δ 7.56 (1H, d, J 1.0 Hz, indoleH-4 or C$_6$H$_3$H-2), 7.51-7.45 (4H, m, BzimidazoleH-4 or H-7, indoleH-4, H-6, H-7 or C$_6$H$_3$H-2, H-5, H-6), 7.36 (1H, d, J 8.5 Hz, indoleH-7 or C$_6$H$_3$H-5), 7.35 (1H, s, BzimidazoleH-4 or H-7), 7.22 (1H, dd, J 8.5, 1.5 Hz, indoleH-6 or C$_6$H$_3$H-6), 7.13 (1H, d, J 3.0 Hz, indoleH-2 or H-3), 6.45 (1H, d, J 3.0 Hz, indoleH-2 or H-3), 3.82 (3H, s, 1×NCH$_3$), 3.68 (3H, s, 1×NCH$_3$), 2.30 (3H, s, C$_6$H$_3$CH$_3$); m/z: 489, 487 [M+H]+.

Scheme 3: Alternative Scheme for the Synthesis of Tetrazalone Compounds

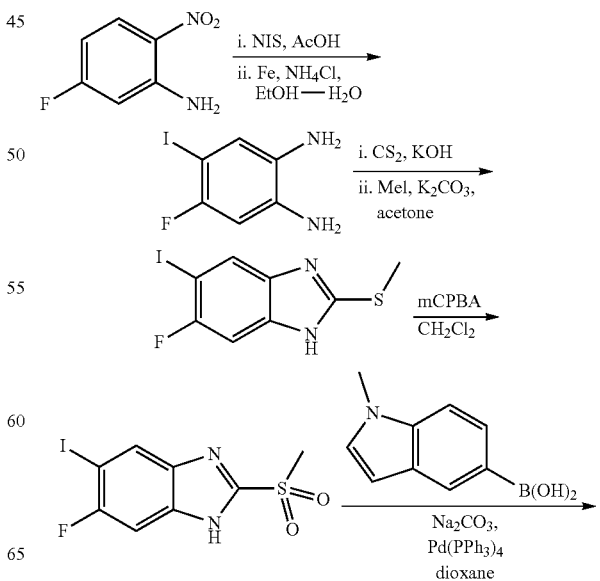

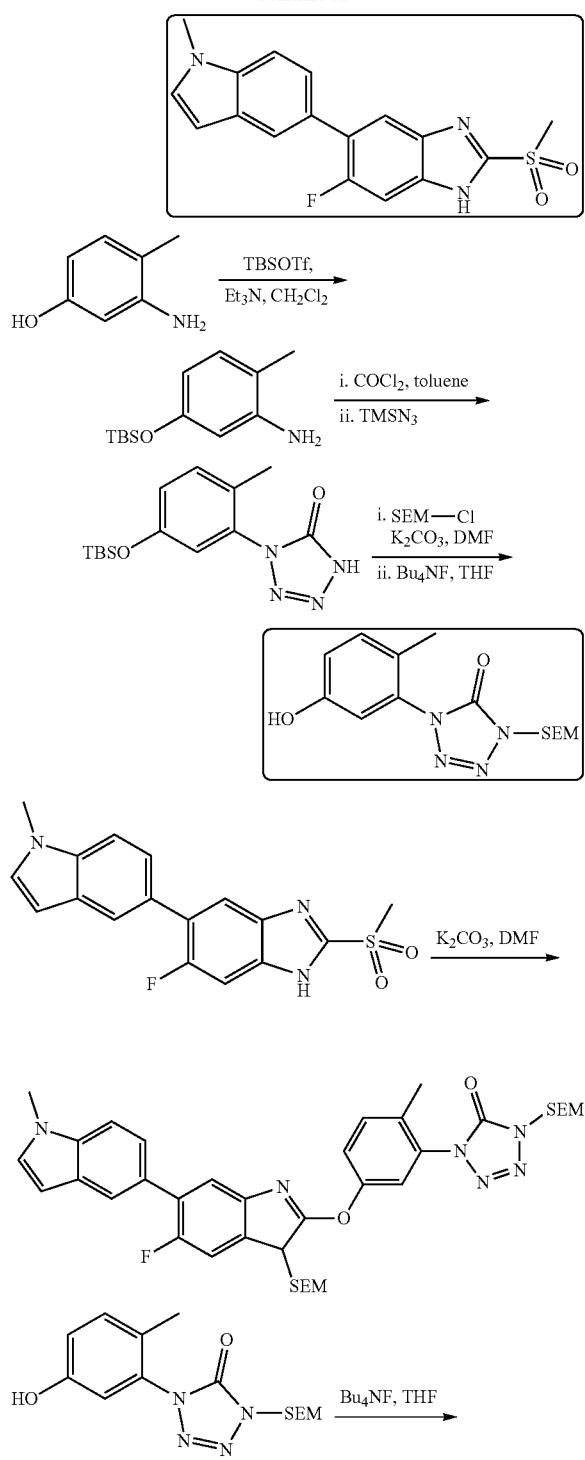

Formation of 3-(N-trimethylethoxymethyl)tetrazalon-1-yl)-4-methylphenol

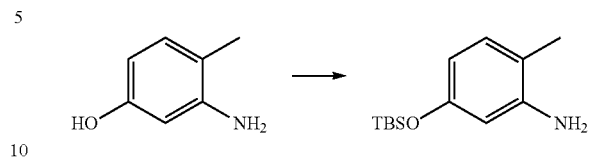

To a solution of hydroxymethylaniline (0.180 g, 1.46 mmol, 1.0 eq) and triethylamine (0.31 mL, 1.61 mmol, 1.1 eq) in dichloromethane (14 mL) at −78° C. was added t-butyldimethylsilyl trifluoromethanesulfonate (0.37 mL, 1.61 mmol, 1.1 eq). The reaction was stirred at −78° C. for 2 hours before warming to 0° C. and stirring for 1 hour. Further t-butyldimethylsilyl trifluoromethanesulfonate (0.37 mL, 1.61 mmol, 1.1 eq) was added and the reaction stirred at 0° C. for 30 minutes. The reaction was added to NaHCO$_3$ (50 mL) and the organics extracted with CH$_2$Cl$_2$ (3×50 mL). The combined organics were dried (Na$_2$SO$_4$) and concentrated under reduced pressure. Column chromatography (silica, 10→30% EtOAc-hexane) yielded the silyl-protected aniline (0.27 g, 78%) as a white solid; $^1$H NMR (CDCl$_3$) δ 6.87 (1H, d, J 9.0 Hz, C$_6$H$_3$H-5), 6.21 (2H, m, C$_6$H$_3$H-2, H-6), 2.09 (3H, C$_6$H$_3$C$\underline{H}_3$), 0.97 (9H, s, SiC(CH$_3$)$_3$), 0.17 (6H, s, Si(C$\underline{H}_3$)$_2$C(CH$_3$)$_3$).

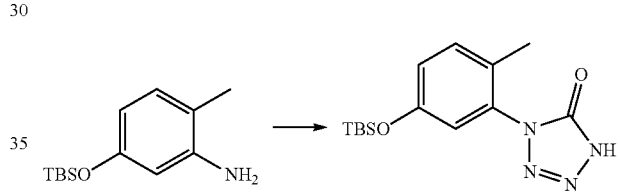

A solution of the aniline (0.271 g, 1.14 mmol, 1.0 eq) in toluene (2.0 mL) was added to a phosgene (1.63 mL of a 15% wt/wt solution in toluene, 2.29 mmol, 2.0 eq) at −15° C. dropwise, maintaining the internal temperature below 0° C. After complete addition, the reaction was heated to 90° C. for 3 hours. The reaction was cooled and concentrated to dryness, concentrating from EtOAc (2×15 mL) (to remove traces of hydrogen chloride). The residue was dried under vacuum for 1 hour and dissolved in azidotrimethylsilane (3 mL) at room temperature. The reaction was placed in a room temperature heating bath and the reaction slowly warmed to 90° C. Heating at 90° C. was maintained for 12 hours. The reaction was cooled and concentrated under reduced pressure. Column chromatography (silica, 10→50% EtOAc-hexane) yielded the tetrazalone (0.201 g, 57%) as a colourless oil; $^1$H NMR (CDCl$_3$) δ 7.22 (1H, d, J 8.5 Hz, C$_6$H$_3$H-5), 6.92 (1H, dd, J 8.5, 2.5 Hz, C$_6$H$_3$H-6), 6.86 (1H, d, J 2.0 Hz, C$_6$H$_3$H-2), 2.23 (3H, C$_6$H$_3$C$\underline{H}_3$), 0.99 (9H, s, SiC(CH$_3$)$_3$), 0.22 (6H, s, Si(C$\underline{H}_3$)$_2$C(CH$_3$)$_3$).

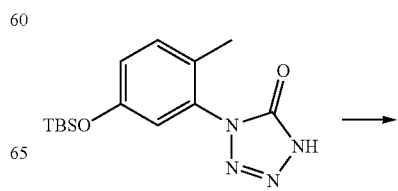

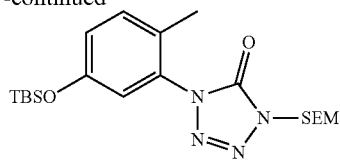

To a solution of the tetrazalone (0.201 g, 0.657 mmol, 1.0 eq) in dimethylformamide (6.5 mL) was added (trimethylsilyl)ethoxymethyl chloride (0.128 mL, 0.723 mmol, 1.1 eq) followed by ground potassium carbonate (0.109 g, 0.788 mmol, 1.2 eq). The reaction was stirred at room temperature for 14 hours and partitioned between EtOAc (80 mL) and water (80 mL). The organics were washed with brine (60 mL), water (80 mL) and brine (60 mL), dried (Na$_2$SO$_4$) and concentrated under reduced pressure. Column chromatography (silica, 5→40% EtOAc-hexane) yielded the (trimethylsilyl)ethoxymethyl protected product (0.157 g, 55%) as a colourless oil; $^1$H NMR (CDCl$_3$) δ 7.19 (1H, d, J 8.5 Hz, C$_6$H$_3$H-5), 6.87 (1H, dd, J 8.0, 2.5 Hz, C$_6$H$_3$H-6), 6.84 (1H, d, J 2.5 Hz, C$_6$H$_3$H-2), 5.38 (2H, s, NCH$_2$O), 3.76 (2H, m, OCH$_2$CH$_2$TMS), 2.20 (3H, C$_6$H$_3$CH$_3$), 0.98 (2H, m, OCH$_2$CH$_2$TMS), 0.97 (9H, s, SiC(CH$_3$)$_3$), 0.20 (6H, s, Si(CH$_3$)$_2$C(CH$_3$)$_3$), 0.02 (9H, s, Si(CH$_3$)$_3$).

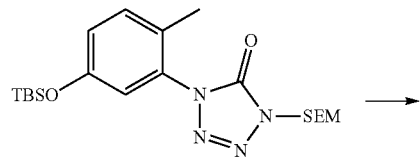

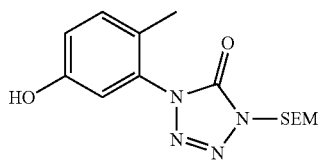

To a solution of the t-butyldimethylsilylether (0.157 g, 0.360 mmol, 1.0 eq) in tetrahydrofuran (3.5 mL) at 0° C. was added a solution of tetrabutylammonium fluoride (0.36 mL of a 1.0M solution in tetrahydrofuran, 0.360 mmol, 1.0 eq). The reaction was stirred at 0° C. for 15 minutes and NH$_4$Cl (25 mL) was added to quench the reaction. The organics were extracted with EtOAc (3×25 mL). The combined organics were dried (Na$_2$SO$_4$) and concentrated under reduced pressure. Column chromatography (silica, 5→40% EtOAc-hexane) yielded 3-(N-trimethylethoxymethyl)tetrazalon-1-yl)-4-methylphenol as a white waxy solid; $^1$H NMR (CDCl$_3$) δ 7.11 (1H, d, J 8.5 Hz, C$_6$H$_3$H-5), 6.76 (1H, dd, J 8.5, 2.5 Hz, C$_6$H$_3$H-6), 6.73 (1H, d, J 2.0 Hz, C$_6$H$_3$H-2), 5.41 (2H, s, NCH$_2$O), 3.77 (2H, m, OCH$_2$CH$_2$TMS), 2.14 (3H, C$_6$H$_3$CH$_3$), 0.99 (2H, m, OCH$_2$CH$_2$TMS), 0.01 (9H, s, Si(CH$_3$)$_3$).

Formation of 5-(N-Methylindol-5-yl)-6-fluorobenzimidazole and 5-(2'-Hydroxyphenyl-4-phenyl)-6-fluorobenzimidazole

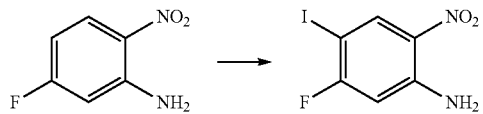 [SMILES: Nc1cc(F)ccc1[N+](=O)[O-] ; Nc1cc(F)c(I)cc1[N+](=O)[O-]]

To a solution of the fluoronitroaniline (2.00 g, 12.82 mmol, 1.0 eq) in acetic acid (30 mL) was added N-iodosuccinimide (3.17 g, 14.10 mmol, 1.1 eq). The reaction was heated to 70° C. for 4.5 hours. The reaction was cooled and poured into water (300 mL) forming a yellow precipitate, which was isolated by filtration to obtain the iodinated aniline (3.58 g, quantitative) as a yellow solid; $^1$H NMR (D$_6$-DMSO) δ 8.33 (1H, d, J 7.0 Hz, H-3), 7.65 (2H, br s, NH$_2$), 6.83 (1H, d, J 10.5 Hz, H-6); m/z: 283 [M+H]$^+$.

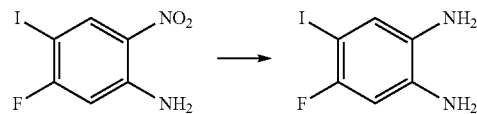 [SMILES: Nc1cc(F)c(I)cc1[N+](=O)[O-] ; Nc1cc(F)c(I)cc1N]

A suspension of the nitrobenzene (3.58 g, 12.70 mmol, 1.0 eq) in ethanol (30 mL) was heated to 80° C. forming a solution. A suspension of iron (3.55 g, 63.48 mmol, 5.0 eq) in aqueous ammonium chloride (3.40 g, 63.48 mmol, 5.0 eq in 20 mL of water) was added and the reaction stirred vigorously at 80° C. for 40 minutes before filtering hot through celite, eluting with EtOAc-EtOH (1:1, 60 mL). The filtrate was concentrated and partitioned between EtOAc (100 mL) and brine (80 mL). The aqueous phase was extracted with EtOAc (3×60 mL). The combined organics were dried (Na$_2$SO$_4$) and concentrated under reduced pressure to obtain a brown-black solid, which was used without further purification; $^1$H NMR (D$_6$-DMSO) δ 6.78 (1H, d, J 6.5 Hz, H-3), 6.37 (1H, d, J 10.5 Hz, H-6), 4.79 (2H, br s, NH$_2$); $^{19}$F NMR (D$_6$-DMSO) δ −111.3; m/z: 253 [M+H]$^+$.

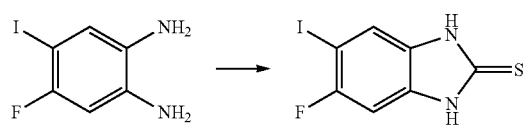 [SMILES: Nc1cc(F)c(I)cc1N ; Fc1cc2[nH]c(=S)[nH]c2cc1I]

To a solution of the crude fluoroiodobenzenediamine (12.70 mmol, 1.0 eq) in ethanol (20 mL) was added aqueous potassium hydroxide (0.71 g, 12.70 mmol, 1.0 eq in 4 mL of water) and carbon disulfide (0.76 mL, 12.70 mmol, 1.0 eq). The reaction was heated to reflux for 3.5 hours. After cooling the reaction was filtered and water (20 mL) added to the filtrate—a precipitate forms. Acetic acid (2 mL) in water (4 mL) was added forming more precipitate, which was isolated by filtration to obtain a brown solid (2.11 g, 57%); $^1$H NMR (D$_6$-DMSO) δ 7.42 (1H, d, J 5.5 Hz, H-3), 7.04 (1H, d, J 8.0 Hz, H-6); $^{19}$F NMR (D$_6$-DMSO) δ −101.8.

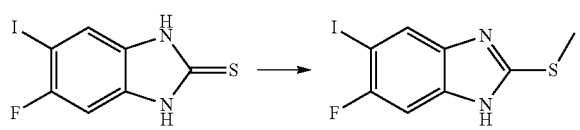

To a solution of the dihydrobenzathiazolethione (2.11 g, 7.18 mmol, 1.0 eq) in acetone (45 mL) at 0° C. was added ground potassium carbonate (0.50 g, 3.59 mmol, 0.5 eq) followed by iodomethane (0.22 mL, 3.59 mmol, 0.5 eq). The reaction was stirred at room temperature for 1 hour before cooling to 0° C. and adding ground potassium carbonate (0.50 g, 3.59 mmol, 0.5 eq) and iodomethane (0.22 mL, 3.59 mmol, 0.5 eq). The reaction was warmed to room temperature and stirred for 20 hours. The reaction was concentrated to remove the volatiles and the residue partitioned between EtOAc (100 mL) and water (75 mL). The aqueous phase was extracted with EtOAc (50 mL). The combined organics were washed with brine (100 mL), dried ($Na_2SO_4$) and concentrated under reduced pressure to yield a brown oil, which was used without purification; $^1$H NMR ($D_6$-DMSO) δ 7.90 (0.5H, d, J 6.0 Hz, 1 isomer of H-3), 7.72 (0.5H, d, J 6.0 Hz, 1 isomer of H-3), 7.41 (0.5H, d, J 8.0 Hz, 1 isomer of H-6), 7.30 (0.5H, d, J 8.0 Hz, 1 isomer of H-6), 2.66 (1.5H, s, 1 isomer of $SCH_3$), 2.65 (1.5H, s, 1 isomer of $SCH_3$); $^{19}$F NMR ($D_6$-DMSO) δ −102.8, −104.1; m/z: 309 [M+H]$^+$.

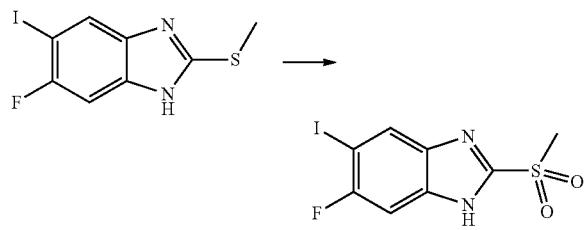

To a solution/suspension of the benzimidazole thiomethyl ether (2.16 g, 7.00 mmol, 1.0 eq) in dichloromethane (100 mL) was added m-chloroperoxybenzoic acid (3.23 g of a 75% solid, 14.03 mmol, 2.0 eq). A solution resulted, which was stirred at room temperature for 15 minutes. The reaction was added to $NaHCO_3$ (100 mL) and the organics extracted with $CH_2Cl_2$ (3×50 mL). The combined organics were washed with brine (100 mL), dried ($Na_2SO_4$) and concentrated under reduced pressure to obtain an orange foam (2.34 g), which was used without purification; m/z: 341 [M+H]$^+$.

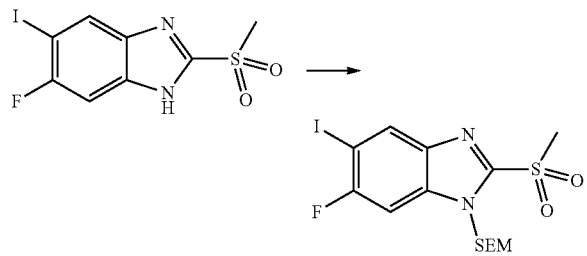

To a solution of the benzimidazole (2.34 g, 6.88 mmol, 1.0 eq) in tetrahydrofuran (20 mL) was added triethylamine (1.91 mL, 13.76 mmol, 2.0 eq) followed by 2-(trimethylsilyl)ethoxymethyl chloride (1.58 mL, 8.95 mmol, 1.3 eq). The reaction was stirred at room temperature for 90 minutes and concentrated to remove volatiles. The residue was partitioned between EtOAc (10 mL) and water (80 mL). The organics were washed with HCl (1M, 60 mL) and brine (60 mL), dried ($Na_2SO_4$) and concentrated under reduced pressure. The crude material was used without purification; $^1$H NMR ($D_6$-DMSO) δ 8.24 (0.5H, d, J 5.5 Hz, 1 isomer of H-3), 8.07 (0.5H, d, J 5.5 Hz, 1 isomer of H-3), 7.52 (0.5H, d, J 8.0 Hz, 1 isomer of H-6), 7.41 (0.5H, d, J 7.5 Hz, 1 isomer of H-6), 5.89 (1H, s, 1 isomer of $NCH_2O$), 5.87 (1H, s, 1 isomer of $NCH_2O$), 3.81 (2H, m, $OCH_2CH_2TMS$), 3.53 (1.5H, s, 1 isomer of $SO_2CH_3$), 3.52 (1.5H, s, 1 isomer of $SO_2CH_3$), 1.03-0.89 (2H, m, $OCH_2CH_2TMS$), 0.03 (4.5H, s, 1 isomer of $Si(CH_3)_3$), −0.03 (4.5H, s, 1 isomer of $Si(CH_3)_3$); $^{19}$F NMR ($D_6$-DMSO) δ −93.2, −97.4; m/z: 471 [M+H]$^+$.

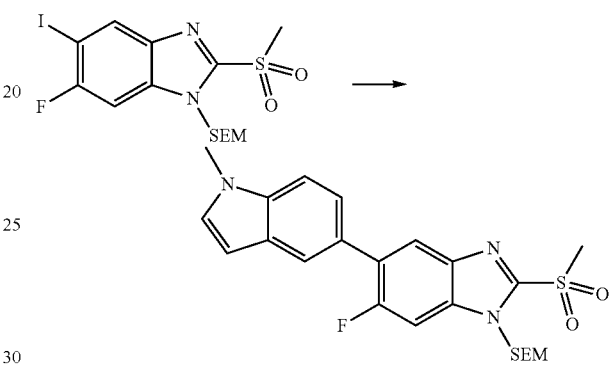

To a mixture of the iodobenzimidazole (0.132 g, 0.281 mmol, 1.0 eq) and N-methylindole-5-boronic acid (0.059 g, 0.337 mmol, 1.2 eq) was added dioxane (2.0 mL) followed by aqueous sodium carbonate (0.28 mL of a 2.0M solution, 0.562 mmol, 2.0 eq). The reaction was degassed by bubbling argon through the reaction mixture for five minutes. Tetrakis(triphenylphosphine)palladium (0.032 g, 0.028 mmol, 0.1 eq) was added and the reaction further degassed before heating in the microwave to 100° C. for 1 hour. The reaction was partitioned between EtOAc (50 mL) and water (50 mL). The organics were washed with brine (40 mL), dried ($Na_2SO_4$) and concentrated under reduced pressure. Column chromatography (silica, 5→50% EtOAc-hexane) yielded the coupled material; m/z: 475 [M+H]$^+$.

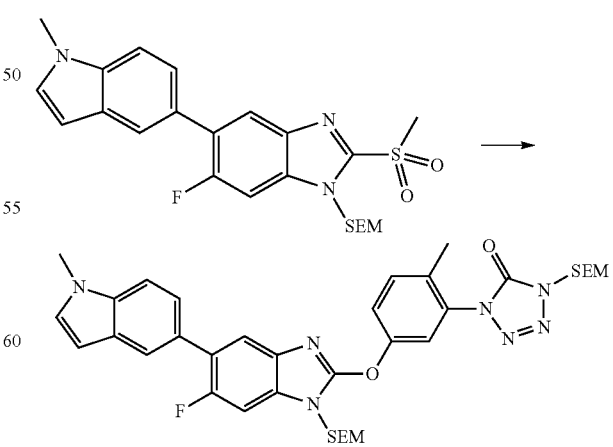

Dimethylformamide (1.0 mL) was added to a mixture of the benzimidazole methyl sulfone (0.030 g, 0.063 mmol, 1.0 eq), the phenol (0.031 g, 0.095 mmol, 1.5 eq) and ground potassium carbonate (0.034 g, 0.247 mmol, 3.9 eq). The reaction was stirred at room temperature for 20 hours and at 60° C. for 2 hours before cooling and partitioning between EtOAc (60 mL) and water (50 mL). The organics were washed with brine (50 mL), water (50 mL) and brine (50 mL), dried (Na$_2$SO$_4$) concentrated under reduced pressure. Column chromatography (silica, 10→50% EtOAc-hexane) yielded benzimidazole-2-phenyl ether (0.041 g, 90%) as a colourless oil; m/z: 717 [M+H]$^+$.

Compound 5: 1-(5-((6-fluoro-5-(1-methyl-1H-indol-5-yl)-1H-benzo[d]imidazol-2-yl)oxy)-2-methylphenyl)-1,4-dihydro-5H-tetrazol-5-one

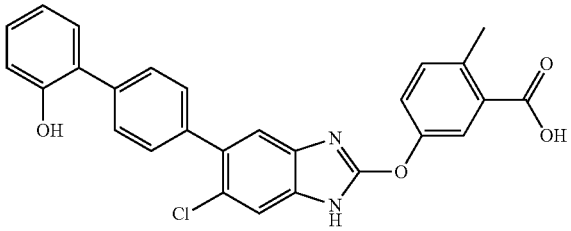 [SMILES: Cc1ccc(Oc2nc3cc(-c4ccc(-c5ccccc5O)cc4)c(Cl)cc3[nH]2)cc1C(=O)O]

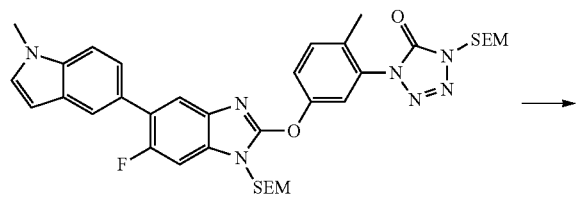

To a solution of the bis-((trimethylsilyl)ethoxymethyl) protected compound (0.041 g, 0.057 mmol, 1.0 eq) in tetrahydrofuran (0.5 mL) was added tetrabutylammonium fluoride (0.46 mL of a 1M solution in tetrahydrofuran, 0.459 mmol, 8.0 eq). The reaction was heated to 80° C. and stirred for 4 hours. Further tetrabutylammonium fluoride (0.23 mL, 0.230 mmol, 4.0 eq) was added and the reaction stirred for 2 hours. After cooling the reaction was partitioned between EtOAc (40 mL) and KHSO$_4$ (40 mL). The aqueous phase was extracted with EtOAc (2×30 mL). The combined organics were washed with water (40 mL) and brine (40 mL), dried (Na$_2$SO$_4$) and concentrated under reduced pressure. Column chromatography (silica, 0→10 MeOH—CH$_2$Cl$_2$) yielded Compound 5 as a white solid; $^1$H NMR (CD$_3$OD) δ 7.55-7.48 (3H, m, 3×ArH), 7.46-7.43 (2H, m, 2×ArH), 7.39 (1H, d, J 9.0 Hz, C$_6$H$_3$H-6 or indoleH-7), 7.36 (1H, s, BzimidazoleH-4 or H-7), 7.21 (1H, dd, J 8.5, 2.0 Hz, C$_6$H$_3$H-5 or indoleH-6), 7.18 (1H, d, J 3.5 Hz, indoleH-2 or H-3), 6.45 (1H, dd, J 3.0, 1.0 Hz, indoleH-2 or H-3), 3.83 (3H, s, NCH$_3$), 2.29 (3H, s, C$_6$H$_3$CH$_3$); m/z: 475, 473 [M+H]$^+$ (found [M+H]$^+$, 472.1253, C$_{24}$H$_{18}$ClN$_7$O$_2$ requires [M+H]$^+$ 472.1283).

Compound 2: 5-((6-chloro-5-(2'-hydroxy-[1,1'-biphenyl]-4-yl)-1H-benzo[d]imidazol-2-yl)oxy)-2-methylbenzoic acid

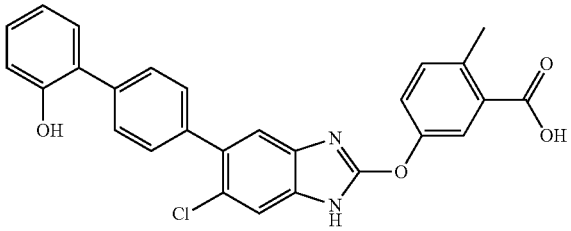 [SMILES: Cc1ccc(Oc2nc3cc(-c4ccc(-c5ccccc5O)cc4)c(Cl)cc3[nH]2)cc1C(=O)O]

$^1$H NMR (D$_6$-DMSO) δ 9.60 (1H, br s, 1×NH), 7.60 (2H, d, J 8.5 Hz, 2H of C$_6$H$_4$phenol), 7.53 (1H, s, BzimidazoleH-4 or H-7), 7.44 (2H, d, J 8.0 Hz, 2H of C$_6$H$_4$phenol), 7.36 (1H, s, BzimidazoleH-4 or H-7), 7.32 (1H, m, PhOH H-3 or H-6), 7.20 (1H, d, J 3.0 Hz, C$_6$H$_3$H-2), 7.16 (1H, m, PhOH H-4 or H-5), 7.04 (1H, d, J 8.5 Hz, C$_6$H$_3$H-5), 6.95 (1H, d, J 7.5 Hz, PhOH H-3 or H-6), 6.88 (1H, t, J 7.0 Hz, PhOH H-4 or H-5), 6.80 (1H, dd, J 8.5, 2.5 Hz, C$_6$H$_3$H-6), 2.36 (3H, s, C$_6$H$_3$CH$_3$); m/z: 474, 472 [M+H]$^+$ (found [M+H]$^+$, 471.1117, C$_{27}$H$_{19}$ClN$_2$O$_4$ requires [M+H]$^+$ 471.1106).

Compound 7: 5-((6-fluoro-5-(1-methyl-1H-indol-5-yl)-1H-benzo[d]imidazol-2-yl)oxy)-2-methylbenzoic acid

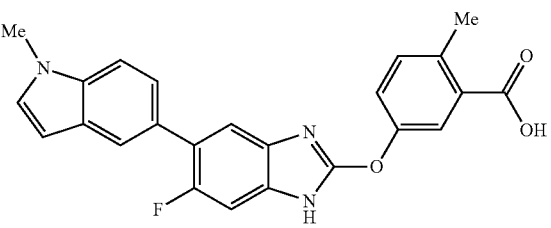 [SMILES: Cc1ccc(Oc2nc3cc(-c4ccc5c(ccn5C)c4)c(F)cc3[nH]2)cc1C(=O)O]

$^1$H NMR (CD$_3$OD) δ 7.81 (1H, d, J 2.0 Hz, indoleH-4 or C$_6$H$_3$H-2), 7.69 (1H, br s, indoleH-4 or C$_6$H$_3$H-2), 7.42-7.35 (5H, m, indoleH-6 and H-7, C$_6$H$_3$H-5 and H-6, BzimidazoleH-4), 7.16 (1H, d, J 11.0 Hz, BzimidazoleH-7), 7.14 (1H, d, J 3.0 Hz, indoleH-2 or H-3), 6.46 (1H, dd, J 3.0, 1.0 Hz, indoleH-2 or H-3), 3.82 (3H, s, NCH$_3$), 2.60 (3H, s, C$_6$H$_3$CH$_3$); $^{19}$F NMR (CD$_3$OD) δ −125.5; m/z: 417 [M+H]$^+$.

Compound 10: 4'-(6-fluoro-2-(4-methyl-3-(1H-tetrazol-1-yl)phenoxy)-1H-benzo[d]imidazol-5-yl)-[1,1'-biphenyl]-2-ol

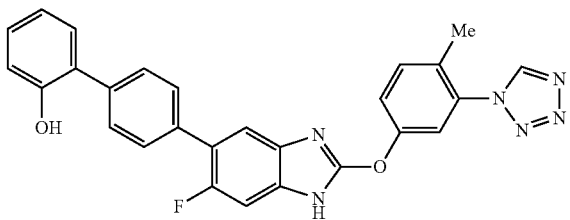 [SMILES: Cc1ccc(Oc2nc3cc(-c4ccc(-c5ccccc5O)cc4)c(F)cc3[nH]2)cc1-n1cnnn1]

$^1$H NMR (CD$_3$OD) δ 9.59 (1H, s, tetrazoleH-5), 7.69-7.58 (7H, m, C$_6$H$_4$phenol, BzimidazoleH-4, 2×ArH), 7.50 (1H, d, J 7.0 Hz, 1×ArH), 7.34 (1H, dd, J 8.0, 2.0 Hz, C$_6$H$_4$OH H-3 or H-6), 7.25 (1H, d, J 11.0 Hz, BzimidazoleH-7), 7.20 (1H, td, J 7.5, 2.0 Hz, C$_6$H$_4$OH H-4 or H-5), 6.95 (2H, m, 2×ArH), 2.28 (3H, s, C$_6$H$_3$CH$_3$); $^{19}$F NMR (CD$_3$OD) δ −125.7; m/z: 479 [M+H]$^+$ (found [M+H]$^+$, 479.1631, C$_{27}$H$_{19}$FN$_6$O$_2$ requires [M+H]$^+$ 479.1626).

Compound 12: 4'-(6-fluoro-2-(4-methyl-3-(2H-tetrazol-5-yl)phenoxy)-1H-benzo[d]imidazol-5-yl)-[1,1'-biphenyl]-2-ol

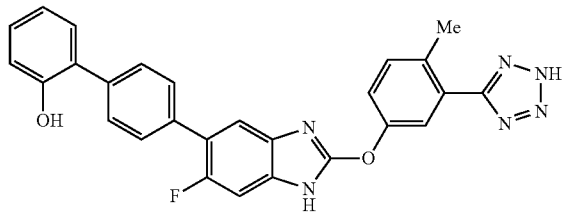 [SMILES: Cc1ccc(Oc2nc3cc(-c4ccc(-c5ccccc5O)cc4)c(F)cc3[nH]2)cc1-c1nn[nH]n1]

$^1$H NMR (CD$_3$OD) δ 7.71 (1H, d, J 2.5 Hz, C$_6$H$_3$H-2), 7.64 (2H, d, J 9.0 Hz, 2H of C$_6$H$_4$phenol), 7.57-7.53 (3H, m, 2H of C$_6$H$_4$phenol, C$_6$H$_3$H-6), 7.46-7.43 (2H, m, BzimidazoleH-4, C$_6$H$_3$H-6), 7.31 (1H, dd, J 8.0, 1.5 Hz, C$_6$H$_4$OH H-3 or H-6), 7.20 (1H, d, J 11.0 Hz, BzimidazoleH-7), 7.15 (1H, m, C$_6$H$_4$OH H-4 or H-5), 6.94-6.88 (2H, m, 2H of C$_6$H$_4$OH), 2.56 (3H, s, C$_6$H$_3$CH$_3$); $^{19}$F nmr (CD$_3$OD) δ −125.8; m/z: 480 [M+H]$^+$ (found [M+H]$^+$, 479.1619, C$_{27}$H$_{19}$FN$_6$O$_2$ requires [M+H]$^+$ 479.1626).

Compound 13: 1-(5-((6-fluoro-5-(2'-hydroxy-[1,1'-biphenyl]-4-yl)-1H-benzo[d]imidazol-2-yl)oxy)-2-methylphenyl)-4-methyl-1,4-dihydro-5H-tetrazol-5-one $^1$H nmr (CD$_3$OD) δ 7.82 (2H, d, J 8.5 Hz, 2H of C$_6$H$_4$phenol), 7.75-7.71 (3H, m, 3×ArH), 7.67-7.63 (3H, m, 3×ArH), 7.49 (1H, dd, J 8.0, 1.5 Hz, C$_6$H$_4$OH H-3 or H-6), 7.39 (1H, d, J 11.0 Hz, BzimidazoleH-7), 7.34 (1H, m, C$_6$H$_4$OH H-4 or H-5), 7.10 (1H, dd, J 6.0, 1.5 Hz, 1×ArH), 7.08 (1H, d, J 8.0 Hz, C$_6$H$_3$H-5), 3.87 (3H, s, NCH$_3$), 2.49 (3H, s, C$_6$H$_3$CH$_3$); $^{19}$F nmr (CD$_3$OD) δ −125.7; m/z: 510 [M+H]$^+$ (found [M+H]$^+$, 509.1737, C$_{28}$H$_{21}$FN$_6$O$_3$ requires [M+H]$^+$509.1732).

Example 2: AMPK In Vitro Kinase Assay

Materials:

Gutathione coated 384-well white plate (Fisher, Cat #NC18702X)

Anti-Rabbit-HRP conjugate (Cell Signaling Tech. Cat#7074S)

Phospho-Acetyl-CoA Carboxylase (Ser79) Antibody (Cell Signaling Tech. Cat#3661S)

GST-ACC2 (0.8 mg/ml stock) 40 µl (final 200 ng/well)

Low AMP (10 mM stock) Mixed with the GST-ACC (final 0.1 M)

GST-AMPK (0.5 mg/ml stock) 5 µl (final 200 ng/ml)

High AMP (10 mM stock) 5 µl (final 100 M)

75 µM ATP (10 mM stock) 5 µl (final 7.5 µM)

All diluted in 1× Kinase Buffer.

NaPy has to be added to AMPK when a new tube of AMPK is used.

NaPy Stock: 0.25M. Final concentration: 2 mM. *warm up in warm water for it to go into solution.

Procedures:
1. Add 500 nL/well of compound using Echo.
2. Add 40 µl/well of GST-ACC with low AMP to all wells.
3. Add 5 µl/well of 1 mM AMP to the last two columns, columns 23 & 24.
4. Add 5 µl/well of GST-AMPK to all well.
5. Add 5 µl/well of ATP to all well.
6. Shake for 1 min and incubate the kinase reaction at RT for 1 hr.
7. Wash plate twice with 50 µl TBST.
8. Add 1$^{st}$ antibody and 2$^{nd}$ antibody in 50 µl/well TBST with 1% BSA (1$^{st}$ antibody Anti-phospho ACC 1:4000 and 2$^{nd}$ antibody 1:6000 anti-rabbit-HRP). Incubate at RT for 1 hr.
9. Wash plate twice with 50 µl TBST.
10. Add 50 µl substrate (Millipore HRP substrate WBKLS0500) and read (gain 1800)

| Kinase Buffer | 100 ml | Stock |
|---|---|---|
| 50 mM Hepes pH 7.5 | 10 ml | 0.5M |
| 1 mM MgCl$_2$ | 1 ml | 1.0M |
| 1 mM EGTA pH 8.0 | 0.4 ml | 0.25M |
| 0.01% Brij-35 | 0.333 ml | 3% |
| 0.4 mM TCEP | 80 µl | 0.5M |
| TBST | 1000 ml | Stock |
| 150 mM NaCl | 30 ml | 5M |
| 20 mM Tris pH 7.5 | 20 ml | 1M |
| 0.05% Tween 20 | 0.5 ml | 100% |

ELISA Substrate (Per 100 µl)

25 µl solution A

25 µl solution B

50 µl ddH$_2$O (Millipore-WBKLS0500)

Note:

10 mM ATP, add 6 mg/mL 10 mM AMP, 3.47 mg/mL

Syringe A: ACC with low AMP to all wells.

NX: High AMP to last two columns (23 & 24)

Combi 1: AMPK to all wells.

Combi 2: ATP to all wells.

Peri: Antibodies to all wells.

Syringe B: Substrate to all wells.

The representative compounds activate AMPK with an EC$_{50}$ of less than 20 micromolar, such as less than 10 micromolar or less than 1 micromolar.

What is claimed:

1. A compound having the structure of formula (I):

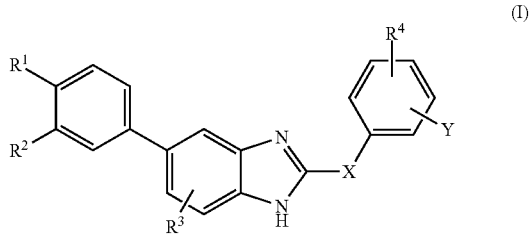

or a pharmaceutically acceptable salt, prodrug or N-oxide thereof, or solvate or hydrate thereof,
wherein
$R^1$ and $R^2$ together with the atoms to which they are attached form ring A, wherein ring A is a 5- or 6-membered Het optionally substituted with one or more $R^A$ groups that are each independently $C_{3-8}$ Cak($C_{0-6}$ alkyl), Hca($C_{0-6}$ alkyl), Ar($C_{0-6}$ alkyl), Het($C_{0-6}$ alkyl), —O—$C_{0-6}$ alkyl-$C_{3-8}$Cak, —O—$C_{0-6}$ alkyl-Hca, —O—$C_{0-6}$ alkyl-Ar, —O—$C_{0-6}$ alkyl-Het, halogen, cyano, $C_{1-6}$ alkyl, $C_{1-6}$ haloalkyl, -$C_1$-$C_6$alkoxy, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —CH$_2$—OP(O)(OR) wherein each Ar, Het, Cak, Hca, alkyl, alkoxy and haloalkyl group is optionally substituted by one or two -$R^{Ax}$ groups,
wherein each -$R^{Ax}$ is independently halogen, cyano, $C_{1-6}$ alkyl, $C_{1-6}$ haloalkyl, -$C_1$-$C_6$alkoxy, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —CH$_2$—OP(O)(OR);
or one of $R^1$ and $R^2$ is Ar or Het, wherein Ar and Het are optionally substituted with one or more independently selected $R^A$ groups, and the other is hydrogen, halogen, cyano, $C_{1-6}$ alkyl, $C_{1-6}$ haloalkyl, -$C_1$-$C_6$alkoxy, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —CH$_2$—OP(O)(OR);
$R^3$ and $R^4$ are independently hydrogen, halogen, cyano, $C_{1-6}$ alkyl, $C_{1-6}$ haloalkyl, -$C_1$-$C_6$alkoxy, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —CH$_2$—OP(O)(OR);
X is —O—, —S—, —NR— or —CF$_2$—;
Y is selected from $NR_2$, —CN, —C(O)NHOH,

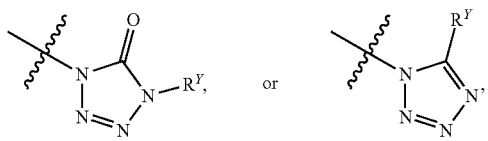

wherein $R^Y$ is hydrogen or $C_{1-6}$ alkyl; and
each R is independently hydrogen, $C_1$-$C_6$alkyl, $C_1$-$C_6$haloalkyl, -($C_0$-$C_6$alkyl)-Ar, -($C_0$-$C_6$alkyl)-Het, -($C_0$-$C_6$alkyl)-Cak, or -($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano;
or a pharmaceutically acceptable salt thereof.

2. The compound of claim 1 or a pharmaceutically acceptable salt, prodrug or N-oxide thereof, or solvate or hydrate thereof, wherein
$R^1$ and $R^2$ together with the atoms to which they are attached form ring A, wherein ring A is 5- or 6-membered Het optionally substituted with one or more $R^A$ groups that are each independently $C_{3-8}$ Cak($C_{0-6}$ alkyl), Hca($C_{0-6}$ alkyl), Ar($C_{0-6}$ alkyl), Het($C_{0-6}$ alkyl), —O-$C_{0-6}$alkyl-$C_{3-8}$Cak, —O-$C_{0-6}$alkyl-Hca, —O-$C_{0-6}$alkyl-Ar, —O-$C_{0-6}$alkyl-Het, halogen, cyano, $C_{1-6}$ alkyl, $C_{1-6}$ haloalkyl, -$C_1$-$C_6$alkoxy, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —CH$_2$—OP(O)(OR), wherein each Ar, Het, Cak, Hca, alkyl, alkoxy and haloalkyl group is optionally substituted by one or two -$R^{Ax}$ groups,
wherein each -$R^{Ax}$ is independently halogen, cyano, $C_{1-6}$ alkyl, $C_{1-6}$ haloalkyl, -$C_1$-$C_6$alkoxy, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —CH$_2$—OP(O)(OR);
or one of $R^1$ and $R^2$ is Ar or Het, wherein Ar and Het are substituted with one or more $R^A$ groups, and the other is hydrogen, halogen, cyano, $C_{1-6}$ alkyl, $C_{1-6}$ haloalkyl, -$C_1$-$C_6$alkoxy, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —CH$_2$—OP(O)(OR).

3. The compound of claim 1, or a pharmaceutically acceptable salt, prodrug or N-oxide thereof, or solvate or hydrate thereof, wherein
$R^1$ and $R^2$ together with the atoms to which they are attached form a 5- or 6-membered Het optionally substituted with one or more $R^A$ groups,
or one of $R^1$ and $R^2$ is Ar.

4. The compound of claim 1, or a pharmaceutically acceptable salt, prodrug or N-oxide thereof, or solvate or hydrate thereof, wherein
$R^1$ and $R^2$ together with the atoms to which they are attached form a 5- or 6-membered Het optionally substituted with one or more $R^A$ groups.

5. The compound of claim 1, or a pharmaceutically acceptable salt, prodrug or N-oxide thereof, or solvate or hydrate thereof, wherein
$R^1$ is Ar optionally substituted with one or more $R^A$ groups.

6. The compound of claim 1, or a pharmaceutically acceptable salt, prodrug or N-oxide thereof, or solvate or hydrate thereof, wherein
X is —O—.

7. The compound of claim 1, or a pharmaceutically acceptable salt, prodrug or N-oxide thereof, or solvate or hydrate thereof, wherein
each $R^A$ is independently halogen, cyano, $C_{1-6}$ alkyl, $C_{1-6}$ haloalkyl, -$C_1$-$C_6$alkoxy, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —CH$_2$—OP(O)(OR), wherein each alkyl, alkoxy and haloalkyl group is optionally substituted by one or two -$R^{Ax}$ groups,
wherein each -R is independently halogen, cyano, $C_{1-6}$ alkyl, $C_{1-6}$ haloalkyl, -$C_1$-$C_6$alkoxy, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —CH$_2$—OP(O)(OR).

8. The compound of claim 1, wherein the compound A compound that is
- 5-((6-chloro-5-(1-methyl-1H-indol-5-yl)-1H-benzo[d]imidazol-2-yl)oxy)-N-hydroxy-2-methylbenzamide;
- 5-((6-chloro-5-(2'-hydroxy-[1,1'-biphenyl]-4-yl)-1H-benzo[d]imidazol-2-yl)oxy)-2-methylbenzoic acid;
- 5-((6-chloro-5-(2'-hydroxy-[1,1'-biphenyl]-4-yl)-1H-benzo[d]imidazol-2-yl)oxy)-N-hydroxy-2-methylbenzamide;
- 1-(5-((6-chloro-5-(1-methyl-1H-indol-5-yl)-1H-benzo[d]imidazol-2-yl)oxy)-2-methylphenyl)-1,4-dihydro-5H-tetrazol-5-one;
- 1-(5-((6-fluoro-5-(1-methyl-1H-indol-5-yl)-1H-benzo[d]imidazol-2-yl)oxy)-2-methylphenyl)-1,4-dihydro-5H-tetrazol-5-one;
- 1-(5-((6-fluoro-5-(2'-hydroxy-[1,1'-biphenyl]-4-yl)-1H-benzo[d]imidazol-2-yl)oxy)-2-methylphenyl)-1,4-dihydro-5H-tetrazol-5-one;
- 5-((6-fluoro-5-(1-methyl-1H-indol-5-yl)-1H-benzo[d]imidazol-2-yl)oxy)-2-methylbenzoic acid;
- 1-(5-((6-chloro-5-(1-methyl-1H-indol-5-yl)-1H-benzo[d]imidazol-2-yl)oxy)-2-methylphenyl)-4-methyl-1,4-dihydro-5H-tetrazol-5-one;
- 5-((6-chloro-5-(1-methyl-1H-indol-5-yl)-1H-benzo[d]imidazol-2-yl)oxy)-2-methylaniline;
- 4'-(6-fluoro-2-(4-methyl-3-(1H-tetrazol-1-yl)phenoxy)-1H-benzo[d]imidazol-5-yl)-[1,1'-biphenyl]-2-ol;
- 5-((6-fluoro-5-(2'-hydroxy-[1,1'-biphenyl]-4-yl)-1H-benzo[d]imidazol-2-yl)oxy)-2-methylbenzonitrile;
- 4'-(6-fluoro-2-(4-methyl-3-(2H-tetrazol-5-yl)phenoxy)-1H-benzo[d]imidazol-5-yl)-[1,1'-biphenyl]-2-ol;
- 1-(5-((6-fluoro-5-(2'-hydroxy-[1,1'-biphenyl]-4-yl)-1H-benzo[d]imidazol-2-yl)oxy)-2-methylphenyl)-4-methyl-1,4-dihydro-5H-tetrazol-5-one;

or a pharmaceutically acceptable salt, prodrug or N-oxide thereof, or solvate or hydrate thereof.

9. The compound of claim 1, having the structure of formula (II):

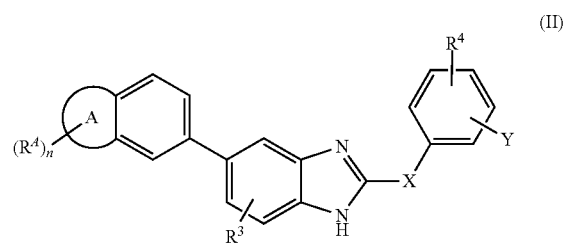

or a pharmaceutically acceptable salt, prodrug or N-oxide thereof, or solvate or hydrate thereof, wherein
ring A is a 5- or 6-membered Het; and
n is 1, 2, 3 or 4.

10. The compound of claim 9, or a pharmaceutically acceptable salt, prodrug or N-oxide thereof, or solvate or hydrate thereof, wherein
ring A is a 5-membered Het.

11. The compound of claim 9, or a pharmaceutically acceptable salt, prodrug or N-oxide thereof, or solvate or hydrate thereof, wherein
ring A is a 6-membered Het.

12. The compound of claim 9, or a pharmaceutically acceptable salt, prodrug or N-oxide thereof, or solvate or hydrate thereof, wherein
ring A is pyridyl, pyrimidinyl, pyrazinyl, pyridazinyl, pyrrolyl, furanyl, thiophenyl, pyrazolyl, imidazolyl, isoxazolyl, oxazolyl, isothiazolyl or thiazolyl.

13. The compound of claim 10, or a pharmaceutically acceptable salt, prodrug or N-oxide thereof, or solvate or hydrate thereof, wherein
ring A is pyrrolyl.

14. The compound of claim 10, or a pharmaceutically acceptable salt, prodrug or N-oxide thereof, or solvate or hydrate thereof, wherein
ring A is N-methylpyrrolyl.

15. The compound of claim 9, or a pharmaceutically acceptable salt, prodrug or N-oxide thereof, or solvate or hydrate thereof, wherein
each $R^A$ is independently halogen, cyano, $C_{1-6}$ alkyl, $C_{1-6}$ haloalkyl, -$C_1$-$C_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR), wherein each alkyl, alkoxy and haloalkyl group is optionally substituted by one or two -$R^{Ax}$ groups,
wherein each -$R^{Ax}$ is independently halogen, cyano, $C_{1-6}$ alkyl, $C_{1-6}$ haloalkyl, -$C_1$-$C_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).

16. The compound of claim 9, or a pharmaceutically acceptable salt, prodrug or N-oxide thereof, or solvate or hydrate thereof, wherein
X is —O—.

17. The compound of claim 9, or a pharmaceutically acceptable salt, prodrug or N-oxide thereof, or solvate or hydrate thereof, wherein
each R is independently hydrogen, $C_1$-$C_6$alkyl or $C_1$-$C_6$haloalkyl.

18. The compound of claim 1, having the structure of formula (III):

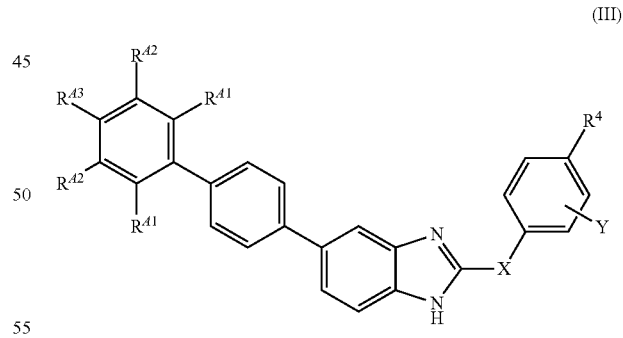

or a pharmaceutically acceptable salt, prodrug or N-oxide thereof, or solvate or hydrate thereof, wherein
each $R^{A1}$ is independently hydrogen, $C_{3-8}$ Cak($C_{0-6}$ alkyl), Hca($C_{0-6}$ alkyl), Ar($C_{0-6}$alkyl), Het($C_{0-6}$ alkyl), —O-$C_{0-6}$alkyl-$C_{3-8}$ Cak, —O-$C_{0-6}$alkyl-Hca, —O-$C_{0-6}$alkyl-Ar, —O-$C_{0-6}$alkyl-Het, cyano, $C_{1-6}$ haloalkyl, -$C_1$-$C_6$alkoxy, —OR, —SR, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

each $R^{A2}$ is independently hydrogen, $C_{3-8}$ Cak($C_{0-6}$ alkyl), Hca($C_{0-6}$ alkyl), Ar($C_{0-6}$ alkyl), Het($C_{0-6}$ alkyl), —O-$C_{0-6}$alkyl-$C_{3-8}$ Cak, —O-$C_{0-6}$alkyl-Hca, —O-$C_{0-6}$alkyl-Ar, —O-$C_{0-6}$alkyl-Het, cyano, $C_{1-6}$ alkyl, $C_{1-6}$ haloalkyl, -$C_1$-$C_6$alkoxy, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

$R^{A3}$ is hydrogen, $C_{3-8}$ Cak($C_{0-6}$ alkyl), Hca($C_{0-6}$ alkyl), Ar($C_{0-6}$ alkyl), Het($C_{0-6}$ alkyl), —O-$C_{0-6}$alkyl-$C_{3-8}$Cak, —O-$C_{0-6}$alkyl-Hca, —O-$C_{0-6}$alkyl-Ar, —O-$C_{0-6}$alkyl-Het, $C_{1-6}$ alkyl, $C_{1-6}$ haloalkyl, -$C_1$-$C_6$alkoxy, —SR, —NR$_2$, —C(O)R, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

wherein each Ar, Het, Cak, Hca, alkyl, alkoxy and haloalkyl group in each $R^{A1}$, $R^{A2}$ and $R^{A3}$ is optionally substituted by one or two -$R^{Ax}$ groups, wherein each -$R^{Ax}$ is independently halogen, cyano, $C_{1-6}$ alkyl, $C_{1-6}$ haloalkyl, -$C_1$-$C_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

$R^3$ is hydrogen, halogen, cyano, $C_{1-6}$ alkyl, $C_{1-6}$ haloalkyl, -$C_1$-$C_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$-OP(O)(OR);

$R^4$ is halogen, cyano, $C_{1-6}$ alkyl, $C_{1-6}$ haloalkyl, -$C_1$-$C_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

X is —O—, —S—, —NR— or —CF$_2$—;
Y is selected from —NR$_2$, —CN, —C(O)NHOH,

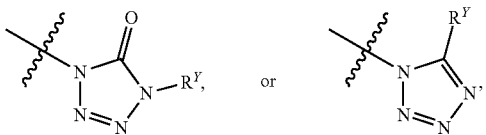

wherein $R^Y$ is hydrogen or $C_{1-6}$ alkyl; and each R is independently hydrogen, $C_1$-$C_6$alkyl, $C_1$-$C_6$haloalkyl, -($C_0$-$C_6$alkyl)-Ar, -($C_0$-$C_6$alkyl)-Het, -($C_0$-$C_6$alkyl)-Cak, or -($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano provided that
(a) at least one of $R^{A1}$, $R^{A2}$ or $R^{A3}$ is not hydrogen;
(b) when $R^{A1}$ or $R^{A5}$ is hydroxyl, $R^3$ is not fluoro; and
(c) when $R^{A1}$ or $R^{A5}$ is methoxy, $R^3$ is not chloro.

19. The compound of claim 18, or a pharmaceutically acceptable salt, prodrug or N-oxide thereof, or solvate or hydrate thereof, wherein each $R^{A1}$ is independently hydrogen, cyano, $C_{1-6}$ haloalkyl, -$C_1$-$C_6$alkoxy, —OR, —SR, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

each $R^{A2}$ is independently hydrogen, cyano, $C_{1-6}$ alkyl, $C_{1-6}$ haloalkyl, -$C_1$-$C_6$alkoxy, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

$R^{A3}$ is hydrogen, $C_{1-6}$ alkyl, $C_{1-6}$ haloalkyl, -$C_1$-$C_6$alkoxy, —SR, —NR$_2$, —C(O)R, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

wherein each alkyl, alkoxy and haloalkyl group in each $R^{A1}$, $R^{A2}$ and $R^{A3}$ is optionally substituted by one or two -$R^{Ax}$ groups.

20. The compound of claim 18, or a pharmaceutically acceptable salt, prodrug or N-oxide thereof, or solvate or hydrate thereof, wherein X is —O—.

21. The compound of claim 18, or a pharmaceutically acceptable salt, prodrug or N-oxide thereof, or solvate or hydrate thereof, wherein each R is independently hydrogen, $C_1$-$C_6$alkyl or $C_1$-$C_6$haloalkyl.

22. The compound of claim 1, having the structure of formula (IIIa):

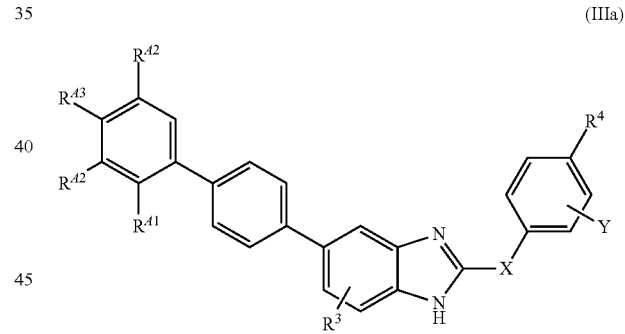

or a pharmaceutically acceptable salt, prodrug or N-oxide thereof, or solvate or hydrate thereof, wherein $R^{A1}$ is $C_{3-8}$ Cak($C_{0-6}$ alkyl), Hca($C_{0-6}$ alkyl), Ar($C_{0-6}$ alkyl), Het($C_{0-6}$ alkyl), —O-$C_{0-6}$alkyl-$C_{3-8}$ Cak, —O-$C_{0-6}$alkyl-Hca, —O-$C_{0-6}$alkyl-Ar, —O-$C_{0-6}$alkyl-Het, cyano, $C_{1-6}$ haloalkyl, -$C_1$-$C_6$alkoxy, —OH, —SR, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

each $R^{A2}$ group is independently hydrogen, $C_{3-8}$ Cak ($C_{0-6}$ alkyl), Hca($C_{0-6}$ alkyl), Ar($C_{0-6}$alkyl), Het($C_{0-6}$ alkyl), —O-$C_{0-6}$alkyl-$C_{3-8}$ Cak, —O-$C_{0-6}$alkyl-Hca, —O-$C_{0-6}$alkyl-Ar, —O-$C_{0-6}$alkyl-Het, cyano, $C_{1-6}$ alkyl, $C_{1-6}$ haloalkyl, -$C_1$-$C_6$alkoxy, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

R$^{A3}$ is hydrogen, C$_{3-8}$ Cak(C$_{0-6}$ alkyl), Hca(C$_{0-6}$ alkyl), Ar(C$_{0-6}$ alkyl), Het(C$_{0-6}$ alkyl), —O-C$_{0-6}$alkyl-C$_{3-8}$Cak, —O-C$_{0-6}$alkyl-Hca, —O-C$_{0-6}$alkyl-Ar, —O-C$_{0-6}$alkyl-Het, C$_{1-6}$ alkyl, C$_{1-6}$ haloalkyl, -C$_1$-C$_6$alkoxy, —SR, —NR$_2$, —C(O)R, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

wherein each Ar, Het, Cak, Hca, alkyl, alkoxy and haloalkyl group in each R$^{A1}$, R$^{A2}$ and R$^{A3}$ is optionally substituted by one or two -R$^{Ax}$ groups, wherein each -R$^{Ax}$ is independently halogen, cyano, C$_{1-6}$ alkyl, C$_{1-6}$ haloalkyl, -C$_1$-C$_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

R$^3$ is hydrogen, chloro, bromo, cyano, C$_{1-6}$ alkyl, C$_{1-6}$ haloalkyl, -C$_1$-C$_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

R$^4$ is halogen, cyano, C$_{1-6}$ alkyl, C$_{1-6}$ haloalkyl, -C$_1$-C$_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

X is —O—, —S—, —NR— or —CF$_2$-;

Y is selected from —NR$_2$, —CN, —C(O)NHOH,

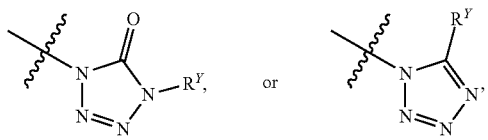

or wherein R$^Y$ is hydrogen or C$_{1-6}$ alkyl; and each R is independently hydrogen, C$_1$-C$_6$alkyl, C$_1$-C$_6$haloalkyl, -(C$_0$-C$_6$alkyl)-Ar, -(C$_0$-C$_6$alkyl)-Het, -(C$_0$-C$_6$alkyl)-Cak, or -(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$haloalkyl or cyano.

23. The compound of claim 22, or a pharmaceutically acceptable salt, prodrug or N-oxide thereof, or solvate or hydrate thereof, wherein R$^{A1}$ is cyano, C$_{1-6}$ haloalkyl, -C$_1$-C$_6$alkoxy, —OH, —SR, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

each R$^{A2}$ group is independently hydrogen, cyano, C$_{1-6}$ alkyl, C$_{1-6}$ haloalkyl, -C$_1$-C$_6$alkoxy, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

R$^{A3}$ is hydrogen, C$_{1-6}$ alkyl, C$_{1-6}$ haloalkyl, -C$_1$-C$_6$alkoxy, —SR, —NR$_2$, —C(O)R, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

wherein each alkyl, alkoxy and haloalkyl group in each R$^{A1}$, R$^{A2}$ and R$^{A3}$ is optionally substituted by one or two -R$^{Ax}$ groups.

24. The compound of claim 22, or a pharmaceutically acceptable salt, prodrug or N-oxide thereof, or solvate or hydrate thereof, wherein X is —O—.

25. The compound of claim 22, or a pharmaceutically acceptable salt, prodrug or N-oxide thereof, or solvate or hydrate thereof, wherein each R is independently hydrogen, C$_1$-C$_6$alkyl or C$_1$-C$_6$haloalkyl.

26. A pharmaceutical composition comprising a compound according to claim 1, or a pharmaceutically acceptable salt, prodrug, solvate, hydrate or N-oxide thereof, and a pharmaceutically acceptable excipient, diluent, or carrier.

27. A method for activating the AMPK pathway in a cell, the method comprising contacting the cell with an effective amount of the compound of claim 1, or a pharmaceutically acceptable salt, prodrug, solvate, hydrate or N-oxide thereof.

28. A method for increasing fatty acid oxidation in a cell, the method comprising contacting the cell with an effective amount of a compound of claim 1, or a pharmaceutically acceptable salt, prodrug, solvate, hydrate or N-oxide thereof.

29. A method for decreasing glycogen concentration in a cell, the method comprising contacting the cell with an effective amount of a compound of claim 1, or a pharmaceutically acceptable salt, prodrug, solvate, hydrate or N-oxide thereof.

30. A method for increasing glucose uptake in a cell, the method comprising contacting the cell with an effective amount of a compound of claim 1, or a pharmaceutically acceptable salt, prodrug, solvate, hydrate or N-oxide thereof.

31. A method for reducing triglyceride levels in a subject, the method comprising administering to the subject an effective amount of a compound of claim 1, or a pharmaceutically acceptable salt, prodrug, solvate, hydrate or N-oxide thereof.

32. A method for treating type II diabetes in a subject with type II diabetes, the method comprising administering to the subject a therapeutically effective amount of a compound of claim 1, or a pharmaceutically acceptable salt, prodrug, solvate, hydrate or N-oxide thereof to ameliorate type II diabetes or at least one symptom thereof in the subject.

33. A method for treating atherosclerosis or cardiovascular disease in a subject with atherosclerosis or cardiovascular disease, the method comprising administering to the subject a therapeutically effective amount of a compound of claim 1, or a pharmaceutically acceptable salt, prodrug, solvate, hydrate or N-oxide thereof, to ameliorate atherosclerosis, cardiovascular disease, or at least one symptom thereof in the subject.

* * * * *